(12) United States Patent
Willetts et al.

(10) Patent No.: US 8,133,849 B2
(45) Date of Patent: Mar. 13, 2012

(54) HERBICIDAL COMPOUNDS

(75) Inventors: Nigel James Willetts, Bracknell (GB); Matthew Robert Cordingley, Bracknell (GB); Patrick Jelf Crowley, Bracknell (GB); Suzanna Jane Riley, Bracknell (GB); Michael Drysdale Turnbull, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 12/742,840

(22) PCT Filed: Nov. 10, 2008

(86) PCT No.: PCT/GB2008/003786
§ 371 (c)(1),
(2), (4) Date: Aug. 30, 2010

(87) PCT Pub. No.: WO2009/063180
PCT Pub. Date: May 22, 2009

(65) Prior Publication Data
US 2010/0323889 A1    Dec. 23, 2010

(30) Foreign Application Priority Data
Nov. 15, 2007  (GB) .................................. 0722472.8

(51) Int. Cl.
*C07D 241/26*   (2006.01)
*C07D 513/04*   (2006.01)
*A01N 43/72*    (2006.01)
*A01N 43/90*    (2006.01)

(52) U.S. Cl. .......................................... 504/221; 544/48

(58) Field of Classification Search .................... 544/48; 504/221
See application file for complete search history.

(56) References Cited

U.S. PATENT DOCUMENTS
3,821,213 A    6/1974   Tong
3,845,044 A   10/1974   Tong

OTHER PUBLICATIONS

Zawisza, Tadeusz et al: "Pyridothiazines. IV. Synthesis and properties of 2H-4, 6-dimethyl-8-phenyl-7,8-dihydropyrido [2,3-c]1,2-thiazin-7-one derivatives", Acta Poloniae Pharmaceutica, 37(1), pp. 25-31, 1980.

*Primary Examiner* — Kahsay T Habte
(74) *Attorney, Agent, or Firm* — William A. Teoli, Jr.

(57) ABSTRACT

The present invention relates to compounds of formula (I), wherein $R^1$, $R^2$, $R^3$, $R^4$ and $R^5$ are as defined in claim 1; or a salt or N-oxide thereof. Furthermore, the present invention relates to processes for preparing compounds of formula (I), to intermediates used in the preparation of compounds of formula (I), to methods of controlling plants and compositions comprising compounds of formula (I).

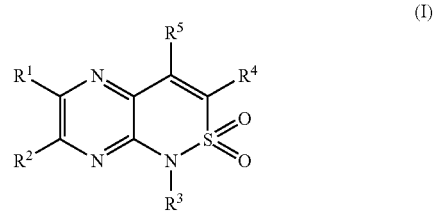

12 Claims, No Drawings

HERBICIDAL COMPOUNDS

This application is a 371 of International Application No. PCT/GB2008/003786 filed Nov. 10, 2008, which claims priority to GB 0722472.8 filed Nov. 15, 2007, the contents of which are incorporated herein by reference.

The present invention relates to novel herbicidal 1H-2-thia-1,5,8-triaza-naphthalene-2,2-dioxides, to processes for their preparation, to intermediates used in the preparation of such compounds, to compositions comprising those compounds, and to their use in controlling plants or in inhibiting plant growth.

It has now surprisingly been found that certain 1H-2-thia-1,5,8-triaza-naphthalene-2,2-dioxides display excellent herbicidal and growth-inhibiting properties.

The present invention therefore provides a compound of formula (I)

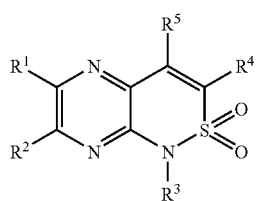

(I)

wherein
$R^1$ and $R^2$ are independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;
$R^3$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl-wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different;
$R^4$ is aryl or aryl substituted by one to five $R^8$, which may be the same or different, or heteroaryl or heteroaryl substituted by one to four $R^8$, which may be the same or different;
$R^5$ is hydroxy or a group which can be metabolized to a hydroxy group;
each $R^6$, $R^7$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy-substituted by one to three $R^{13}$, which may be the same or different, heteroaryloxy- or heteroaryloxy-substituted by one to three $R^{13}$, which may be the same or different, arylthio- or arylthio-substituted by one to three $R^{13}$, which may be the same or different, or heteroarylthio- or heteroarylthio-substituted by one to three $R^{13}$, which may be the same or different; and
each $R^{13}$ is independently halo, cyano, nitro, $C_1$-$C_6$alkyl, $C_1$-$C_6$haloalkyl or $C_1$-$C_6$alkoxy; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds. Furthermore, it is possible that atropisomers are obtained in those cases where the rotation of the $R^4$ group is restricted, for example in those cases where the $R^4$ group has at least one ortho-substituent.

For example, a compound of formula (A), i.e. a compound of formula (I) wherein $R^3$ is hydrogen and $R^5$ is hydroxy, can be drawn in two tautomeric forms.

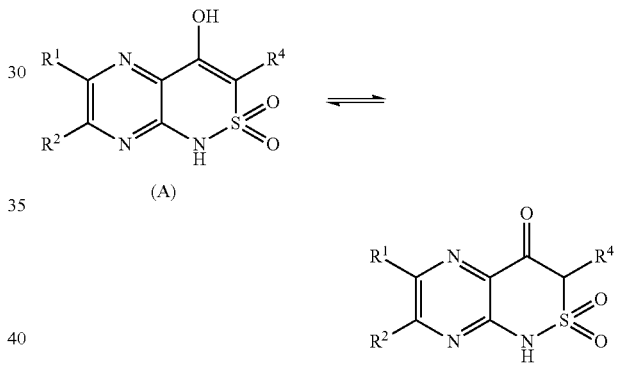

(A)

Some of these compounds exhibit good herbicidal activity. Additionally, these compounds can be used as intermediates for the synthesis of compounds of the formula (B), (C) and (D).

For example, a compound of formula (B), i.e. a compound of formula (I) wherein $R^3$ is hydrogen and $R^5$ is as defined for a compound of formula (I) other than hydroxy, can be drawn in only one tautomeric form.

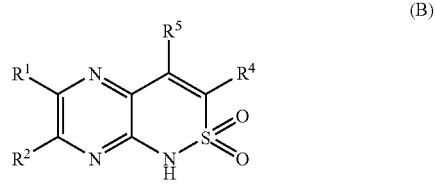

(B)

Some of these compounds exhibit good herbicidal activity. Additionally, these compounds can be used as intermediates for the synthesis of compounds of the formula (A), (C) and (D).

A compound of formula (C), i.e. a compound of formula (I) wherein $R^3$ is as defined for a compound of formula (I) other than hydrogen and $R^5$ is as defined for a compound of formula (I) other than hydroxy, can be drawn in only one tautomeric form.

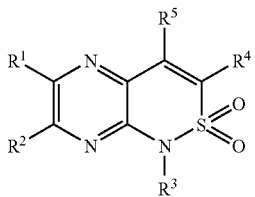
(C)

Most of these compounds exhibit excellent herbicidal activity. Additionally, these compounds can be used as intermediates for the synthesis of compounds of the formula (A), (B) and (D).

A compound of formula (D), i.e. a compound of formula (I) wherein $R^3$ is as defined for a compound of formula (I) other than hydrogen and $R^5$ is hydroxy, can be drawn in two tautomeric forms.

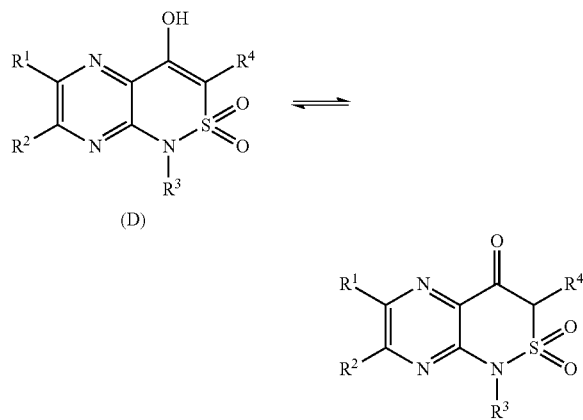
(D)

Most of these compounds exhibit good herbicidal activity. Additionally, these compounds can be used as intermediates for the synthesis of the formula (A), (B) and (C).

Each alkyl moiety (either alone or as part of a larger group, such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably $C_1$ to $C_6$ alkyl groups, more preferably $C_1$-$C_4$ and most preferably $C_1$-$C_3$ alkyl groups.

Alkenyl and alkynyl moieties (either alone or as part of a larger group, such as alkenyloxy or alkynyloxy) can be in the form of straight or branched chains, and the alkenyl moieties, where appropriate, can be of either the (E)- or (Z)-configuration. Examples are vinyl, allyl, prop-2-enyl and propargyl. The alkenyl and alkynyl groups are preferably $C_2$ to $C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CHF_2$, —$CH_2CF_3$ or —$CH_2CHF_2$. Haloalkenyl and haloalkynyl groups (either alone or as part of a larger group, such as haloalkenyloxy or haloalkynyloxy) are alkenyl and alkynyl groups, respectively, which are substituted with one or more of the same or different halogen atoms and are, for example, —CH=$CF_2$, —CCl=CClF or —C≡CCl.

Cyanoalkyl groups are alkyl groups which are substituted with one or more cyano groups, for example, cyanomethyl or 1,3-dicyanopropyl.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methylcyclopropyl, 2-methylcyclopropyl, cyclobutyl, cyclopentyl and cyclohexyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings contain up to three heteroatoms and bicyclic systems up to four heteroatoms which are preferably chosen from nitrogen, oxygen and sulfur. Examples of monocyclic groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred monocyclic heteroaryl group is pyridyl, such as 3-ethoxycarbonyl-6-trifluoromethyl-pyrid-2-yl. Examples of bicyclic groups are benzothiophenyl, benzimidazolyl, benzothiadiazolyl, quinolinyl, cinnolinyl, quinoxalinyl and pyrazolo[1,5-a]pyrimidinyl. A preferred bicyclic heteroaryl group is quinolinyl, such as 2-chloro-quinolin-2-yl.

The term "heterocyclyl" is defined to include heteroaryl and in addition their unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation. The term "metabolism" as used herein means the conversion or breakdown of a substance from one form to another by a living organism, in particular in a plant (in planta).

Preferred values of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are, in any combination, as set out below.

Preferably $R^1$ is hydrogen, $C_1$-$C_4$alkyl, $C_1$-$C_4$haloalkyl, halo, cyano, hydroxy or $C_1$-$C_4$alkoxy, more preferably hydrogen, $C_1$-$C_4$alkyl, halo, cyano or hydroxy, even more preferably hydrogen, methyl, chloro or bromo, yet even more preferably hydrogen or chloro, most preferably hydrogen.

Preferably $R^2$ is hydrogen, $C_1$-$C_4$alkyl, $C_1$-$C_4$haloalkyl, halo, cyano, hydroxy or $C_1$-$C_4$alkoxy, more preferably hydrogen, $C_1$-$C_4$alkyl, halo, cyano or hydroxy, even more preferably hydrogen, methyl, chloro or bromo, yet even more preferably hydrogen or chloro, most preferably hydrogen.

Preferably $R^3$ is hydrogen, $C_1$-$C_4$alkyl, $C_1$-$C_4$haloalkyl, $C_2$-$C_4$alkenyl, $C_2$-$C_4$haloalkenyl, $C_2$-$C_4$alkynyl or $C_2$-$C_4$haloalkynyl. Examples of such preferred groups for $R^3$ are hydrogen, methyl, ethyl, n-propyl, iso-propyl, n-butyl, 2-methyl-propyl, 2-fluoro-ethyl, 2,2-difluoro-ethyl, 2,2,2-trifluoro-ethyl, allyl, but-3-en-1-yl and propargyl.

More preferably $R^3$ is hydrogen, $C_1$-$C_2$alkyl, $C_1$-$C_2$haloalkyl, $C_2$-$C_3$alkenyl or $C_2$-$C_3$alkynyl. Examples of such more preferred groups for $R^3$ are hydrogen, methyl, ethyl, 2,2-difluoro-ethyl, 2,2,2-trifluoro-ethyl, allyl and propargyl.

Most preferably $R^3$ is hydrogen, $C_1$-$C_2$alkyl, $C_1$-$C_2$haloalkyl or $C_2$-$C_3$alkynyl. Examples of such most preferred groups for $R^3$ are hydrogen, methyl, ethyl, 2,2-difluoro-ethyl and propargyl.

Preferably $R^4$ is aryl or aryl substituted by one to five $R^8$, which may be the same or different, more preferably $R^4$ is aryl substituted by one to four $R^8$, which may be the same or different, most preferably $R^4$ is aryl substituted by two to three $R^8$, which may be the same or different.

In one preferred embodiment $R^4$ is 2,5-bis-(trifluoromethyl)-phenyl.

In one preferred embodiment $R^4$ is 3-bromo-2-chloro-6-fluoro-phenyl.

In one preferred embodiment $R^4$ is 4-bromo-2-trifluoromethyl-phenyl.

In one preferred embodiment $R^4$ is 2-chloro-3,6-difluoro-phenyl.

In one preferred embodiment $R^4$ is 2-chloro-5-fluoro-phenyl.

In one preferred embodiment $R^4$ is 2-chloro-5-trifluoromethyl-phenyl.

In one preferred embodiment $R^4$ is 2-chloro-6-trifluoromethyl-phenyl.

In one preferred embodiment $R^4$ is 4-chloro-2-trifluoromethyl-phenyl.

In one preferred embodiment $R^4$ is 5-chloro-2-trifluoromethyl-phenyl.

In one preferred embodiment $R^4$ is 2,3-dichloro-6-fluoro-phenyl.

In one preferred embodiment $R^4$ is 2,6-dichloro-phenyl.

In one preferred embodiment $R^4$ is 2,6-dichloro-4-trifluoromethoxy-phenyl.

In one preferred embodiment $R^4$ is 2-iodo-phenyl.

In one preferred embodiment $R^4$ is 2,3,6-trichloro-phenyl.

Preferably $R^5$ is hydroxy, $R^9$-oxy-, $R^{10}$-carbonyloxy-, tri-$R^{11}$-silyloxy- or $R^{12}$-sulfonyloxy-, wherein $R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;

$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio-substituted by one to three $R^{14}$, which may be the same or different; each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;

$R^{12}$ is $C_1$-$C_{10}$alkyl, $C_1$-$C_{10}$haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy; and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy.

More preferably $R^5$ is hydroxy, $R^9$-oxy- or $R^{10}$-carbonyloxy-.

Even more preferably $R^5$ is hydroxy, $C_1$-$C_4$alkoxy, $C_1$-$C_4$alkenyloxy, $C_1$-$C_4$alkynyloxy, aryl-$C_1$-$C_4$alkoxy or aryl-$C_1$-$C_4$alkoxy wherein the aryl moiety is substituted by one to three $R^{14}$, which may be the same or different, heteroaryl-$C_1$-$C_4$alkoxy or heteroaryl-$C_1$-$C_4$alkoxy wherein the heteroaryl moiety is substituted by one to three $R^{14}$, which may be the same or different, $C_1$-$C_4$alkylcarbonyloxy-, $C_3$-$C_6$cyclo-alkylcarbonyloxy-, $C_3$-$C_{10}$cycloalkyl-$C_1$-$C_{10}$alkylcarbonyloxy-, $C_1$-$C_4$haloalkylcarbonyl-oxy-, $C_2$-$C_4$alkenylcarbonyloxy-, $C_2$-$C_4$alkenylcarbonyloxy-, $C_1$-$C_4$alkoxy-$C_1$-$C_4$alkyl-carbonyloxy-, $C_1$-$C_4$alkylthio-$C_1$-$C_4$alkylcarbonyloxy-, $C_1$-$C_4$alkoxycarbonyloxy-, $C_2$-$C_4$alkenyloxycarbonyloxy-, $C_2$-$C_4$alkenyloxycarbonyloxy-, $C_1$-$C_4$alkylthiocarbonyloxy-, N—$C_1$-$C_4$alkyl-aminocarbonyloxy-, N,N-di-($C_1$-$C_4$alkyl)-aminocarbonyloxy-, aryl-carbonyloxy- or arylcarbonyloxy-substituted by one to three $R^{14}$, which may be the same or different, heteroarylcarbonyloxy- or heteroarylcarbonyloxy-substituted by one to three $R^{14}$, which may be the same or different, aryl-$C_1$-$C_4$alkylcarbonyloxy- or aryl-$C_1$-$C_4$alkylcarbonyloxy- wherein the aryl moiety is substituted by one to three $R^{14}$, which may be the same or different, heteroaryl-$C_1$-$C_4$alkylcarbonyloxy- or heteroaryl-$C_1$-$C_4$alkylcarbonyloxy- wherein the heteroaryl moiety is substituted by one to three $R^{14}$, which may be the same or different, aryloxycarbonyloxy- or aryloxycarbonyloxy-substituted by one to three $R^{14}$, which may be the same or different, heteroaryloxy-carbonyloxy- or heteroaryloxycarbonyloxy-substituted by one to three $R^{14}$, which may be the same or different, arylthiocarbonyloxy- or arylthiocarbonyloxy-substituted by one to three $R^{14}$, which may be the same or different, or heteroarylthiocarbonyloxy- or heteroarylthiocarbonyloxy-substituted by one to three $R^{14}$, which may be the same or different.

Yet even more preferably $R^5$ is hydroxy, $C_1$-$C_4$alkylcarbonyloxy-, $C_3$-$C_6$cyclo-alkylcarbonyloxy-, $C_2$-$C_4$alkenylcarbonyloxy-, $C_2$-$C_4$alkynylcarbonyloxy-, $C_1$-$C_4$alkoxycarbonyloxy-, $C_2$-$C_4$alkenyloxycarbonyloxy-, $C_2$-$C_4$alkynyloxycarbonyloxy- or $C_1$-$C_4$alkylthiocarbonyloxy-.

Most preferably $R^5$ is hydroxy, $C_1$-$C_4$alkylcarbonyloxy-, $C_1$-$C_4$alkoxycarbonyloxy- or $C_1$-$C_4$alkylthiocarbonyloxy-. Examples of most preferred groups for $R^5$ are hydroxy, methylcarbonyloxy-, ethylcarbonyloxy-, iso-propylcarbonyloxy-, n-propyl-carbonyloxy-, but-2-ylcarbonyloxy-, 2-methyl-propylcarbonyloxy-, tert-butylcarbonyl-oxy-, ethoxycarbonyloxy-, and ethylthiocarbonyloxy-.

In one preferred embodiment $R^5$ is hydroxy.

In one preferred embodiment $R^5$ is $R^9$-oxy-, wherein $R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy. Such $R^5$ groups may be metabolized, preferably in planta, to give the corresponding compound wherein $R^5$ is hydroxy.

In one preferred embodiment $R^5$ is $R^{10}$-carbonyloxy-, wherein $R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, $C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio-substituted by one to three $R^{14}$, which may be the same or different; and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy. Such $R^5$ groups may be metabolized, preferably in planta, to give the corresponding compound wherein $R^5$ is hydroxy.

In one preferred embodiment $R^5$ is iso-propylcarbonyloxy- or tert-butyl-carbonyloxy-.

Preferably each $R^6$ is independently halo, $C_1$-$C_4$alkyl, $C_1$-$C_4$haloalkyl, $C_1$-$C_4$alkoxy or $C_1$-$C_4$haloalkoxy. Examples of such preferred groups for $R^6$ are chloro, fluoro, methyl, ethyl, trifluoromethyl, methoxy or trifluoromethoxy.

Preferably each $R^7$ is independently halo, $C_1$-$C_4$alkyl, $C_1$-$C_4$haloalkyl, $C_r$-$C_4$alkoxy or $C_1$-$C_4$haloalkoxy. Examples of such preferred groups for $R^7$ are chloro, fluoro, methyl, ethyl, trifluoromethyl, methoxy and trifluoromethoxy.

Preferably each $R^8$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl- or $C_1$-$C_4$haloalkylsulfonyl-.

More preferably each $R^8$ is independently halo, cyano, nitro, $C_1$-$C_{10}$alkyl, $C_1$-$C_4$haloalkyl, $C_1$-$C_{10}$alkoxy, $C_1$-$C_4$haloalkoxy, $C_1$-$C_{10}$alkylthio or $C_1$-$C_4$haloalkylthio. Examples of such more preferred groups for $R^8$ are iodo, bromo, chloro, fluoro, cyano, nitro, methyl, ethyl, trifluoromethyl, methoxy, trifluoromethoxy and trifluoromethylthio.

Most preferably each $R^8$ is independently halo, $C_1$-$C_{10}$alkyl, $C_1$-$C_4$haloalkyl, $C_1$-$C_{10}$alkoxy or $C_1$-$C_4$haloalkoxy. Examples of such most preferred groups for $R^8$ are bromo, chloro, fluoro, methyl, ethyl, trifluoromethyl, methoxy and trifluoromethoxy.

Preferably $R^9$ is $C_2$-$C_{10}$alkenyl, $C_2$-$C_{10}$alkynyl, $RO_2C$—$C_1$-$C_4$alkyl- or $RO_2C$—$C_1$-$C_4$alkyl- wherein R is $C_1$-$C_4$alkyl, or aryl-$C_1$-$C_4$alkyl- or aryl-$C_1$-$C_4$alkyl- wherein the aryl moiety is substituted by one to three $R^{13}$, which may be the same or different, more preferably $R^9$ is $C_3$-$C_4$alkenyl, $C_3$-$C_4$alkynyl, $RO_2C$-methyl- or $RO_2C$-methyl- wherein R is $C_1$-$C_4$alkyl, or benzyl or benzyl wherein the phenyl moiety is substituted by one to three $R^{13}$, which may be the same or different, even more preferably $R^9$ is allyl, propargyl or benzyl, most preferably $R^9$ is allyl.

Preferably $R^{10}$ is $C_1$-$C_4$alkyl, $C_3$-$C_6$cycloalkyl, $C_3$-$C_{10}$cycloalkyl-$C_1$-$C_{10}$alkyl, $C_1$-$C_4$haloalkyl, $C_2$-$C_4$alkenyl, $C_2$-$C_4$alkynyl, $C_1$-$C_4$alkoxy-$C_1$-$C_4$alkyl, $C_1$-$C_4$alkylthio-$C_1$-$C_4$alkyl, $C_1$-$C_4$alkoxy, $C_2$-$C_4$alkenyloxy, $C_2$-$C_4$alkynyloxy, $C_1$-$C_4$alkylthio, N—$C_1$-$C_4$alkyl-amino, N,N-di-($C_1$-$C_4$alkyl)-amino, aryl or aryl substituted by one to three $R^{14}$, which may be the same or different, heteroaryl or heteroaryl substituted by one to three $R^{14}$, which may be the same or different, aryl-$C_1$-$C_4$alkyl or aryl-$C_1$-$C_4$alkyl wherein the aryl moiety is substituted by one to three $R^{14}$, which may be the same or different, heteroaryl-$C_1$-$C_4$alkyl or heteroaryl-$C_1$-$C_4$alkyl wherein the heteroaryl moiety is substituted by one to three $R^{14}$, which may be the same or different, aryloxy or aryloxy substituted by one to three $R^{14}$, which may be the same or different, heteroaryloxy or heteroaryloxy substituted by one to three $R^{14}$, which may be the same or different, arylthio or arylthio substituted by one to three $R^{14}$, which may be the same or different, heteroarylthio or heteroarylthio substituted by one to three $R^{14}$, which may be the same or different, or $RO_2C$-carbonyl- or $RO_2C$-carbonyl- wherein R is $C_1$-$C_4$alkyl.

More preferably $R^{10}$ is iso-propyl, tert-butyl, cyclopropyl, ethoxy, methylthio, ethylthio, or phenylthio.

Most preferably $R^{10}$ is iso-propyl or tert-butyl.

Preferably each $R^{11}$ is independently $C_1$-$C_4$alkyl.

Preferably $R^{12}$ is $C_1$-$C_4$alkyl or $C_1$-$C_4$haloalkyl, most preferably methyl or trifluoromethyl.

Preferably each $R^{13}$ is independently halo, nitro, $C_1$-$C_4$alkyl, $C_1$-$C_4$haloalkyl or $C_1$-$C_4$alkoxy. Examples of such preferred groups are chloro, fluoro, nitro, methyl, ethyl, trifluoromethyl and methoxy.

Preferably each $R^{14}$ is independently halo, nitro, $C_1$-$C_4$alkyl, $C_1$-$C_4$haloalkyl, $C_1$-$C_4$alkoxy or $C_1$-$C_4$haloalkoxy. Examples of such preferred groups are chloro, fluoro, nitro, methyl, ethyl, trifluoromethyl, methoxy and trifluoromethoxy.

In one embodiment the invention provides a compound of formula (X)

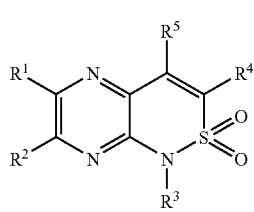

(X)

wherein $R^1$, $R^2$, $R^4$ and $R^5$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; or a salt or N-oxide thereof. The preferences for $R^1$, $R^2$, $R^4$, $R^5$, $R^6$, $R^7$, $R^8$, $R^9$, $R^{10}$, $R^{11}$, $R^{12}$, $R^{13}$ and $R^{14}$ are the same as the preferences set out for the corresponding substituents of a compound of formula (I). The preferences for $R^3$ are the same as the preferences set out for the corresponding substituents of a compound of formula (I) except that $R^3$ cannot be hydrogen.

In another embodiment the invention provides a compound of formula (C)

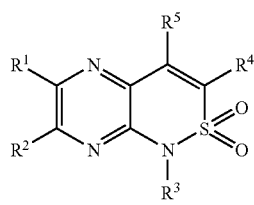

(C)

wherein $R^1$, $R^2$ and $R^4$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; and $R^5$ is $R^9$-oxy-, $R^{10}$-carbonyloxy-, tri-$R^{11}$-silyloxy- or $R^{12}$-sulfonyloxy-; or a salt or N-oxide thereof. The preferences for $R^1$, $R^2$, $R^4$, $R^6$, $R^7$, $R^8$, $R^9$, $R^{10}$, $R^{11}$, $R^{12}$, $R^{13}$ and $R^{14}$ are the same as the preferences set out for the corresponding substituents of a compound of formula (I). The preferences for $R^3$ are the same as the preferences set out for the corresponding substituents of a compound of formula (I) except that $R^3$ cannot be hydrogen. The preferences for $R^5$ are the same as the preferences set out for the corresponding substituents of a compound of formula (I) except that $R^5$ cannot be hydroxy.

In another embodiment the invention provides a compound of formula (D)

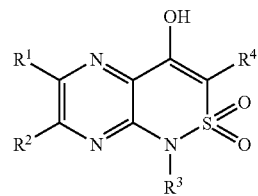

(D)

wherein $R^1$, $R^2$ and $R^4$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; or a salt or N-oxide thereof. The preferences for $R^1$, $R^2$, $R^4$, $R^6$, $R^7$, $R^8$ and $R^{13}$ are the same as the preferences set out for the corresponding substituents of a compound of formula (I). The preferences for $R^3$ are the same as the preferences set out for the corresponding substituents of a compound of formula (I) except that $R^3$ cannot be hydrogen.

Certain intermediates are novel and as such form part of the invention. One such group are compounds of formula (J) wherein $R^1$, $R^2$, and $R^4$ are as defined for a compound of formula (I); and $R^{16}$ is $C_1$-$C_6$alkyl; or a salt or N-oxide thereof.

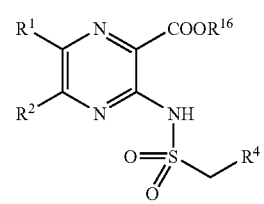

(J)

The preferences for $R^1$, $R^2$, and $R^4$ are the same as the preferences set out for the corresponding substituents of a compound of formula (I). Preferably $R^{16}$ is methyl or ethyl, most preferably methyl.

Another group are compounds of formula (K) wherein $R^1$, $R^2$, and $R^4$ are as defined for a compound of formula (I); $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; and $R^{16}$ is $C_1$-$C_6$alkyl; or a salt or N-oxide thereof.

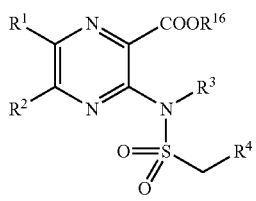

(K)

The preferences for $R^1$, $R^2$, and $R^4$ are the same as the preferences set out for the corresponding substituents of a compound of formula (I). The preferences for $R^3$ are the same as the preferences set out for the corresponding substituents of a compound of formula (I) except that $R^3$ cannot be hydrogen. Preferably $R^{16}$ is methyl or ethyl, most preferably methyl.

The compounds in Tables 1 to 29 below illustrate the compounds of the invention.

TABLE 1

Table 1 provides 70 compounds of formula (I), where $R^1$ and $R^2$ are both hydrogen, $R^4$ is 2,5-bis-(trifluoromethyl)-phenyl, and $R^3$ and $R^5$ have the values listed in Table 1.

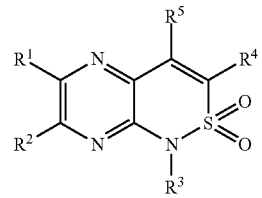

(I)

| Compound number | $R^3$ | $R^5$ |
|---|---|---|
| 1.001 | H | —OH |
| 1.002 | H | —OCOCH₃ |
| 1.003 | H | —OCOCH₂CH₃ |
| 1.004 | H | —OCOCH(CH₃)₂ |
| 1.005 | H | —OCO(CH₂)₂CH₃ |
| 1.006 | H | —OCOCH(CH₃)CH₂CH₃ |
| 1.007 | H | —OCOCH₂CH(CH₃)₂ |
| 1.008 | H | —OCOC(CH₃)₃ |
| 1.009 | H | —O(CO)OCH₂CH₃ |
| 1.010 | H | —O(CO)SCH₂CH₃ |
| 1.011 | —CH₃ | —OH |
| 1.012 | —CH₃ | —OCOCH₃ |
| 1.013 | —CH₃ | —OCOCH₂CH₃ |
| 1.014 | —CH₃ | —OCOCH(CH₃)₂ |
| 1.015 | —CH₃ | —OCO(CH₂)₂CH₃ |
| 1.016 | —CH₃ | —OCOCH(CH₃)CH₂CH₃ |
| 1.017 | —CH₃ | —OCOCH₂CH(CH₃)₂ |
| 1.018 | —CH₃ | —OCOC(CH₃)₃ |
| 1.019 | —CH₃ | —O(CO)OCH₂CH₃ |
| 1.020 | —CH₃ | —O(CO)SCH₂CH₃ |
| 1.021 | —CH₂CH₃ | —OH |
| 1.022 | —CH₂CH₃ | —OCOCH₃ |
| 1.023 | —CH₂CH₃ | —OCOCH₂CH₃ |
| 1.024 | —CH₂CH₃ | —OCOCH(CH₃)₂ |
| 1.025 | —CH₂CH₃ | —OCO(CH₂)₂CH₃ |
| 1.026 | —CH₂CH₃ | —OCOCH(CH₃)CH₂CH₃ |
| 1.027 | —CH₂CH₃ | —OCOCH₂CH(CH₃)₂ |
| 1.028 | —CH₂CH₃ | —OCOC(CH₃)₃ |
| 1.029 | —CH₂CH₃ | —O(CO)OCH₂CH₃ |
| 1.030 | —CH₂CH₃ | —O(CO)SCH₂CH₃ |
| 1.031 | —CH₂CHF₂ | —OH |
| 1.032 | —CH₂CHF₂ | —OCOCH₃ |
| 1.033 | —CH₂CHF₂ | —OCOCH₂CH₃ |
| 1.034 | —CH₂CHF₂ | —OCOCH(CH₃)₂ |
| 1.035 | —CH₂CHF₂ | —OCO(CH₂)₂CH₃ |
| 1.036 | —CH₂CHF₂ | —OCOCH(CH₃)CH₂CH₃ |
| 1.037 | —CH₂CHF₂ | —OCOCH₂CH(CH₃)₂ |
| 1.038 | —CH₂CHF₂ | —OCOC(CH₃)₃ |
| 1.039 | —CH₂CHF₂ | —O(CO)OCH₂CH₃ |
| 1.040 | —CH₂CHF₂ | —O(CO)SCH₂CH₃ |
| 1.041 | —CH₂CF₃ | —OH |
| 1.042 | —CH₂CF₃ | —OCOCH₃ |
| 1.043 | —CH₂CF₃ | —OCOCH₂CH₃ |
| 1.044 | —CH₂CF₃ | —OCOCH(CH₃)₂ |
| 1.045 | —CH₂CF₃ | —OCO(CH₂)₂CH₃ |
| 1.046 | —CH₂CF₃ | —OCOCH(CH₃)CH₂CH₃ |
| 1.047 | —CH₂CF₃ | —OCOCH₂CH(CH₃)₂ |
| 1.048 | —CH₂CF₃ | —OCOC(CH₃)₃ |
| 1.049 | —CH₂CF₃ | —O(CO)OCH₂CH₃ |
| 1.050 | —CH₂CF₃ | —O(CO)SCH₂CH₃ |
| 1.051 | —CH₂CH=CH₂ | —OH |
| 1.052 | —CH₂CH=CH₂ | —OCOCH₃ |
| 1.053 | —CH₂CH=CH₂ | —OCOCH₂CH₃ |
| 1.054 | —CH₂CH=CH₂ | —OCOCH(CH₃)₂ |
| 1.055 | —CH₂CH=CH₂ | —OCO(CH₂)₂CH₃ |
| 1.056 | —CH₂CH=CH₂ | —OCOCH(CH₃)CH₂CH₃ |
| 1.057 | —CH₂CH=CH₂ | —OCOCH₂CH(CH₃)₂ |
| 1.058 | —CH₂CH=CH₂ | —OCOC(CH₃)₃ |
| 1.059 | —CH₂CH=CH₂ | —O(CO)OCH₂CH₃ |
| 1.060 | —CH₂CH=CH₂ | —O(CO)SCH₂CH₃ |
| 1.061 | —CH₂C≡CH | —OH |
| 1.062 | —CH₂C≡CH | —OCOCH₃ |
| 1.063 | —CH₂C≡CH | —OCOCH₂CH₃ |
| 1.064 | —CH₂C≡CH | —OCOCH(CH₃)₂ |
| 1.065 | —CH₂C≡CH | —OCO(CH₂)₂CH₃ |
| 1.066 | —CH₂C≡CH | —OCOCH(CH₃)CH₂CH₃ |
| 1.067 | —CH₂C≡CH | —OCOCH₂CH(CH₃)₂ |
| 1.068 | —CH₂C≡CH | —OCOC(CH₃)₃ |
| 1.069 | —CH₂C≡CH | —O(CO)OCH₂CH₃ |
| 1.070 | —CH₂C≡CH | —O(CO)SCH₂CH₃ |

Table 2:

Table 2 provides 70 compounds of formula (I), where $R^1$ and $R^2$ are both hydrogen, $R^4$ is 3-bromo-2-chloro-6-fluoro-phenyl, and $R^3$ and $R^5$ have the values listed in Table 1.

Table 3:

Table 3 provides 70 compounds of formula (I), where $R^1$ and $R^2$ are both hydrogen, $R^4$ is 4-bromo-2-trifluoromethyl-phenyl, and $R^3$ and $R^5$ have the values listed in Table 1.

Table 4:

Table 4 provides 70 compounds of formula (I), where $R^1$ and $R^2$ are both hydrogen, $R^4$ is 2-chloro-3,6-difluoro-phenyl, and $R^3$ and $R^5$ have the values listed in Table 1.

Table 5:

Table 5 provides 70 compounds of formula (I), where $R^1$ and $R^2$ are both hydrogen, $R^4$ is 2-chloro-4-fluoro-phenyl, and $R^3$ and $R^5$ have the values listed in Table 1.

Table 6:

Table 6 provides 70 compounds of formula (I), where $R^1$ and $R^2$ are both hydrogen, $R^4$ is 2-chloro-5-fluoro-phenyl, and $R^3$ and $R^5$ have the values listed in Table 1.

Table 7:
Table 7 provides 70 compounds of formula (I), where $R^1$ and $R^2$ are both hydrogen, $R^4$ is 2-chloro-phenyl, and $R^3$ and $R^5$ have the values listed in Table 1.
Table 8:
Table 8 provides 70 compounds of formula (I), where $R^1$ and $R^2$ are both hydrogen, $R^4$ is, 2-chloro-3-trifluoromethyl-phenyl, and $R^3$ and $R^5$ have the values listed in Table 1.
Table 9:
Table 9 provides 70 compounds of formula (I), where $R^1$ and $R^2$ are both hydrogen, $R^4$ is 2-chloro-5-trifluoromethyl-phenyl, and $R^3$ and $R^5$ have the values listed in Table 1.
Table 10:
Table 10 provides 70 compounds of formula (I), where $R^1$ and $R^2$ are both hydrogen, $R^4$ is 2-chloro-6-trifluoromethyl-phenyl, and $R^3$ and $R^5$ have the values listed in Table 1.
Table 11:
Table 11 provides 70 compounds of formula (I), where $R^1$ and $R^2$ are both hydrogen, $R^4$ is 4-chloro-2-trifluoromethyl-phenyl, and $R^3$ and $R^5$ have the values listed in Table 1.
Table 12:
Table 12 provides 70 compounds of formula (I), where $R^1$ and $R^2$ are both hydrogen, $R^4$ is 5-chloro-2-trifluoromethyl-phenyl, and $R^3$ and $R^5$ have the values listed in Table 1.
Table 13:
Table 13 provides 70 compounds of formula (I), where $R^1$ and $R^2$ are both hydrogen, $R^4$ is 2,3-dichloro-6-fluoro-phenyl, and $R^3$ and $R^5$ have the values listed in Table 1.
Table 14:
Table 14 provides 70 compounds of formula (I), where $R^1$ and $R^2$ are both hydrogen, $R^4$ is 2,4-dichloro-5-fluoro-phenyl, and $R^3$ and $R^5$ have the values listed in Table 1.
Table 15:
Table 15 provides 70 compounds of formula (I), where $R^1$ and $R^2$ are both hydrogen, $R^4$ is 3,5-dichloro-2-methoxy-phenyl, and $R^3$ and $R^5$ have the values listed in Table 1.
Table 16:
Table 16 provides 70 compounds of formula (I), where $R^1$ and $R^2$ are both hydrogen, $R^4$ is 2,3-dichloro-phenyl, and $R^3$ and $R^5$ have the values listed in Table 1.
Table 17:
Table 17 provides 70 compounds of formula (I), where $R^1$ and $R^2$ are both hydrogen, $R^4$ is 2,4-dichloro-phenyl, and $R^3$ and $R^5$ have the values listed in Table 1.
Table 18:
Table 18 provides 70 compounds of formula (I), where $R^1$ and $R^2$ are both hydrogen, $R^4$ is 2,5-dichloro-phenyl, and $R^3$ and $R^5$ have the values listed in Table 1.
Table 19:
Table 19 provides 70 compounds of formula (I), where $R^1$ and $R^2$ are both hydrogen, $R^4$ is 2,6-dichloro-phenyl, and $R^3$ and $R^5$ have the values listed in Table 1.
Table 20:
Table 20 provides 70 compounds of formula (I), where $R^1$ and $R^2$ are both hydrogen, $R^4$ is 2,6-dichloro-4-trifluoromethoxy-phenyl, and $R^3$ and $R^5$ have the values listed in Table 1.
Table 21:
Table 21 provides 70 compounds of formula (I), where $R^1$ and $R^2$ are both hydrogen, $R^4$ is 2,6-dichloro-4-trifluoromethyl-phenyl, and $R^3$ and $R^5$ have the values listed in Table 1.
Table 22:
Table 22 provides 70 compounds of formula (I), where $R^1$ and $R^2$ are both hydrogen, $R^4$ is 2,6-diethyl-4-methyl-phenyl, and $R^3$ and $R^5$ have the values listed in Table 1.
Table 23:
Table 23 provides 70 compounds of formula (I), where $R^1$ and $R^2$ are both hydrogen, $R^4$ is 2,3-dimethoxy-phenyl, and $R^3$ and $R^5$ have the values listed in Table 1.
Table 24:
Table 24 provides 70 compounds of formula (I), where $R^1$ and $R^2$ are both hydrogen, $R^4$ is 2-iodo-phenyl, and $R^3$ and $R^5$ have the values listed in Table 1.
Table 25:
Table 25 provides 70 compounds of formula (I), where $R^1$ and $R^2$ are both hydrogen, $R^4$ is 2-methoxy-5-trifluoromethoxy-phenyl, and $R^3$ and $R^5$ have the values listed in Table 1.
Table 26:
Table 26 provides 70 compounds of formula (I), where $R^1$ and $R^2$ are both hydrogen, $R^4$ is 2,3,6-trichloro-phenyl, and $R^3$ and $R^5$ have the values listed in Table 1.
Table 27:
Table 27 provides 70 compounds of formula (I), where $R^1$ and $R^2$ are both hydrogen, $R^4$ is 2-trifluoromethoxy-phenyl, and $R^3$ and $R^5$ have the values listed in Table 1.
Table 28:
Table 28 provides 70 compounds of formula (I), where $R^1$ and $R^2$ are both hydrogen, $R^4$ is 2-trifluoromethyl-phenyl, and $R^3$ and $R^5$ have the values listed in Table 1.
Table 29:
Table 29 provides 70 compounds of formula (I), where $R^1$ and $R^2$ are both hydrogen, $R^4$ is 2,4,6-trimethyl-phenyl, and $R^3$ and $R^5$ have the values listed in Table 1.

The compounds of the invention may be made by a variety of methods, for example, by the methods described in Schemes 1 to 10.

Scheme 1

$R^4\text{—}X$ (E) $\xrightarrow{M_2SO_3}$ $R^4\text{—}CH_2\text{—}S(=O)_2\text{—}O^- M^+$ (F) $\xrightarrow{\text{halogenating agent}}$ $R^4\text{—}CH_2\text{—}S(=O)_2\text{—}X$ (G)

1) Compounds of formula (F) wherein $R^4$ is as defined for a compound of formula (I) can be prepared by reaction of a benzyl halide of formula (E) wherein $R^4$ is as defined for a compound of formula (I) and X is halogen, such as bromine, with a metal sulfite, such as sodium sulfite, as shown in Scheme 1. For example, if (E) is a benzyl bromide (i.e. where X is bromine) the reaction can conveniently be carried out in a suitable solvent, such as water, optionally in the presence of a suitable co-solvent, such as acetone, optionally using microwave heating. Similar methods have been described, for example, in Synthetic Communications 25(9), 1303, 1995. Compounds of formula (E) are commercially available or can be made by methods known to the person skilled in the art. A route to certain benzyl halides is, for example, described in Scheme 6 below.

2) Compounds of formula (G) wherein $R^4$ is as defined for a compound of formula (I) and X is halogen, such as chlorine, can be prepared by treating a compound of formula (F) as defined in 1) with a halogenating agent, such as phosphorus pentachloride, optionally in a suitable solvent, such as toluene, optionally using microwave heating.

Scheme 2

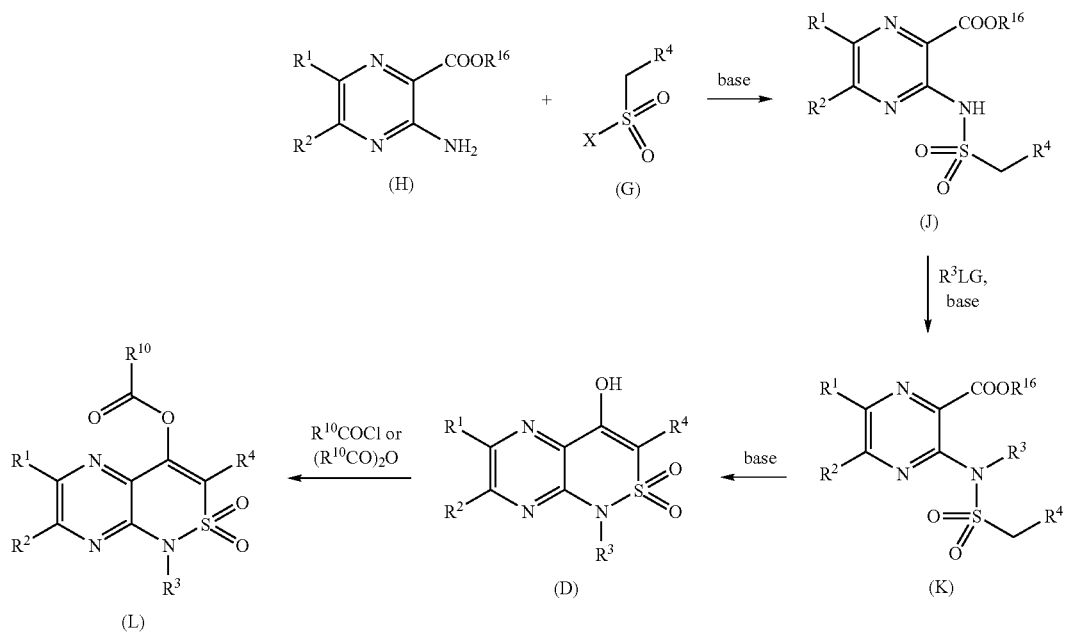

3) Compounds of formula (J) wherein $R^1$, $R^2$ and $R^4$ are as defined for a compound of formula (I) and $R^{16}$ is $C_1$-$C_6$alkyl can be prepared by reaction of an amino-pyrazine ester of formula (H) wherein $R^1$ and $R^2$ are as defined for a compound of formula (I) and $R^{16}$ is $C_1$-$C_6$alkyl with an acid derivative of formula (G) as defined in 2) as shown in Scheme 2. For example, if (G) is a sulfonyl chloride (i.e. where X is chlorine) the reaction can conveniently be carried out in the presence of a base, such as triethylamine or pyridine, in a suitable solvent, such as acetonitrile or dichloromethane, optionally using microwave heating. Compounds of formula (H) are commercially available or can be made by methods known to the person skilled in the art.

4) Compounds of formula (K), wherein $R^1$, $R^2$, $R^3$ and $R^4$ are as defined for a compound of formula (I) and $R^{16}$ is $C_1$-$C_6$alkyl can be prepared from a compound of formula (J) as defined in 3) by reaction with a compound of formula $R^3LG$ wherein $R^3$ is as defined for a compound of formula (I) other than hydrogen, and LG is a leaving group such as a halide, for example bromide or iodide, or tosylate, mesylate or triflate, with a base, such as N,N-diisopropylethylamine, in a suitable solvent, such as acetonitrile, optionally using microwave heating.

5) Compounds of formula (D), i.e. a compound of formula (I) wherein $R^3$ is as defined for a compound of formula (I) other than hydrogen and $R^5$ is hydroxy, can be prepared by treating a compound of formula (K) as defined in 4) with a base, such as lithium hexamethyldisilazide, sodium hexamethyldisilazide or potassium carbonate, in a suitable solvent, such as tetrahydrofuran or N,N-dimethylformamide, optionally using microwave heating.

6) Compounds of formula (L), i.e. a compound of formula (I) wherein $R^3$ is as defined for a compound of formula (I) other than hydrogen and $R^5$ is —O—CO—$R^{10}$, can be prepared by reaction of a compound of formula (D) as defined in 5) with an acid chloride of formula $R^{10}COCl$ or an acid anhydride of formula $(R^{10}CO)_2O$ wherein $R^{10}$ is as defined for a compound of formula (I), optionally in the presence of a base, such as pyridine or 4-dimethylaminopyridine, optionally in a suitable solvent, such as dichloro-methane or acetonitrile, optionally using microwave heating.

Scheme 3

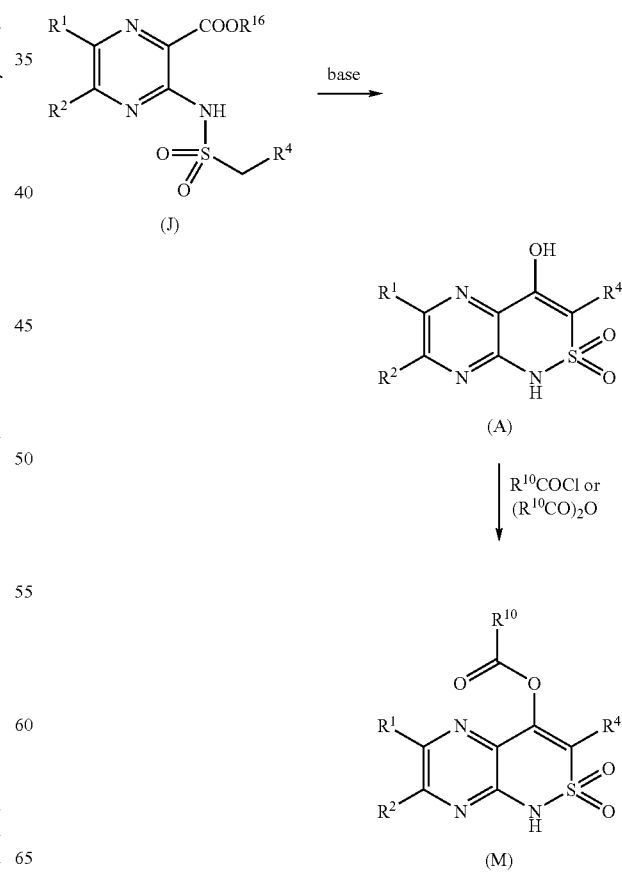

7) Compounds of formula (A), i.e. a compound of formula (I) wherein $R^3$ is hydrogen and $R^5$ is hydroxy, can be prepared by treating a compound of formula (J) as defined in 3) with a base, such as lithium hexamethyldisilazide, sodium hexamethyldisilazide or potassium carbonate, in a suitable solvent, such as tetrahydrofuran or N,N-dimethylformamide, optionally using microwave heating, as shown in Scheme 3.

8) Compounds of formula (M), i.e. a compound of formula (I) wherein $R^3$ is hydrogen and $R^5$ is —O—CO—$R^{10}$, can be prepared by reaction of a compound of formula (A) as defined in 7) with an acid chloride of formula $R^{10}$COCl or an acid anhydride of formula $(R^{10}CO)_2O$ wherein $R^{10}$ is as defined for a compound of formula (I), optionally in the presence of a base, such as pyridine, optionally in a suitable solvent, such as dichloromethane, optionally using microwave heating.

Scheme 4

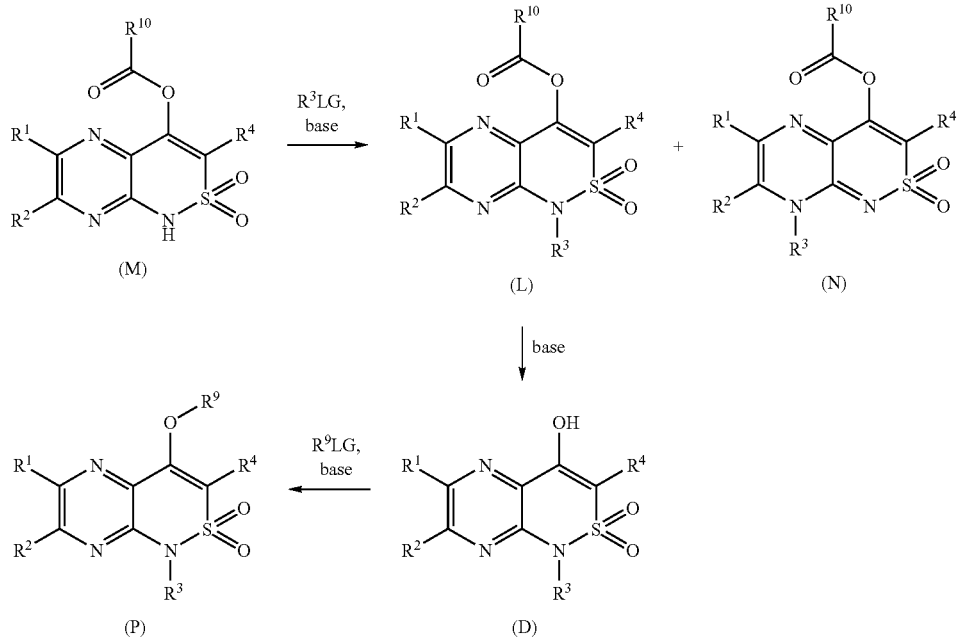

9) Compounds of formula (L) as defined in 6), and compounds of formula (N) wherein $R^1$, $R^2$, $R^4$ and $R^{10}$ are as defined for a compound of formula (I) and $R^3$ is as defined for a compound of formula (I) other than hydrogen, can be prepared from a compound of formula (M) as defined in 8) by reaction with a compound of formula $R^3$LG as defined in 4) in the presence of a base, such as N,N-diisopropylethylamine, in a suitable solvent, such as acetonitrile or N,N-dimethylformamide, optionally using microwave heating, as shown in Scheme 4. The nature of the compound of formula $R^3$LG and the choice of base can determine the ratio of compounds of formula (L) and compounds of formula (N).

10) Compounds of formula (D) as defined in 5) can be prepared by treating a compound of formula (L) as defined in 6) with a base, such as sodium hydroxide or potassium trimethylsilanolate, in a suitable solvent, such as tetrahydrofuran or aqueous methanol.

11) Compounds of formula (P), i.e. a compound of formula (I) wherein $R^3$ is as defined for a compound of formula (I) other than hydrogen and $R^5$ is —O—$R^9$, can be prepared from a compound of formula (D) as defined in 5) by reaction with a compound of formula $R^9$LG wherein $R^9$ is as defined for a compound of formula (I) and LG is a leaving group such as a halide, for example bromide or iodide, or tosylate, mesylate or triflate, in the presence of a base, such as potassium carbonate, in a suitable solvent, such as N,N-dimethylformamide or acetonitrile.

Scheme 5

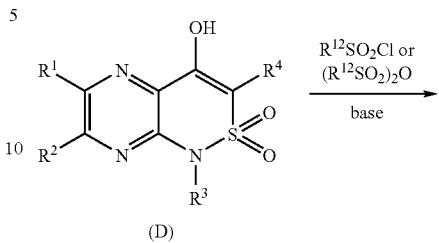

-continued

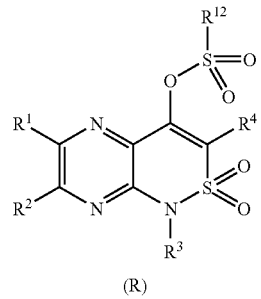

12) Sulfonyl compounds of formula (R), i.e. a compound of formula (I) wherein $R^3$ is as defined for a compound of formula (I) other than hydrogen and $R^5$ is —O—$SO_2$—$R^{12}$, can be prepared by reaction of a compound of formula (D) as defined in 5) with a sulfonyl chloride of formula $R^{12}SO_2Cl$ or a sulfonyl anhydride of formula $(R^{12}SO_2)_2O$ wherein $R^{12}$ is as defined for a compound of formula (I), in the presence of a base, such as N,N-diisopropylethylamine, optionally in a suitable solvent, such as dichloromethane, optionally using microwave heating, as shown in Scheme 5.

Scheme 6

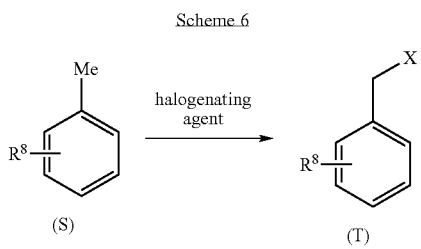

14) In certain cases where benzyl halides are not commercially available it is necessary to make them. A typical synthesis is shown in Scheme 6. Benzyl halides of formula (T) wherein $R^8$ is as defined for a compound of formula (I) and X is halogen, such as bromine, can be made from a substituted toluene of formula (S) wherein $R^8$ is as defined for a compound of formula (I), with a halogenating agent, such as halogen of formula $X_2$ wherein X is chlorine or bromine, in the presence of light, or a N-halosuccinimide of formula

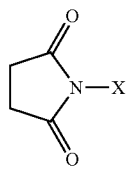

wherein X is chlorine, bromine or iodine, in the presence of a radical initiator, such as benzoyl peroxide, in a suitable solvent, such as carbon tetrachloride, and optionally in the presence of a light source, such as a 500 watt tungsten halogen lamp, at reflux.

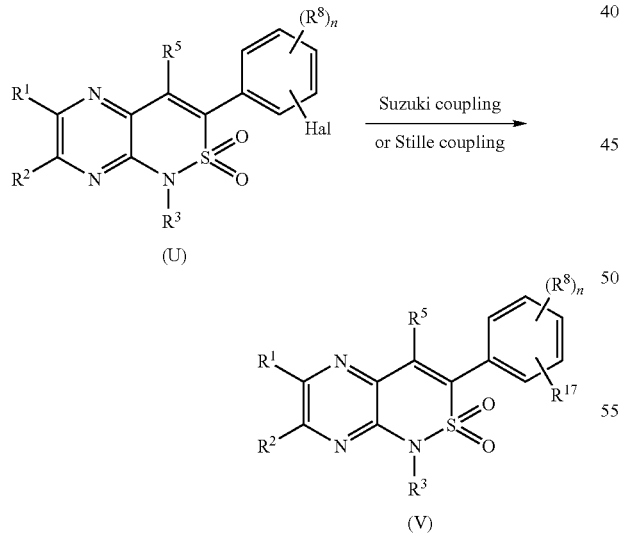

15) Compounds of formula (V) wherein $R^1$, $R^2$, $R^5$, and $R^8$ are as defined for a compound of formula (I), $R^3$ is defined as for a compound of formula (I), n is 0 to 4, and $R^{17}$ is aryl or aryl substituted by one to three $R^{13}$, which may be the same or different, or heteroaryl or heteroaryl substituted by one to three $R^{13}$, which may be the same or different, can be made from compounds of formula (U) wherein $R^1$, $R^2$, $R^5$, and $R^8$ are as defined for a compound of formula (I), $R^3$ is defined as for a compound of formula (I), n is 0 to 4, and Hal is chlorine, bromine or iodine, using a Suzuki coupling with a boronic acid of the formula $R^{17}B(OH)_2$ or a Stille coupling with a tin compound of the formula $R^{17}Sn(R^{18})_3$ wherein $R^{18}$ is $C_1$-$C_6$alkyl as shown in Scheme 7. The Suzuki coupling is typically carried out in the presence of a palladium catalyst, such as palladium(II) acetate, in the presence of a ligand, such as 2'-dicyclohexylphosphino-2,6-dimethoxy-3-sulfonato-1,1'-biphenyl hydrate sodium salt ("sodium S-Phos sulfonate"), in the presence of a base, such as potassium phosphate, in a suitable solvent, such as a mixture of toluene and water, at a temperature range from 50° C. to 150° C., preferably from 100° C. to 120° C., optionally using microwave heating. The Stille coupling is typically carried out in the presence of a palladium catalyst, such as palladium(II) chloride, in the presence of a ligand, such as tri-tert-butylphosphine, in a suitable solvent, such as N,N-dimethylformamide or acetonitrile, at temperature range from 20° C. to 150° C., preferably from 75° C. to 120° C.

Scheme 8

16) Compounds of formula (2) wherein $R^3$ and $R^4$ are as defined for a compound of formula (I) can be prepared by reaction of an amine of formula (1) wherein $R^3$ is as defined for a compound of formula (I) with an acid derivative of formula (G) as defined in 2) as shown in Scheme 8. For example, if (G) is a sulfonyl chloride (i.e. where X is chlorine) the reaction can conveniently be carried out in the presence of a base, such as triethylamine or pyridine, in a suitable solvent, such as acetonitrile or dichloromethane, optionally using microwave heating. Amines of formula (1) are commercially available or can be made by methods known to the person skilled in the art.

17) Compounds of formula (D) as defined in 5) can be prepared by reaction of a sulfonamide derivative of formula (2) as defined in 1) with a chloropyrazine ester of formula (3) wherein $R^1$ and $R^2$ are as defined for a compound of formula (I) and $R^{16}$ is as defined in 3). The reaction can conveniently be carried out in the presence of a base, such as potassium carbonate, in a suitable solvent, such as N,N-dimethylformamide, optionally using microwave heating. Compounds of formula (3) can be made by methods known to the person skilled in the art, particularly following Molbank 2002, M287 (see http://www.mdpi.org/molbank).

isilazide, sodium hexamethyldisilazide or potassium carbonate, in a suitable solvent, such as tetrahydrofuran or N,N-dimethylformamide, optionally using microwave heating.

21) Compounds of formula (8) wherein $R^1$, $R^2$ and $R^3$ are as defined for a compound of formula (I) can be made by hydrolysis and decarboxylation of a compound of formula (7) as defined in 20) by treatment with strong aqueous acid, such

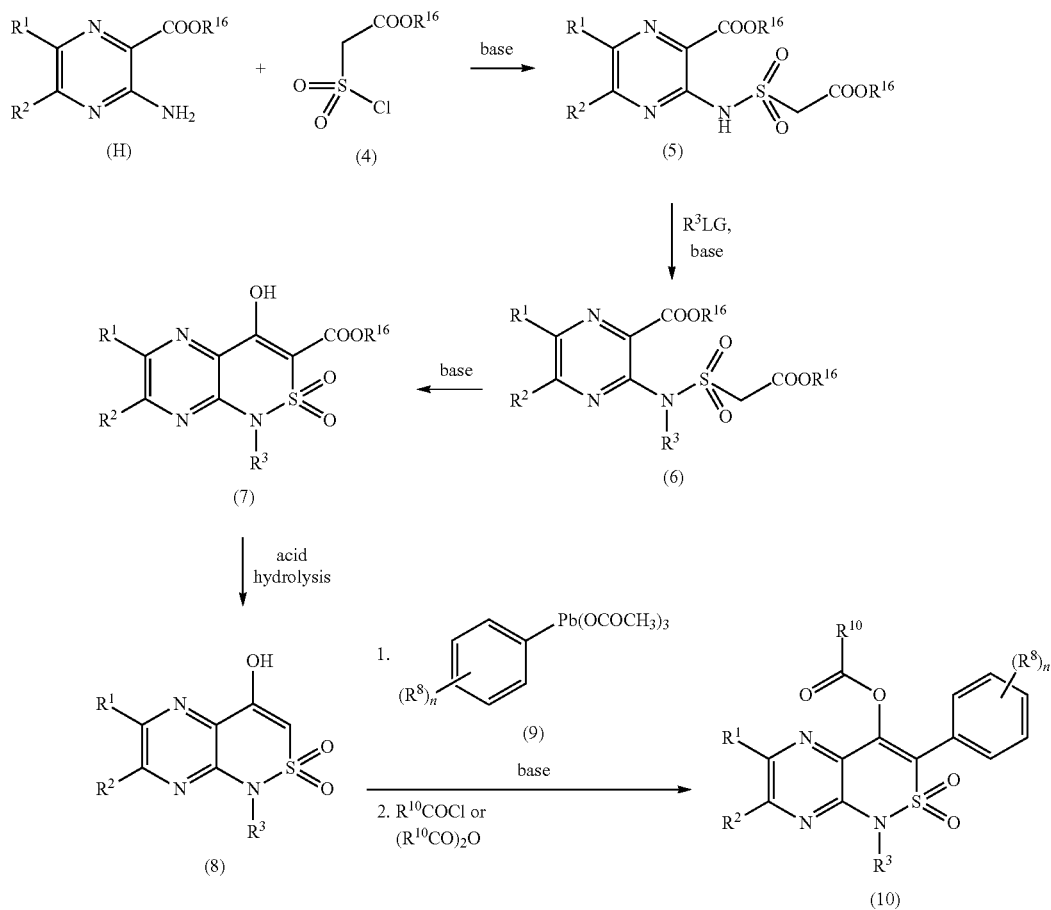

Scheme 9

18) Compounds of formula (5) wherein $R^1$ and $R^2$ are as defined for a compound of formula (I) and $R^{16}$ is as defined in 3) can be made by reaction of an aminopyrazine ester of formula (H) as defined in 3) with a sulfo-acetic ester of formula (4) wherein $R^{16}$ is as defined in 3), in the presence of a base, such as pyridine, in a suitable solvent, such as dichloromethane, as shown in Scheme 9. Sulfo-acetic esters of formula (4) can be made by methods known to the person skilled in the art.

19) Compounds of formula (6), wherein $R^1$, $R^2$ and $R^3$ are as defined for a compound of formula (I) and $R^{16}$ is as defined in 3) can be prepared from a compound of formula (5) as defined in 18) by reaction with a compound of formula $R^3LG$ as defined in 4), in the presence of a base, such as N,N-diisopropylethylamine, in a suitable solvent, such as acetonitrile, optionally using microwave heating.

20) Compounds of formula (7), wherein $R^1$, $R^2$ and $R^3$ are as defined for a compound of formula (I) and $R^{16}$ is as defined in 3), can be prepared by treating a compound of formula (6) as defined in 19) with a base, such as lithium hexamethyldas concentrated hydrochloric acid, or alternatively by treatment with dilute aqueous acid, such as aqueous hydrochloric acid, in a suitable solvent, such as ethanol, optionally using microwave heating.

22) Compounds of formula (10) wherein $R^1$, $R^2$, $R^3$, $R^8$ and $R^{10}$ are as defined for a compound of formula (I) can be made by reaction of a compound of formula (8) as defined in 21) with a lead compound of formula (9) wherein $R^8$ is as defined for a compound of formula (I) and n is 0 to 5, in the presence of a base, such as 4-dimethylaminopyridine, and in a suitable solvent, such as chloroform or toluene, followed by addition of an acid chloride of formula $R^{10}COCl$ or an acid anhydride of formula $(R^{10}CO)_2O$ wherein $R^{10}$ is as defined for a compound of formula (I). Lead compounds of formula (9) are known from the literature and can be made by the methods of J. T. Pinhey, B. A. Rowe, Aust. J. Chem., 1979, 32, 1561-6; J. Morgan, J. T. Pinhey, S. Chem. Soc. Perkin Trans. 1; 1990, 3, 715-20).

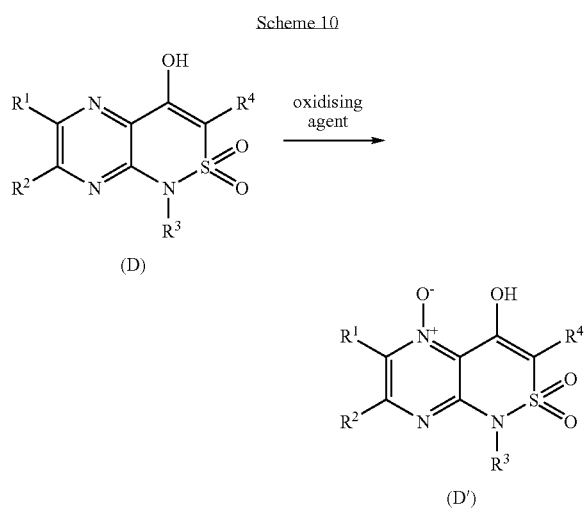

Scheme 10

(D)

(D')

23) N-oxides of formula (D'), i.e. compounds of formula (D) wherein the 5-nitrogen is oxidised, can be made by reaction of a compound of formula (D) as defined in 5), with an oxidising agent, for example a per-acid, such as trifluoroperacetic acid, generated in situ for example by adding trifluoroacetic anhydride to urea hydrogen peroxide, in a suitable solvent, such as dichloromethane, as shown in Scheme 10.

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilizers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be, formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octa-decanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is, given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-Trate®, to be added to the spray mixture as action-enhancing agent.

The herbicidal compositions generally comprise from 0.1 to 99% by weight, especially from 0.1 to 95% by weight, compounds of formula (I) and from 1 to 99.9% to by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |

-continued

Granules:

| | |
|---|---|
| active ingredient: | 0.1 to 30%, preferably 0.1 to 15% |
| solid carrier: | 99.5 to 70%, preferably 97 to 85% |

The following Examples further illustrate, but do not limit, the invention.

Formulation Examples for Herbicides of Formula (I) (%=% by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention relates to a method of controlling plants which comprises applying to the plants or to the locus thereof a herbicidally effective amount of a compound of formula (I).

The invention also relates to a method of inhibiting plant growth which comprises applying to the plants or to the locus thereof a herbicidally effective amount of a compound of formula (I).

The invention also relates to a method of selectively controlling grasses and weeds in crops of useful plants which comprises applying to the useful plants or locus thereof or to the area of cultivation a herbicidally effective amount of a compound of formula (I).

Crops of useful plants in which the composition according to the invention can be used include perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals and vegetables, especially cereals, maize and soy beans.

The grasses and weeds to be controlled may be both monocotyledonous species, for example *Agrostis, Alopecurus, Avena, Bromus, Cyperus, Digitaria, Echinochloa, Lolium, Monochoria, Rottboellia, Sagittaria, Scirpus, Setaria, Sida* and *Sorghum*, and dicotyledonous species, for example *Abutilon, Amaranthus, Chenopodium, Chrysanthemum, Galium, Ipomoea, Nasturtium, Sinapis, Solanum, Stellaria, Veronica, Viola* and *Xanthium*.

Crops are to be understood as also including those crops which have been rendered tolerant to herbicides or classes of herbicides (e.g. auxins or ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgarde® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Areas under cultivation include land on which the crop plants are already growing and land intended for cultivation with those crop plants. The compounds of the invention can be applied before weeds emerge (pre-emergence application) or after weeds emerge (post-emergence application), and are particularly effective when applied post-emergence.

The compounds of formula (I) according to the invention can also be used in combination with one or more further herbicides. In particular, the following mixtures of the compound of formula (I) are important:

Mixtures of a compound of formula (I) with a synthetic auxin (e.g. compound of formula (I)+clopyralid (162), compound of formula (I)+2,4-D (211), compound of formula (I)+dicamba (228), compound of formula (I)+diphenamid (274), compound of formula (I)+MCPA (499), compound of formula (I)+quinclorac (712), or compound of formula (I)+aminopyralid (CAS RN 150114-71-9)).

Mixtures of a compound of formula (I) with diflufenzopyr (252).

Mixtures of a compound of formula (I) with an acetanilide (e.g. compound of formula (I)+acetochlor (5), compound of formula (I)+dimethenamid (260), compound of formula (I)+metolachlor (548), compound of formula (I)+S-metolachlor (549), or compound of formula (I)+pretilachlor (656)).

Mixtures of a compound of formula (I) with flamprop-M (355).

Mixtures of a compound of formula (I) with flufenacet (BAY FOE 5043) (369).

Mixtures of a compound of formula (I) with pyroxasulfone (CAS RN 447399-55-5).

Mixtures of a compound of formula (I) with an HPPD inhibitor (e.g. compound of formula (I)+isoxaflutole (479), compound of formula (I)+mesotrione (515), compound of formula (I)+pyrasulfotole (CAS RN 365400-11-9), compound of formula (I)+sulcotrione (747), compound of formula (I)+tembotrione (CAS RN 335104-84-2), compound of formula (I)+topramezone (CAS RN 210631-68-8), compound of formula (I)+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), or compound of formula (I)+4-hydroxy-3-[[2-(3-methoxypropyl)-6-(difluoromethyl)-3-pyridinyl]carbonyl]-bicyclo[3.2.1]oct-3-en-2-one (CAS RN 894355-80-7)).

Mixtures of a compound of formula (I) with a triazine (e.g. compound of formula (I)+atrazine (37), or compound of formula (I)+terbuthylazine (775)).

Mixtures of a compound of formula (I) with a triazine and an HPPD inhibitor (e.g. compound of formula (I)+triazine+isoxaflutole, compound of formula (I)+triazine+mesotrione, compound of formula (I)+triazine+pyrasulfotole, compound of formula (I)+triazine+sulcotrione, compound of formula (I)+triazine+tembotrione, compound of formula (I)+triazine+topramezone, compound of formula (I)+triazine+4-hydroxy-3-[[2-[(2-methoxyethoxy)methyl]-6-(trifluoromethyl)-3-pyridinyl]carbonyl]-bicyclo[3.2.1]oct-3-en-2-one, or compound of formula (I)+triazine+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with glyphosate (419).

Mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+4-hydroxy-3-[[2-[(2-methoxyethoxy)methyl]-6-(trifluoromethyl)-3-pyridinyl]carbonyl]-bicyclo[3.2.1]oct-3-en-2-one, or compound of formula (I)+ glyphosate+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with glufosinate-ammonium (418).

Mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+4-hydroxy-3-[[2-[(2-methoxyethoxy)methyl]-6-(trifluoromethyl)-3-pyridinyl]carbonyl]-bicyclo[3.2.1]oct-3-en-2-one, or compound of formula (I)+glufosinate-ammonium+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with an ALS or an AHAS inhibitor (e.g. compound of formula (I)+bensulfuron-methyl (64), compound of formula (I)+chlorimuron-ethyl (135), compound of formula (I)+cloransulam-methyl (164), compound of formula (I)+florasulam (359), compound of formula (I)+flucarbazone-sodium (364), compound of formula (I)+imazamox (451), compound of formula (I)+imazapyr (453), compound of formula (I)+imazethapyr (455), compound of formula (I)+iodosulfuron-methyl-sodium (466), compound of formula (I)+mesosulfuron-methyl (514), compound of formula (I)+nicosulfuron (577), compound of formula (I)+penoxsulam (622), compound of formula (I)+pyroxsulam (triflosulam) (CAS RN 422556-08-9), compound of formula (I)+thifensulfuron-methyl (thiameturon-methyl) (795), compound of formula (I)+triasulfuron (817), compound of formula (I)+tribenuron-methyl (822), compound of formula (I)+trifloxysulfuron-sodium (833), compound of formula (I)+thiencarbazone (4-[(4,5-dihydro-3-methoxy-4-methyl-5-oxo-1H-1,2,4-triazol-1-yl)carbonylsulfamoyl]-5-methylthiophene-3-carboxylic acid, BAY636)), or compound of formula (I)+thiencarbazone-methyl(methyl 4-[(4,5-dihydro-3-methoxy-4-methyl-5-oxo-1H-1,2,4-triazol-1-yl)carbonylsulfamoyl]-5-methylthiophene-3-carboxylate, CAS RN 317815-83-1, BAY636-methyl)).

Mixtures of a compound of formula (I) with a PPO inhibitor (e.g. compound of formula (I)+acifluorfen-sodium (7), compound of formula (I)+butafenacil (101), compound of formula (I)+carfentrazone-ethyl (121), compound of formula (I)+cinidon-ethyl (152), compound of formula (I)+flumioxazin (376), compound of formula (I)+fomesafen (401), compound of formula (I) lactofen (486), or compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Mixtures of a compound of formula (I) with an ACCase inhibitor (e.g. compound of formula (I)+butroxydim (106), compound of formula (I)+clethodim (155), compound of formula (I)+clodinafop-propargyl (156), compound of formula (I)+cycloxydim (190), compound of formula (I)+cyhalofop-butyl (195), compound of formula (I)+diclofop-methyl (238), compound of formula (I)+fenoxaprop-P-ethyl (339), compound of formula (I)+fluazifop-butyl (361), compound of formula (I)+fluazifop-P-butyl (362), compound of formula (I)+haloxyfop (427), compound of formula (I)+haloxyfop-P (428), compound of formula (I)+propaquizafop (670), compound of formula (I)+quizalofop (717), compound of formula (I)+quizalofop-P (718), compound of formula (I)+sethoxydim (726), compound of formula (I)+tepraloxydim (771), compound of formula (I)+tralkoxydim (811)), or compound of formula (I)+pinoxaden (CAS RN 243973-20-8).

Mixtures of a compound of formula (I) with prosulfocarb (683), or a compound of formula (I) with tri-allate (816).

Mixtures of a compound of formula (I) with bromoxynil (95), a compound of formula (I) with chloridazon (134), a compound of formula (I) with chlorotoluron (143), a compound of formula (I) with diuron (281), or a compound of formula (I) with metribuzin (554).

Mixtures of a compound of formula (I) with clomazone (159), a compound of formula (I) with diflufenican (251), a compound of formula (I) with fluorochloridone (389), or a compound of formula (I) with flurtamone (392).

Mixtures of a compound of formula (I) with pendimethalin (621) or a compound of formula (I) with trifluralin (836).

Mixtures of a compound of formula (I) with difenzoquat metilsulfate (248).

Mixtures of a compound of formula (I) with diquat dibromide (276).

Mixtures of a compound of formula (I) with paraquat dichloride (614).

The mixing partners of the compound of formula (I) may also be in the form of esters or salts, as mentioned e.g. in The Pesticide Manual, 13$^{th}$ Edition (BCPC), 2003. The reference to glufosinate-ammonium also applies to glufosinate, the reference to cloransulam-methyl also applies to cloransulam, the reference to dimethenamid also applies to dimethenamid-P, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

Additionally, one or more of the following herbicides or plant growth regulators can be used in combination with a compound of formula (I) according to the invention or in combination with a mixture as described above: aclonifen (8), acrolein (10), alachlor (14), alloxydim (18), ametryn (20), amicarbazone (21), amidosulfuron (22), aminocyclopyrachlor (CAS RN 858956-08-8), amitrole (aminotriazole) (25), ammonium sulfamate (26), anilofos (31), asulam (36), aviglycine (39), azafenidin (CAS RN 68049-83-2), azimsulfuron (43), BAS 800H (CAS RN 372137-35-4), beflubutamid (55), benazolin (57), bencarbazone (CAS RN 173980-17-1), benfluralin (59), benfuresate (61), bensulide (65), bentazone (67), benzfendizone (CAS RN 158755-95-4), benzobicyclon (69), benzofenap (70), bilanafos (bialaphos) (77), bispyribac-sodium (82), borax (86), bromacil (90), bromobutide (93), bromofenoxim (CAS RN 13181-17-4), butachlor (100), butamifos (102), butralin (105), butylate (108), cafenstrole (110), carbetamide (117), chlorbromuron (CAS RN 13360-45-7), chlorflurenol-methyl (133), chloroacetic acid (138), chlorpropham (144), chlorsulfuron (147), chlorthal-dimethyl (148), cinmethylin (153), cinosulfuron (154), clomeprop (160), cumyluron (180), cyanamide (182), cyanazine (183), cyclanilide (186), cycloate (187), cyclosulfamuron (189), daimuron (213), dalapon (214), dazomet (216), desmedipham (225), desmetryn (CAS RN 1014-69-3), dichlobenil (229), dichlorprop (234), dichlorprop-P (235), diclosulam (241), dimefuron (256), dimepiperate (257), dimethachlor (258), dimethametryn (259), dimethipin (261), dimethylarsinic acid (264), dinitramine (268), dinoterb (272), dipropetryn (CAS RN 4147-51-7), dithiopyr (280), DNOC (282), DSMA (CAS RN 144-21-8), endothal (295), EPTC (299), esprocarb (303), ethalfluralin (305), ethametsulfuronmethyl (306), ethephon (307), ethofumesate (311), ethoxyfen (CAS RN 188634-90-4), ethoxyfen-ethyl (CAS RN 131086-42-5), ethoxysulfuron (314), etobenzanid (318), fentrazamide (348), ferrous sulfate (353), flazasulfuron (356), fluazolate (isopropazol) (CAS RN 174514-07-9), flucetosulfuron (CAS RN 412928-75-7), fluchloralin (365), flufenpyr-ethyl (371), flumetralin (373), flumetsulam (374), flumiclorac-pentyl (375), flumipropyn (flumipropin) (CAS RN 84478-52-4), flu-ometuron (378), fluoroglycofenethyl (380), flupoxam (CAS RN 119126-15-7), flupropacil (CAS RN 120890-70-2), flu-propanate (383), flupyrsulfuron-methyl-sodium (384), flure-nol (387), fluridone (388), fluoroxypyr (390), fluthiacet-methyl (395), foramsulfuron (402), fosamine (406), halosulfuron-methyl (426), HC-252 (429), hexazinone (440), imazamethabenz-methyl (450), imazapic (452), imazaquin (454), imazosulfuron (456), indanofan (462), ioxynil (467), isoproturon (475), isouron (476), isoxaben (477), isoxachlortole (CAS RN 141112-06-3), isoxapyrifop (CAS RN 87757-18-4), karbutilate (482), lenacil (487), linuron (489), MCPA-thioethyl (500), MCPB (501), mecoprop (503), mecoprop-P (504), mefenacet (505), mefluidide (507), metam (519), metamifop (mefluoxafop) (520), metamitron (521), metazachlor (524), methabenzthiazuron (526), methazole (CAS RN 20354-26-1), methylarsonic acid (536), 1-methylcyclopropene (538), methyldymron (539), methyl isothiocyanate (543), metobenzuron (547), metobromuron (CAS RN 3060-89-7), metosulam (552), metoxuron (553), metsulfuron-methyl (555), MK-616 (559), molinate (560), monolinuron (562), MSMA (CAS RN 2163-80-6), napronilide (571), napropamide (572), naptalam (573), neburon (574), nipyraclofen (CAS RN 99662-11-0), n-methyl-glyphosate, nonanoic acid (583), norflurazon (584), oleic acid (fatty acids) (593), orbencarb (595), orthosulfamuron (CAS RN 213464-77-8), oryzalin (597), oxadiargyl (599), oxadiazon (600), oxasulfuron (603), oxaziclomefone (604), oxyfluorfen (610), pebulate (617), pentachlorophenol (623), pentanochlor (624), pentoxazone (625), pethoxamid (627), petrolium oils (628), phenmedipham (629), picloram (645), picolinafen (646), piperophos (650), primisulfuron-methyl (657), prodiamine (661), profluazol (CAS RN 190314-43-3), profoxydim (663), prohexadione calcium (664), prometon (665), prometryn (666), propachlor (667), propanil (669), propazine (672), propham (674), propisochlor (667), propoxycarbazone-sodium (procarbazone-sodium) (679), propyzamide (681), prosulfuron (684), pyraclonil (pyrazogyl) (CAS RN 158353-15-2), pyraflufen-ethyl (691), pyrazolynate (692), pyrazosulfuron-ethyl (694), pyrazoxyfen (695), pyribenzoxim (697), pyributicarb (698), pyridafol (CAS RN 40020-01-7), pyridate (702), pyriftalid (704), pyriminobac-methyl (707), pyrimisulfan (CAS RN 221205-90-9), pyrithiobac-sodium (709), quinmerac (713), quinoclamine (714), rimsulfuron (721), sequestrene, siduron (727), simazine (730), simetryn (732), sodium chlorate (734), sulfentrazone (749), sulfometuron-methyl (751), sulfosate (CAS RN 81591-81-3), sulfosulfuron (752), sulfuric acid (755), tar oils (758), TCA-sodium (760), tebutam (CAS RN 35256-85-0), tebuthiuron (765), tefuryltrione (CAS RN 473278-76-1), terbacil (772), terbumeton (774), terbutryn (776), thenylchlor (789), thidiazimin (CAS RN 123249-43-4), thiazafluoron (CAS RN 25366-23-8), thiazopyr (793), thiobencarb (797), tiocarbazil (807), triaziflam (819), triclopyr (827), trietazine (831), triflusulfuron-methyl (837), trihydroxytriazine (CAS RN 108-80-5), trinexapac-ethyl (CAS RN 95266-40-3), tritosulfuron (843), N-[(1R,2S)-2,6-dimethyl-2,3-dihydro-1H-inden-1-yl]-6-(1-fluoroethyl)-1,3,5-triazine-2,4-diamine (CAS RN 950782-86-2), 1-(2-chloro-6-propylimidazo[1,2-b]pyridazin-3-ylsulfonyl)-3-(4,6-dimethoxypyrimidin-2-yl)urea (CAS RN 570415-88-2), and 5-(2,6-difluoro-benzyloxymethyl)-5-methyl-3-(3-methyl-thiophen-2-yl)-4,5-dihydro-isoxazole (CAS RN 403640-27-7).

The mixing partners of the compound of formula (I) may also be in the form of esters or salts, as mentioned e.g. in The Pesticide Manual, 13$^{th}$ Edition (BCPC), 2003. The reference to acifluorfen-sodium also applies to acifluorfen, and the reference to bensulfuron-methyl also applies to bensulfuron, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further herbicides can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. The safeners can be AD-67 (11), benoxacor (63), cloquintocet-mexyl (163), cyometrinil (CAS RN 78370-21-5), cyprosulfamide (CAS RN 221667-31-8), dichlormid (231), dicyclonon (CAS RN 79260-71-2), fenchlorazole-ethyl (331), fenclorim (332), flurazole (386), fluxofenim (399), furilazole (413) and the corresponding R isomer, isoxadifen-ethyl (478), mefenpyr-diethyl (506), 2-methoxy-N-[[4-[[methylamino)carbonyl]amino]-phenyl]sulfonyl]-benzamide (CAS RN 129531-12-0), naphthalic anhydride (CAS RN 81-84-5), and oxabetrinil (598). Particularly preferred are mixtures of a compound of formula (I) with benoxacor and a compound of formula (I) with cloquintocet-mexyl.

The safeners of the compound of formula (I) may also be in the form of esters or salts, as mentioned e.g. in The Pesticide Manual, 13$^{th}$ Edition (BCPC), 2003. The reference to cloquintocet-mexyl also applies to cloquintocet, and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) with the safener). It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with florasulam and a safener, particularly cloquintocet-mexyl.

Mixtures of a compound of formula (I) with clodinafop-propargyl and a safener, particularly cloquintocet-mexyl.

Mixtures of a compound of formula (I) with pinoxaden and a safener, particularly cloquintocet-mexyl.

Mixtures of a compound of formula (I) with bromoxynil and a safener, particularly cloquintocet-mexyl.

The following Examples further illustrate, but do not limit, the invention.

PREPARATION EXAMPLES

1. Reactions that are Covered by Scheme 1

Some methanesulfonyl chlorides are commercially available, for example, (2-bromo-phenyl)-methanesulfonyl chloride, (2-cyano-phenyl)-methanesulfonyl chloride, (2,4-dichloro-5-fluoro-phenyl)-methanesulfonyl chloride, (3,4-dichloro-phenyl)-methanesulfonyl chloride, (2-nitro-phenyl)-methanesulfonyl chloride, (2-trifluoromethyl-phenyl)-methanesulfonyl chloride and (3-trifluoromethyl-phenyl)-methanesulfonyl chloride. Other methanesulfonyl chlorides were made using the methods according to Example 1.1-Example 1.4 below.

Example 1.1

Preparation of sodium (2-chloro-5-trifluoromethyl-phenyl)-methane-sulfonic acid

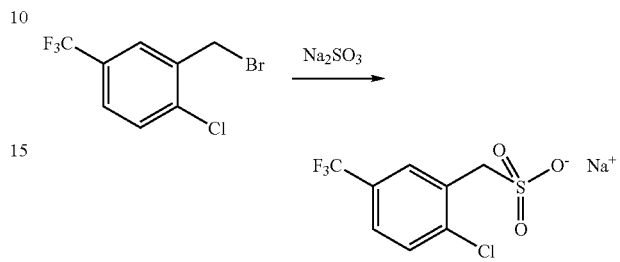

To a solution of 2-chloro-5-trifluoromethyl-benzyl bromide (10 g) in acetone (20 ml) was added a solution of sodium sulfite (4.9 g) in water (20 ml). The reaction mixture was heated to reflux for 3 hours. The reaction mixture was concentrated. The residue was recrystallised from acetone to give sodium (2-chloro-5-trifluoromethyl-phenyl)-methane-sulfonic acid as an off white solid (9.652 g). 1H-NMR (400 MHz, $d_6$-DMSO): 7.89 (m, 1H), 7.58-7.65 (m, 2H), 3.98 (s, 2H) ppm.

The following compounds were made using the same method:

Sodium (2,5-bis-(trifluoromethyl)-phenyl)-methane-sulfonic acid. 1H-NMR (400 MHz, $d_6$-DMSO): 8.15 (d, 1H), 7.73-7.98 (m, 2H), 3.93 (s, 2H) ppm.

Sodium (2,6-bis-(trifluoromethyl)-phenyl)-methane-sulfonic acid. 1H-NMR (400 MHz, $d_6$-DMSO): 7.97 (d, 2H), 7.63-7.67 (m, 1H), 4.26 (s, 2H) ppm.

Sodium (3-bromo-2-chloro-6-fluoro-phenyl)-methane-sulfonic acid. 1H-NMR (400 MHz, $d_6$-DMSO): 7.67-7.69 (m, 1H), 7.14-7.17 (m, 1H), 4.01 (s, 2H) ppm.

Sodium (2-bromo-5-trifluoromethyl-phenyl)-methane-sulfonic acid. 1H-NMR (400 MHz, $d_6$-DMSO): 7.84 (d, 1H), 7.73-7.75 (m, 1H), 7.42-7.45 (dd, 1H), 3.95 (s, 2H) ppm.

Sodium (2-chloro-3,6-difluoro-phenyl)-methanesulfonic acid. The crude compound was used directly for further synthesis.

Sodium (2-chloro-6-fluoro-3-methoxy-phenyl)-methane-sulfonic acid. The crude compound was used directly for further synthesis.

Sodium (2-chloro-6-fluoro-3-methyl-phenyl)-methane-sulfonic acid. The crude compound was used directly for further synthesis.

Sodium (2-chloro-5-iodo-phenyl)-methanesulfonic acid. 1H-NMR (400 MHz, $d_6$-DMSO): 7.87 (d, 1H), 7.54-7.57 (dd, 1H), 7.18 (d, 1H), 3.84 (s, 2H) ppm.

Sodium (2-chloro-quinolin-3-yl)-methanesulfonic acid. The crude compound was used directly for further synthesis.

Sodium (2-chloro-3-trifluoromethyl-phenyl)-methane-sulfonic acid. 1H-NMR (400 MHz, $d_6$-DMSO): 7.83 (d, 1H), 7.72 (d, 1H), 7.47 (t, 1H), 4.01 (s, 2H) ppm.

Sodium (2-chloro-6-trifluoromethyl-phenyl)-methane-sulfonic acid. 1H-NMR (400 MHz, $d_6$-DMSO): 7.65-7.67 (d, 1H), 7.57-7.59 (d, 1H), 7.35-7.39 (t, 1H), 4.15 (s, 2H) ppm.

Sodium (4-chloro-2-trifluoromethyl-phenyl)-methane-sulfonic acid. 1H-NMR (400 MHz, $d_6$-DMSO): 7.83-7.86 (dd, 1H), 7.43 (d, 1H), 7.32-7.34 (d, 1H), 4.05 (s, 2H) ppm.

Sodium (2,6-dibromo-phenyl)-methanesulfonic acid. 1H-NMR (400 MHz, d$_6$-DMSO): 7.59 (d, 2H), 7.05 (t, 1H), 4.21 (s, 2H) ppm.

Sodium (2,3-dichloro-6-fluoro-phenyl)-methanesulfonic acid. The crude compound was used directly for further synthesis.

Sodium (2,4-dichloro-5-fluoro-phenyl)-methanesulfonic acid. 1H-NMR (400 MHz, d$_6$-DMSO): 7.73 (d, 1H), 7.55 (d, 1H), 3.88 (s, 2H) ppm.

Sodium (2,3-dichloro-phenyl)-methanesulfonic acid. 1H-NMR (400 MHz, d$_6$-DMSO): 7.43-7.45 (m, 2H), 7.23 (t, 1H), 3.92 (s, 2H) ppm.

Sodium (2,6-dichloro-phenyl)-methanesulfonic acid. The crude compound was used directly for further synthesis.

Sodium (2,5-dichloro-6-trifluoromethyl-phenyl)-methanesulfonic acid. 1H-NMR (400 MHz, d$_6$-DMSO): 7.74 (d, 1H), 7.67 (d, 1H), 4.29 (s, 2H) ppm.

Sodium (2-fluoro-6-trifluoromethyl-phenyl)-methanesulfonic acid. 1H-NMR (400 MHz, d$_6$-DMSO): 7.39-7.44 (m, 3H), 3.94 (s, 2H) ppm.

Sodium (2-iodo-phenyl)-methanesulfonic acid. 1H-NMR (400 MHz, d$_5$-DMSO): 7.71-7.74 (dd, 1H), 7.48-7.51 (dd, 1H), 7.22-7.26 (dt, 1H), 6.86-6.90 (dt, 1H), 3.85 (s, 2H) ppm.

Sodium (2,3,6-trichloro-phenyl)-methanesulfonic acid. 1H-NMR (400 MHz, d$_6$-DMSO): 7.50 (d, 1H), 7.43 (d, 1H), 4.20 (s, 2H) ppm.

Sodium (2-trifluoromethoxy-phenyl)-methanesulfonic acid. The crude compound was used directly for further synthesis.

Sodium (2-trifluoromethylthio-phenyl)-methanesulfonic acid. The crude compound was used directly for further synthesis.

Example 1.2

Preparation of (2-chloro-5-trifluoromethyl-phenyl)-methanesulfonyl chloride

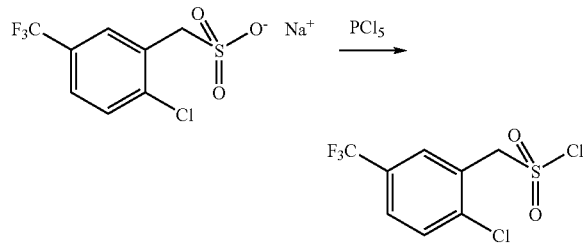

A mixture of sodium (2-chloro-5-trifluoromethyl-phenyl)-methanesulfonic acid (Example 1.1) (9.4 g) and phosphorous pentachloride (13.5 g) was heated to 80-90° C. for 4 hours. The reaction mixture was concentrated. The residue was poured onto a mixture of ice and water and the mixture extracted twice with dichloromethane. The combined organic extracts were washed with water and brine, dried over magnesium sulfate and concentrated to give (2-chloro-5-trifluoromethyl-phenyl)-methanesulfonyl chloride as an off-white solid (8.480 g). 1H-NMR (400 MHz, CDCl$_3$): 7.87 (m, 1H), 7.68 (m, 2H), 5.15 (s, 2H) ppm.

The following compounds were made using the same method:

(2,5-Bis-(trifluoromethyl)-phenyl)-methanesulfonyl chloride. 1H-NMR (400 MHz, CDCl$_3$): 8.08 (s, 1H), 7.96 (d, 1H), 7.89 (d, 1H), 5.18 (s, 2H) ppm.

(2,6-Bis-(trifluoromethyl)-phenyl)-methanesulfonyl chloride. 1H-NMR (400 MHz, CDCl$_3$): 8.05 (d, 2H), 7.78 (d, 1H), 5.63 (s, 2H) ppm.

(3-Bromo-2-chloro-6-fluoro-phenyl)-methanesulfonyl chloride. 1H-NMR (400 MHz, CDCl$_3$): 7.75-7.78 (m, 1H), 7.06-7.09 (m, 1H), 5.25 (s, 2H) ppm.

(2-Bromo-5-trifluoromethyl-phenyl)-methanesulfonyl chloride. 1H-NMR (400 MHz, CDCl$_3$): 7.84-7.87 (m, 2H), 7.58-7.61 (m, 1H), 5.18 (s, 2H) ppm.

(2-Chloro-3,6-difluoro-phenyl)-methanesulfonyl chloride. 1H-NMR (400 MHz, CDCl$_3$): 7.28-7.34 (m, 1H), 7.12-7.18 (m, 1H), 5.19 (s, 2H) ppm.

(2-Chloro-6-fluoro-3-methoxy-phenyl)-methanesulfonyl chloride. 1H-NMR (400 MHz, CDCl$_3$): 6.98-7.05 (m, 2H), 5.22 (s, 2H), 3.92 (s, 3H) ppm.

(2-Chloro-6-fluoro-3-methyl-phenyl)-methanesulfonyl chloride. 1H-NMR (400 MHz, CDCl$_3$): 7.34-7.37 (m, 1H), 7.04-7.07 (m, 1H), 5.23 (s, 2H), 2.41 (s, 3H) ppm.

(2-Chloro-5-iodo-phenyl)-methanesulfonyl chloride. 1H-NMR (400 MHz, CDCl$_3$): 7.90 (d, 1H), 7.72-7.74 (dd, 1H), 7.25 (d, 1H), 5.03 (s, 2H) ppm.

(2-Chloro-quinolin-3-yl)-methanesulfonyl chloride. 1H-NMR (400 MHz, CDCl$_3$): 8.45 (s, 1H), 8.07 (d, 1H), 7.91 (d, 1H), 7.85 (dt, 1H), 7.66 (dt, 1H), 5.27 (s, 2H) ppm.

(2-Chloro-3-trifluoromethyl-phenyl)-methanesulfonyl chloride. 1H-NMR (400 MHz, CDCl$_3$): 7.76 (d, 1H), 7.66 (d, 1H), 7.41 (t, 1H), 4.87 (s, 2H) ppm.

(2-Chloro-6-trifluoromethyl-phenyl)-methanesulfonyl chloride. 1H-NMR (400 MHz, CDCl$_3$): 7.75-7.77 (d, 1H), 7.73-7.75 (d, 1H), 7.53-7.58 (t, 1H), 5.55 (s, 2H) ppm.

(4-Chloro-2-trifluoromethyl-phenyl)-methanesulfonyl chloride. 1H-NMR (400 MHz, CDCl$_3$): 7.76-7.78 (d, 1H), 7.74 (s, 1H), 7.63-7.65 (d, 1H), 5.10 (s, 2H) ppm.

(2,6-Dibromo-phenyl)-methanesulfonyl chloride. 1H-NMR (400 MHz, CDCl$_3$): 7.67 (d, 2H), 7.17 (t, 1H), 5.55 (s, 2H) ppm.

(2,3-Dichloro-6-fluoro-phenyl)-methanesulfonyl chloride. 1H-NMR (400 MHz, CDCl$_3$): 7.59-7.62 (m, 1H), 7.12-7.16 (m, 1H), 5.23 (s, 2H) ppm.

(2,4-Dichloro-5-fluoro-phenyl)-methanesulfonyl chloride. 1H-NMR (400 MHz, CDCl$_3$): 7.43 (d, 1H), 7.60 (d, 1H), 5.04 (s, 2H) ppm.

(2,3-Dichloro-phenyl)-methanesulfonyl chloride. 1H-NMR (400 MHz, CDCl$_3$): 7.51-7.61 (m, 2H), 7.32 (t, 1H), 5.16 (s, 2H) ppm.

(2,6-Dichloro-phenyl)-methanesulfonyl chloride. 1H-NMR (400 MHz, CDCl$_3$): 7.44-7.46 (m, 1H), 7.33-7.38 (m, 1H), 7.19-7.23 (m, 1H), 5.43 (s, 2H) ppm.

(2,5-Dichloro-6-trifluoromethyl-phenyl)-methanesulfonyl chloride. 1H-NMR (400 MHz, CDCl$_3$): 7.67 (d, 1H), 7.56 (d, 1H), 5.54 (s, 2H) ppm.

(2-Fluoro-6-trifluoromethyl-phenyl)-methanesulfonyl chloride. 1H-NMR (400 MHz, CDCl$_3$): 7.59-7.64 (m, 2H), 7.41-7.45 (m, 1H), 5.30 (s, 2H) ppm.

(2-Iodo-phenyl)-methanesulfonyl chloride. 1H-NMR (400 MHz, CDCl$_3$): 7.96-7.98 (m, 1H), 7.62-7.64 (m, 1H), 7.43-7.47 (m, 1H), 7.14-7.17 (m, 1H), 5.16 (s, 2H) ppm.

(2,3,6-Trichloro-phenyl)-methanesulfonyl chloride. 1H-NMR (400 MHz, CDCl$_3$): 7.54 (d, 1H), 7.41 (d, 1H), 5.47 (s, 2H) ppm.

(2-Trifluoromethoxy-phenyl)-methanesulfonyl chloride. 1H-NMR (400 MHz, CDCl$_3$): 7.61-7.63 (dd, 1H), 7.52-7.54 (dd, 1H), 7.38-7.40 (d, 2H), 4.99 (s, 2H) ppm.

(2-Trifluoromethylthio-phenyl)-methanesulfonyl chloride. 1H-NMR (400 MHz, CDCl₃): 7.88-7.90 (m, 1H), 7.71-7.73 (m, 1H), 7.55-7.65 (d, 2H), 5.30 (s, 2H) ppm.

Example 1.3

Preparation of thioacetic acid S-(4-bromo-2-trifluoromethyl-benzyl) ester

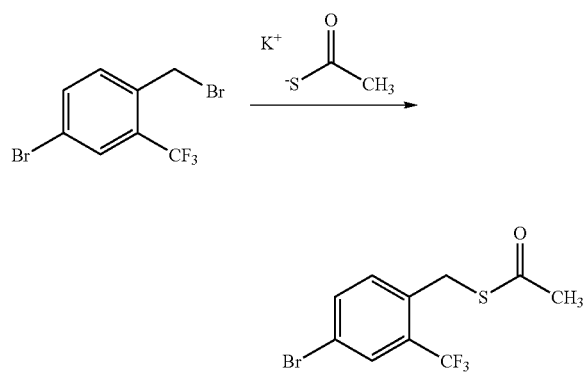

To a solution of 4-bromo-2-trifluoromethylbenzyl bromide (2.4 g) in acetone (20 ml) was added potassium thioacetate (1.04 g). The reaction mixture was heated to reflux for 4 hours. The reaction mixture was allowed to cool to ambient temperature and was then filtered through a plug of silica gel. Further acetone (30 ml) was passed through the silica gel (30 ml). The combined filtrate was concentrated to give thioacetic acid S-(4-bromo-2-trifluoromethyl-benzyl) ester as a dark liquid (2.275 g). 1H-NMR (400 MHz, CDCl₃): 7.75 (s, 1H), 7.60 (d, 1H), 7.42 (d, 1H), 4.25 (s, 2H), 2.36 (s, 3H) ppm.

The following compounds were made using the same method:

Thioacetic acid S-(2,4-bis-(trifluoromethyl)-benzyl) ester. 1H-NMR (400 MHz, CDCl₃): 7.88 (s, 1H), 7.69-7.76 (m, 2H), 4.34 (s, 2H), 2.38 (s, 3H) ppm.

Thioacetic acid S-(2-chloro-6-fluoro-5-methoxy-benzyl) ester. 1H-NMR (400 MHz, CDCl₃): 7.09-7.12 (dd, 1H), 6.83 (t, 1H), 4.32 (d, 2H), 3.87 (s, 3H), 2.35 (s, 3H), ppm.

Thioacetic acid S-(2-chloro-4-iodo-benzyl) ester. 1H-NMR (400 MHz, CDCl₃): 7.70 (d, 1H), 7.52 (s, 1H), 7.17 (d, 1H), 4.14 (s, 2H), 2.33 (s, 3H) ppm.

Thioacetic acid S-(3-chloro-5-trifluoromethyl-benzyl) ester. 1H-NMR (400 MHz, CDCl₃): 7.48 (m, 2H), 7.43 (s, 1H), 4.11 (s, 2H), 2.38 (s, 3H) ppm.

Thioacetic acid S-(5-chloro-2-trifluoromethyl-benzyl) ester. 1H-NMR (400 MHz, CDCl₃): 7.56 (d, 1H), 7.53 (s, 1H), 7.33 (d, 1H), 4.27 (s, 2H), 2.38 (s, 3H) ppm.

Thioacetic acid S-(2,3-dichloro-6-trifluoromethyl-benzyl) ester. The crude compound was used directly for further synthesis.

Thioacetic acid S-(3-ethoxycarbonyl-6-trifluoromethyl-pyrid-2-yl) ester. 1H-NMR (400 MHz, CDCl₃): 8.35 (d, 1H), 7.61 (d, 1H), 4.73 (s, 2H), 4.47 (q, 2H), 2.33 (s, 3H), 1.44 (t, 3H) ppm.

Thioacetic acid S-(5-methyl-2-trifluoromethyl-benzyl) ester. The crude compound was used directly for further synthesis.

Example 1.4

Preparation of (4-bromo-2-trifluoromethyl-phenyl)-methanesulfonyl chloride

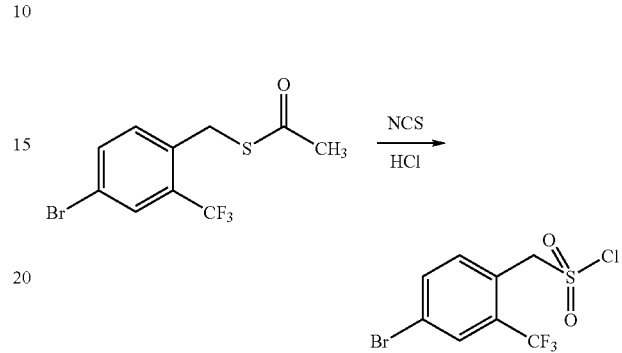

To a mixture of aqueous hydrochloric acid (2M) (2 ml) and acetonitrile (10 ml) was added N-chlorosuccinimide ("NCS") (3.9 g) in portions. To this mixture was added at 20-25° C. added drop wise a solution of thioacetic acid S-(4-bromo-2-trifluoromethyl-benzyl) ester (Example 1.3) (2.27 g) in acetonitrile (3 ml). It was necessary to control the temperature of the reaction by using an ice bath and regulating the addition rate of the thioacetic acid S-(4-bromo-2-trifluoromethyl-benzyl) ester. On completion of the addition the reaction mixture was stirred at ambient temperature for 30 minutes. The reaction mixture was partitioned between diethyl ether (50 ml) and aqueous sodium chloride (12% w/v) (20 ml). The organic layer was washed with further aqueous sodium chloride (12% w/v) (2×20 ml). The organic layer was concentrated, the residue absorbed onto silica gel and purified by column chromatography on silica (eluent: 1:1 dichloro-methane/iso-hexane) to give (4-bromo-2-trifluoromethyl-phenyl)-methanesulfonyl chloride as a yellow oil (2.225 g). 1H-NMR (400 MHz, CDCl₃): 7.94 (s, 1H), 7.81 (d, 1H), 7.68 (d, 1H), 5.08 (s, 2H) ppm.

The following compounds were made using the same method:

(2,4-Bis-(trifluoromethyl)-phenyl)-methanesulfonyl chloride. 1H-NMR (400 MHz, CDCl₃): 8.06 (s, 1H), 7.94-8.01 (m, 2H), 5.19 (s, 2H) ppm.

(2-Chloro-6-fluoro-5-methoxy-phenyl)-methanesulfonyl chloride. ¹H-NMR (400 MHz, CDCl₃): 7.25-7.28 (dd, 1H), 7.04 (t, 1H), 5.18 (s, 2H), 3.92 (s, 3H) ppm.

(2-Chloro-4-iodo-phenyl)-methanesulfonyl chloride. 1H-NMR (400 MHz, CDCl₃): 7.89 (d, 1H), 7.72 (d, 1H), 7.30 (d, 1H), 5.04 (s, 2H) ppm.

(3-Chloro-5-trifluoromethyl-phenyl)-methanesulfonyl chloride. 1H-NMR (400 MHz, CDCl₃): 7.75 (s, 1H), 7.69 (s, 1H), 7.65 (s, 1H), 4.88 (s, 2H) ppm.

(5-Chloro-2-trifluoromethyl-phenyl)-methanesulfonyl chloride. 1H-NMR (400 MHz, CDCl₃): 7.80 (s, 1H), 7.74 (d, 1H), 7.59 (s, 1H), 5.10 (s, 2H) ppm.

(2,3-Dichloro-6-trifluoromethyl-phenyl)-methanesulfonyl chloride. 1H-NMR (400 MHz, CDCl₃): 7.74 (s, 1H), 7.67 (d, 1H), 5.59 (s, 2H) ppm.

(3-Ethoxycarbonyl-6-trifluoromethyl-pyrid-2-yl)-methanesulfon-yl chloride. 1H-NMR (400 MHz, CDCl₃): 8.56 (d, 1H), 7.87 (d, 1H), 5.83 (s, 2H), 4.48 (q, 2H), 1.44 (t, 3H) ppm.

(5-Methyl-2-trifluoromethyl-phenyl)-methanesulfonyl chloride. 1H-NMR (400 MHz, CDCl$_3$): 7.67 (d, 1H), 7.58 (s, 1H), 7.39 (d, 1H), 5.11 (s, 2H), 2.47 (s, 31-1) ppm.

2. Reactions that are Covered by Scheme 2

Example 2.1

Preparation of 3-(2-chloro-5-trifluoromethyl-phenyl-methanesulfonyl-amino)-pyrazine-2-carboxylic acid methyl ester

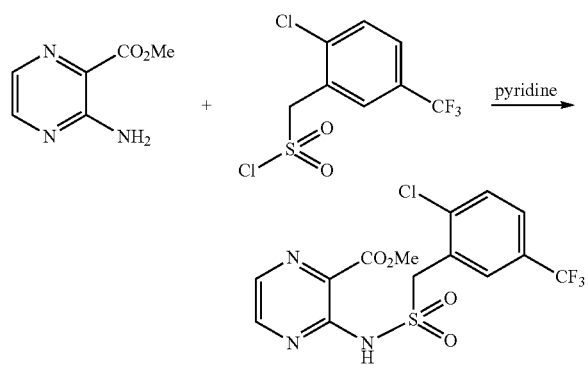

To a solution of 3-amino-pyrazine-2-carboxylic acid methyl ester (commercially available) (2.0 g) and (2-chloro-5-trifluoromethyl-phenyl)-methanesulfonyl chloride (Example 1.2) (4.2 g) in dichloromethane (32 ml) was added dropwise pyridine (5.3 ml) over a period of 5 minutes at ambient temperature. The reaction mixture was stirred at ambient temperature for 23 hours. Dichloromethane (50 ml) was added to the reaction mixture and the mixture was washed with aqueous sulfuric acid (2M) (3×30 ml). The phases were separated and the organic layer was concentrated. The residue was purified by column chromatography on silica gel (eluent: ethyl acetate/dichloromethane from 0:10 to 1:9) to give 3-(2-chloro-5-trifluoromethyl-phenyl-methanesulfonylamino)-pyrazine-2-carboxylic acid methyl ester as a white solid (4.728 g). 1H-NMR (400 MHz, CDCl$_3$): 10.30 (s, 1H), 8.59 (s, 1H), 8.47 (s, 1H), 7.77 (bs, 1H), 7.54-7.60 (m, 2H), 5.15 (s, 2H), 4.04 (s, 3H) ppm.

The following compounds were made using the same method:

3-(2,4-Bis-(trifluoromethyl)-phenylmethanesulfonylamino)-pyrazine-2-carboxylic acid methyl ester. 1H-NMR (400 MHz, CDCl$_3$): 10.40 (s, 1H), 8.56 (d, 1H), 8.48 (d, 1H), 7.98-8.01 (m, 2H), 7.88 (d, 1H), 5.21 (s, 2H), 4.06 (s, 3H) ppm.

3-(2,5-Bis-(trifluoromethyl)-phenylmethanesulfonylamino)-pyrazine-2-carboxylic acid methyl ester. 1H-NMR (400 MHz, CDCl$_3$): 10.40 (s, 1H), 8.57 (d, 1H), 8.48 (d, 1H), 8.06 (s, 1H), 7.88 (d, 1H), 7.79 (d, 1H), 5.20 (s, 2H), 4.06 (s, 3H) ppm.

3-(2,6-Bis-(trifluoromethyl)-phenylmethanesulfonylamino)-pyrazine-2-carboxylic acid methyl ester. 1H-NMR (400 MHz, CDCl$_3$): 10.36 (s, 1H), 8.58 (d, 1H), 8.47 (d, 1H), 8.00 (d, 2H), 7.69 (t, 1H), 5.45 (s, 2H), 4.06 (s, 3H) ppm.

3-(3-Bromo-2-chloro-6-fluoro-phenylmethanesulfonylamino)-pyrazine-2-carboxylic acid methyl ester. 1H-NMR (400 MHz, CDCl$_3$): 10.33 (bs, 1H), 8.58 (d, 1H), 8.45 (d, 1H), 7.65-7.67 (m, 1H), 6.95-6.98 (m, 1H), 5.23 (s, 2H), 4.05 (s, 3H) ppm.

3-(2-Bromo-phenylmethanesulfonylamino)-pyrazine-2-carboxylic acid methyl ester. 1H-NMR (400 MHz, CDCl$_3$): 10.23 (bs, 1H), 8.59 (d, 1H), 8.43 (d, 1H), 7.52-7.60 (m, 2H), 7.33-7.36 (m, 1H), 7.22-7.27 (m, 1H), 5.13 (s, 2H), 4.03 (s, 3H) ppm.

3-(2-Bromo-5-trifluoromethyl-phenylmethanesulfonylamino)-pyrazine-2-carboxylic acid methyl ester. 1H-NMR (400 MHz, CDCl$_3$): 10.31 (s, 1H), 8.59 (d, 1H), 8.47 (d, 1H), 7.74-7.76 (m, 2H), 7.48-7.51 (dd, 1H), 5.17 (s, 2H), 4.05 (s, 3H) ppm.

3-(4-Bromo-2-trifluoromethyl-phenylmethanesulfonylamino)-pyrazine-2-carboxylic acid methyl ester. 1H-NMR (400 MHz, CDCl$_3$): 10.34 (s, 1H), 8.55 (d, 1H), 8.46 (d, 1H), 7.85 (s, 1H), 7.74 (d, 1H), 7.68 (d, 1H), 5.10 (s, 2H), 4.05 (s, 3H) ppm.

3-(2-Chloro-3,6-difluoro-phenylmethanesulfonylamino)-pyrazine-2-carboxylic acid methyl ester. 1H-NMR (400 MHz, CDCl$_3$): 10.33 (bs, 1H), 8.60 (d, 1H), 8.46 (d, 1H), 7.17-7.23 (m, 1H), 7.00-7.06 (m, 1H), 5.18 (s, 2H), 4.05 (s, 3H) ppm.

3-(2-Chloro-6-fluoro-3-methoxy-phenylmethanesulfonylamino)-pyrazine-2-carboxylic acid methyl ester. 1H-NMR (400 MHz, CDCl$_3$): 10.29 (bs, 1H), 8.60 (d, 1H), 8.44 (d, 1H), 6.92-7.03 (m, 2H), 5.19 (s, 2H), 4.03 (s, 3H), 3.88 (s, 3H) ppm.

3-(2-Chloro-6-fluoro-5-methoxy-phenylmethanesulfonylamino)-pyrazine-2-carboxylic acid methyl ester. 1H-NMR (400 MHz, CDCl$_3$): 10.49 (bs, 1H), 8.56 (d, 1H), 8.48 (d, 1H), 7.34 (d, 1H), 7.19-7.22 (m, 1H), 7.03 (t, 1H), 4.08 (s, 3H), 3.91 (s, 3H) ppm.

3-(2-Chloro-6-fluoro-3-methyl-phenyl)-methanesulfonylamino)-pyrazine-2-carboxylic acid methyl ester. 1H-NMR (400 MHz, CDCl$_3$): 10.28 (s, 1H), 8.59 (d, 1H), 7.24-7.27 (m, 1H), 6.93 (t, 1H), 5.20 (s, 2H), 4.04 (s, 3H), 2.36 (s, 3H) ppm.

3-(2-Chloro-4-iodo-phenylmethanesulfonylamino)-pyrazine-2-carboxylic acid methyl ester. 1H-NMR (400 MHz, CDCl$_3$): 10.23 (s, 1H), 8.57 (d, 1H), 8.45 (d, 1H), 7.76 (s, 1H), 7.63 (d, 1H), 7.24 (d, 1H), 5.03 (s, 2H), 4.04 (s, 3H) ppm.

3-(2-Chloro-5-iodo-phenylmethanesulfonylamino)-pyrazine-2-carboxylic acid methyl ester. 1H-NMR (400 MHz, CDCl$_3$): 10.28 (s, 1H), 8.58 (d, 1H), 8.46 (d, 1H), 7.83 (d, 1H), 7.62-7.64 (dd, 1H), 7.13 (d, 1H), 5.03 (s, 2H), 4.05 (s, 3H) ppm.

3-(2-Chloro-quinolin-3-yl)-methanesulfonylamino)-pyrazine-2-carboxylic acid methyl ester. 1H-NMR (400 MHz, CDCl$_3$): 10.33 (s, 1H), 8.57 (d, 1H), 8.47 (d, 1H), 8.45 (s, 1H), 8.02 (d, 1H), 7.88 (d, 1H), 7.80 (dt, 1H), 7.62 (dt, 1H), 5.27 (s, 2H), 4.02 (s, 3H) ppm.

3-(2-Chloro-3-trifluoromethyl-phenylmethanesulfonylamino)-pyrazine-2-carboxylic acid methyl ester. 1H-NMR (400 MHz, CDCl$_3$): 10.30 (s, 1H), 8.57 (d, 1H), 8.46 (d, 1H), 7.76 (t, 2H), 7.44 (t, 1H), 5.19 (s, 2H), 4.04 (s, 3H) ppm.

3-(2-Chloro-6-trifluoromethyl-phenylmethanesulfonylamino)-pyrazine-2-carboxylic acid methyl ester. 1H-NMR (400 MHz, CDCl$_3$): 10.38 (bs, 1H), 8.58 (d, 1H), 8.46 (d, 1H), 7.68-7.70 (d, 2H), 7.46-7.49 (m, 1H), 5.40 (s, 2H), 4.05 (s, 3H) ppm.

3-(3-Chloro-5-trifluoromethyl-phenylmethanesulfonylamino)-pyrazine-2-carboxylic acid methyl ester. 1H-NMR (400 MHz, CDCl$_3$): 10.24 (s, 1H), 8.61 (d, 1H), 8.50 (d, 1H), 7.64 (s, 1H), 7.60 (s, 1H), 7.50 (s, 1H), 4.92 (s, 2H), 4.04 (s, 3H) ppm.

3-(4-Chloro-2-trifluoromethyl-phenylmethanesulfonylamino)-pyrazine-2-carboxylic acid methyl ester. 1H-NMR (400 MHz, CDCl$_3$): 10.35 (bs, 1H), 8.56 (d, 1H), 8.46 (d, 1H), 7.71-7.77 (m, 2H), 7.57-7.60 (m, 1H), 5.12 (s, 2H), 4.05 (s, 3H) ppm.

3-(5-Chloro-2-trifluoromethyl-phenylmethanesulfonylamino)-pyrazine-2-carboxylic acid methyl ester. 1H-NMR (400 MHz, CDCl$_3$): 10.38 (s, 1H), 8.57 (d, 1H), 8.47 (d, 1H), 7.81 (s, 1H), 7.66 (d, 1H), 7.49 (d, 1H), 5.12 (s, 2H), 4.06 (s, 3H) ppm.

3-(2-Cyano-phenylmethanesulfonylamino)-pyrazine-2-carboxylic acid methyl ester. 1H-NMR (400 MHz, CDCl$_3$): 10.24 (s, 1H), 8.63 (d, 1H), 8.47 (d, 1H), 7.64-7.72 (m, 3H), 7.50-7.53 (t, 1H), 5.15 (s, 2H), 4.04 (s, 3H) ppm.

3-(2,6-Dibromo-phenylmethanesulfonylamino)-pyrazine-2-carboxylic acid methyl ester. 1H-NMR (400 MHz, CDCl$_3$): 10.39 (s, 1H), 8.57 (d, 1H), 8.43 (d, 1H), 7.60 (d, 2H), 7.07-7.11 (m, 1H), 5.42 (s, 2H), 4.05 (s, 3H) ppm.

3-(2,3-Dichloro-6-fluoro-phenylmethanesulfonylamino)-pyrazine-2-carboxylic acid methyl ester. 1H-NMR (400 MHz, CDCl$_3$): 10.33 (bs, 1H), 8.59 (d, 1H), 8.45 (d, 1H), 7.48-7.52 (m, 1H), 7.00-7.05 (m, 1H), 5.21 (s, 2H), 4.05 (s, 3H) ppm.

3-(2,4-Dichloro-5-fluoro-phenylmethanesulfonylamino)-pyrazine-2-carboxylic acid methyl ester. 1H-NMR (400 MHz, CDCl$_3$): 10.29 (s, 1H), 8.58 (d, 1H), 8.47 (d, 1H), 7.48 (d, 1H), 7.38 (d, 1H), 5.05 (s, 2H), 4.05 (s, 3H) ppm.

3-(2,3-Dichloro-phenylmethanesulfonylamino)-pyrazine-2-carboxylic acid methyl ester. 1H-NMR (400 MHz, CDCl$_3$): 10.26 (s, 1H), 8.58 (d, 1H), 8.46 (d, 1H), 7.44-7.51 (m, 2H), 7.25 (t, 1H), 5.15 (s, 2H), 4.04 (s, 3H) ppm.

3-(2,4-Dichloro-phenylmethanesulfonylamino)-pyrazine-2-carboxylic acid methyl ester. 1H-NMR (400 MHz, CDCl$_3$): 10.24 (bs, 1H), 8.58 (d, 1H), 8.46 (d, 1H), 7.46-7.48 (d, 1H), 7.42 (d, 1H), 7.28-7.31 (dd, 1H), 5.06 (s, 2H), 4.04 (s, 3H) ppm.

3-(2,6-Dichloro-phenylmethanesulfonylamino)-pyrazine-2-carboxylic acid methyl ester. 1H-NMR (400 MHz, CDCl$_3$): 10.36 (bs, 1H), 8.58 (d, 1H), 8.43 (d, 1H), 7.37-7.39 (m, 2H), 7.25-7.29 (m, 1H), 5.34 (s, 2H), 4.05 (s, 3H) ppm.

3-(3,4-Dichloro-phenylmethanesulfonylamino)-pyrazine-2-carboxylic acid methyl ester. 1H-NMR (400 MHz, CDCl$_3$): 10.17 (bs, 1H), 8.60 (d, 1H), 8.49 (d, 1H), 7.43-7.46 (m, 2H), 7.20-7.23 (m, 1H), 4.84 (s, 2H), 4.04 (s, 3H) ppm.

3-(2,3-Dichloro-6-trifluoromethyl-phenylmethanesulfonylamino)-pyrazine-2-carboxylic acid methyl ester. 1H-NMR (400 MHz, CDCl$_3$): 10.41 (s, 1H), 8.58 (d, 1H), 8.47 (d, 1H), 7.61-7.66 (m, 2H), 5.44 (s, 2H), 4.06 (s, 3H) ppm.

3-(2,5-Dichloro-6-trifluoromethyl-phenylmethanesulfonylamino)-pyrazine-2-carboxylic acid methyl ester. 1H-NMR (400 MHz, CDCl$_3$): 10.41 (s, 1H), 8.58 (d, 1H), 8.47 (d, 1H), 7.61-7.67 (m, 2H), 5.44 (s, 2H), 4.06 (s, 3H) ppm.

3-(3-Ethoxycarbonyl-6-trifluoromethyl-pyrid-2-yl-methanesulfonylamino)-pyrazine-2-carboxylic acid methyl ester. 1H-NMR (400 MHz, CDCl$_3$): 10.09 (s, 8.58 (d, 1H), 8.49 (d, 1H), 8.45 (d, 1H), 7.71 (d, 1H), 5.73 (s, 2H), 4.49 (q, 2H), 3.99 (s, 3H), 1.46 (t, 3H) ppm.

3-(2-Fluoro-6-trifluoromethyl-phenylmethanesulfonylamino)-pyrazine-2-carboxylic acid methyl ester. 1H-NMR (400 MHz, CDCl$_3$): 10.33 (s, 1H), 8.59 (d, 1H), 8.46 (d, 1H), 7.50-7.58 (m, 2H), 7.33 (t, 1H), 5.25 (s, 2H), 4.05 (s, 3H) ppm.

3-(2-Iodo-phenylmethanesulfonylamino)-pyrazine-2-carboxylic acid methyl ester. 1H-NMR (400 MHz, CDCl$_3$): 10.24 (bs, 1H), 8.59 (d, 1H), 8.44 (d, 1H), 7.88 (d, 1H), 7.53 (dd, 1H), 7.37 (t, 1H), 7.06 (dt, 1H), 5.13 (s, 2H), 4.04 (s, 3H) ppm.

3-(5-Methyl-2-trifluoromethyl-phenylmethanesulfonylamino)-pyrazine-2-carboxylic acid methyl ester. 1H-NMR (400 MHz, CDCl$_3$): 10.32 (s, 1H), 8.57 (d, 1H), 8.45 (d, 1H), 7.60 (s, 1H), 7.58 (s, 1H), 7.29 (d, 1H), 5.11 (s, 2H), 4.05 (s, 3H), 2.43 (s, 3H) ppm.

3-(2-Nitro-phenylmethanesulfonylamino)-pyrazine-2-carboxylic acid methyl ester. 1H-NMR (400 MHz, CDCl$_3$): 10.15 (s, 1H), 8.58 (d, 1H), 8.47 (d, 1H), 7.97 (d, 1H), 7.55-7.66 (m, 3H), 5.44 (s, 2H), 4.03 (s, 3H) ppm.

3-(2,3,6-Trichloro-phenylmethanesulfonylamino)-pyrazine-2-carboxylic acid methyl ester. 1H-NMR (400 MHz, CDCl$_3$): 10.40 (bs, 1H), 8.57 (d, 1H), 8.45 (d, 1H), 7.45 (d, 1H), 7.33 (d, 1H), 5.38 (s, 2H), 4.05 (s, 3H) ppm.

3-(2-Trifluoromethoxy-phenylmethanesulfonylamino)-pyrazine-2-carboxylic acid methyl ester. 1H-NMR (400 MHz, CDCl$_3$): 10.15 (bs, 1H), 8.59 (d, 1H), 8.45 (d, 1H), 7.58-7.61 (dd, 1H), 7.41-7.46 (m, 1H), 7.32-7.36 (m, 1H), 7.23-7.25 (m, 1H), 5.00 (s, 2H), 4.02 (s, 3H) ppm.

3-(2-Trifluoromethyl-phenylmethanesulfonylamino)-pyrazine-2-carboxylic acid methyl ester. 1H-NMR (400 MHz, CDCl$_3$): 10.31 (s, 1H), 8.57 (d, 1H), 8.45 (d, 1H), 7.80 (d, 1H), 7.72 (d, 1H), 7.61 (t, 1H), 7.51 (t, 1H), 5.16 (s, 2H), 4.05 (s, 3H) ppm.

3-(3-Trifluoromethyl-phenylmethanesulfonylamino)-pyrazine-2-carboxylic acid methyl ester. 1H-NMR (400 MHz, CDCl$_3$): 10.16 (bs, 1H), 8.61 (d, 1H), 8.48 (d, 1H), 7.49-7.66 (m, 4H), 4.95 (s, 2H), 4.03 (s, 3H) ppm.

3-(2-Trifluoromethylthio-phenylmethanesulfonylamino)-pyrazine-2-carboxylic acid methyl ester. 1H-NMR (400 MHz, CDCl$_3$): 10.21 (bs, 1H), 8.62 (d, 1H), 8.48 (d, 1H), 7.81-7.83 (dd, 1H), 7.58-7.60 (m, 1H), 7.45-7.54 (m, 2H), 5.31 (s, 2H), 4.04 (s, 3H) ppm.

Example 2.2

Preparation of 3-[(2-chloro-3,6-difluoro-phenylmethanesulfonyl)-methyl-amino]-pyrazine-2-carboxylic acid methyl ester

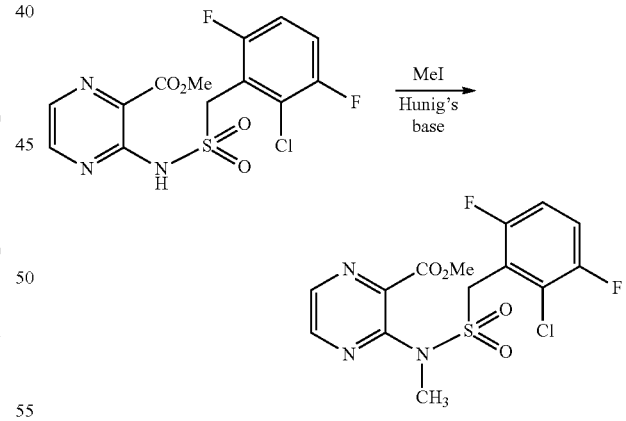

To a solution of 3-(2-chloro-3,6-difluoro-phenylmethanesulfonylamino)-pyrazine-2-carboxylic acid methyl ester (Example 2.1) (420 mg) in acetonitrile (4 ml) was added N,N-diisopropylethylamine ("Hunig's base") (0.39 ml) and methyl iodide (0.28 ml). The reaction mixture was heated in a microwave at 150° C. for 30 minutes. The reaction mixture was allowed to cool to ambient temperature and then partitioned between diethyl ether and aqueous hydrochloric acid (2M). The phases were separated. The aqueous layer was extracted with diethyl ether. The combined organic extracts were washed with brine and concentrated to give 3-[(2- chloro-3,6-difluoro-phenylmethanesulfonyl)-methyl-amino]-pyrazine-2-carboxylic acid methyl ester as an orange oil (0.307 g). 1H-NMR (400 MHz, CDCl₃): 8.58 (d, 1H), 8.56 (d, 1H), 7.13-7.19 (m, 1H), 7.00-7.06 (m, 1H), 4.82 (s, 2H), 4.02 (s, 3H), 3.51 (s, 3H) ppm.

The following compound was made using the same method:

3-[(2-Chloro-quinolin-3-ylmethanesulfonyl)-methyl-amino]-pyrazine-2-carboxylic acid methyl ester. 1H-NMR (400 MHz, CDCl₃): 8.54 (d, 1H), 8.53 (d, 1H), 8.45 (s, 1H), 8.10 (d, 1H), 7.92 (d, 1H), 7.84 (dt, 1H), 7.65 (dt, 1H), 4.88 (s, 2H), 4.02 (s, 3H), 3.53 (s, 3H) ppm.

3-[(2-Chloro-5-trifluoromethyl-phenylmethanesulfonyl)-methyl-amino]-pyrazine-2-carboxylic acid methyl ester. 1H-NMR (400 MHz, CDCl₃): 8.58 (d, 1H), 8.53 (d, 1H), 7.83 (bs, 1H), 7.54-7.56 (m, 2H), 4.76 (s, 2H), 4.03 (s, 3H), 3.43 (s, 3H) ppm.

3-[(2,4-Dichloro-phenylmethanesulfonyl)-methyl-amino]-pyrazine-2-carboxylic acid methyl ester. 1H-NMR (400 MHz, CDCl₃): 8.55 (d, 1H), 8.48 (d, 1H), 7.44-7.46 (m, 2H), 7.16-7.18 (m, 1H), 4.67 (s, 2H), 4.02 (s, 3H), 3.43 (s, 3H) ppm.

3-[(2,3,6-Trichloro-phenylmethanesulfonyl)-methyl-amino]-pyrazine-2-carboxylic acid methyl ester. 1H-NMR (400 MHz, CDCl₃): 8.61 (d, 1H), 8.59 (d, 1H), 7.41 (d, 1H), 7.31 (d, 1H), 5.03 (s, 2H), 4.02 (s, 3H), 3.54 (s, 3H) ppm.

Example 23

Preparation of 3-[(2-chloro-5-trifluoromethyl-phenylmethanesulfonyl)-ethyl-amino]-pyrazine-2-carboxylic acid methyl ester

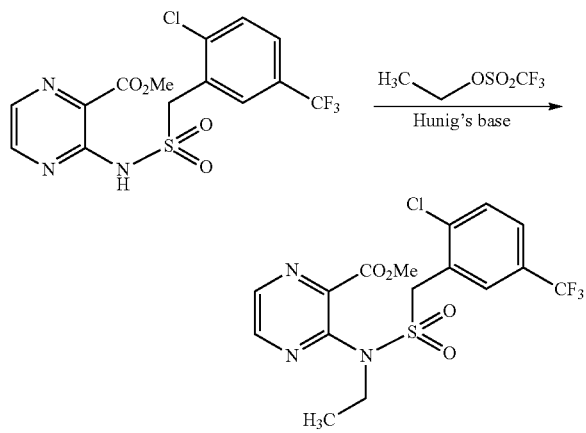

To a solution of 3-(2-chloro-5-trifluoromethyl-phenyl-methanesulfonylamino)-pyrazine-2-carboxylic acid methyl ester (Example 2.1) (1.5 g) in acetonitrile (20 ml) was added N,N-diisopropylethylamine ("Hunig's base") (0.71 ml) at ambient temperature. The mixture was stirred for 5 minutes at ambient temperature before dropwise addition of a solution of ethyltrifluoromethanesulfonate (0.71 ml) in acetonitrile (5 ml) at ambient to temperature. The reaction mixture was stirred at ambient temperature for 4 hours. The reaction mixture was concentrated and the residue purified by column chromatography on silica gel (eluent: dichloromethane) to give 3-[(2-chloro-5-trifluoromethyl-phenyl-methanesulfonyl)-ethyl-amino]-pyrazine-2-carboxylic acid methyl ester as a beige solid (0.968 g). 1H-NMR (400 MHz, CDCl₃): 8.57 (d, 1H), 8.52 (d, 1H), 7.77 (m, 1H), 7.50-7.56 (m, 2H), 4.64 (m, 2H), 4.01 (q, 2H), 4.00 (s, 3H), 1.23 (t, 3H) ppm.

The following compounds were made using the same method:

3-[(2,5-Bis-(trifluoromethyl)-phenylmethanesulfonyl)-ethyl-amino]-pyrazine-2-carboxylic acid methyl ester. 1H-NMR (400 MHz, CDCl₃): 8.66 (d, 1H), 8.58 (d, 1H), 7.96 (s, 1H), 7.84 (d, 1H), 7.71 (d, 1H), 4.62 (s, 2H), 4.04 (q, 2H), 4.01 (s, 3H), 1.26 (t, 3H) ppm.

3-[(3-Bromo-2-chloro-6-fluoro-phenylmethanesulfonyl)-ethyl-amino]-pyrazine-2-carboxylic acid methyl ester. 1H-NMR (400 MHz, CDCl₃): 8.59-8.61 (m, 2H), 7.57-7.64 (m, 1H), 6.92-6.99 (m, 1H), 4.74 (s, 2H), 4.10-4.15 (q, 2H), 4.03 (s, 3H), 1.29 (t, 3H) ppm.

3-[(2-Bromo-5-trifluoromethyl-phenylmethanesulfonyl)-ethyl-amino]-pyrazine-2-carboxylic acid methyl ester. 1H-NMR (400 MHz, CDCl₃): 8.59 (d, 1H), 8.54 (d, 1H), 7.73-7.77 (m, 2H), 7.42-7.44 (dd, 1H), 4.66 (s, 2H), 4.03 (q, 2H), 4.01 (s, 3H), 1.26 (t, 3H) ppm.

3-[(2-Chloro-6-fluoro-3-methoxy-phenylmethanesulfonyl)-ethyl-amino]-pyrazine-2-carboxylic acid methyl ester. 1H-NMR (400 MHz, CDCl₃): 8.57-8.59 (m, 2H), 6.96-7.01 (m, 1H), 6.86-6.89 (m, 1H), 4.70 (s, 2H), 4.11 (q, 2H), 3.99 (s, 3H), 3.86 (s, 3H), 1.27 (t, 3H) ppm.

3-[(2-Chloro-6-fluoro-3-methyl-phenylmethanesulfonyl)-ethyl-amino]-pyrazine-2-carboxylic acid methyl ester. 1H-NMR (400 MHz, CDCl₃): 10.28 (bs, 1H), 8.59 (d, 1H), 8.44 (d, 1H), 7.24-7.27 (m, 1H), 6.91-6.95 (m, 1H), 5.20 (s, 2H), 4.04 (s, 3H), 2.36 (s, 3H) ppm.

3-[(2,4-Dichloro-5-fluoro-phenylmethanesulfonyl)-ethyl-amino]-pyrazine-2-carboxylic acid methyl ester. 1H-NMR (400 MHz, CDCl₃): 8.41-8.44 (m, 2H), 7.30 (d, 1H), 7.15 (d, 1H), 4.26 (q, 2H), 3.85 (q, 2H), 3.79 (s, 3H), 1.23 (t, 3H) ppm.

3-[(3,4-Dichloro-phenylmethanesulfonyl)-ethyl-amino]-pyrazine-2-carboxylic acid methyl ester. 1H-NMR (400 MHz, CDCl₃): 8.58 (d, 1H), 8.55 (d, 1H), 7.52-7.53 (m, 1H), 7.39-7.41 (m, 1H), 7.24-7.26 (m, 1H), 4.27 (s, 2H), 4.01 (s, 3H), 3.86 (q, 2H), 1.15 (t, 3H) ppm.

3-[(2-Fluoro-6-trifluoromethyl-phenylmethanesulfonyl)-ethyl-amino]-pyrazine-2-carboxylic acid methyl ester. 1H-NMR (400 MHz, CDCl₃): 8.65 (d, 1H), 8.63 (d, 1H), 7.43-7.50 (m, 2H), 7.27-7.31 (m, 1H), 4.70-4.71 (m, 2H), 4.46 (q, 2H), 3.99 (s, 3H), 1.28 (t, 3H) ppm.

3-[(2-Trifluoromethyl-phenylmethanesulfonyl)-ethyl-amino]-pyrazine-2-carboxylic acid methyl ester. 1H-NMR (400 MHz, CDCl₃): 8.62 (d, 1H), 8.61 (d, 1H), 7.65-7.69 (m, 2H), 7.42-7.51 (m, 2H), 4.58 (s, 2H), 4.06 (q, 2H), 3.99 (s, 3H), 1.26 (t, 3H), ppm.

3-[(2-Trifluoromethylthio-phenylmethanesulfonyl)-ethyl-amino]-pyrazine-2-carboxylic acid methyl ester. 1H-NMR (400 MHz, CDCl₃): 8.56 (d, 1H), 8.53 (d, 1H), 7.75-7.77 (m, 1H), 7.57-7.59 (m, 1H), 7.36-7.46 (m, 2H), 4.74 (s, 2H), 4.01 (q, 2H), 3.99 (s, 3H), 1.23 (t, 3H) ppm.

Example 2.4

Preparation of 3-[(2,3-dichloro-6-fluoro-phenyl-methanesulfonyl)-ethyl-amino]-pyrazine-2-carboxylic acid ethyl ester

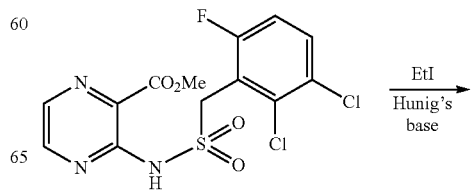

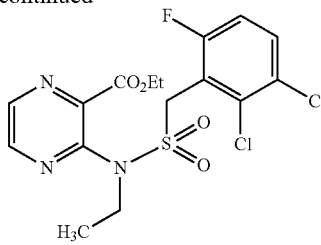

To a solution of 3-(2,3-dichloro-6-fluoro-phenylmethanesulfonylamino)-pyrazine-2-carboxylic acid methyl ester (Example 2.1) (250 mg) in N,N-dimethyl-formamide (2 ml) was added N,N-diisopropylethylamine ("Hunig's base") (0.22 ml) and ethyl iodide (0.152 ml). The reaction mixture was heated in a microwave at 150° C. for 30 minutes. The reaction mixture was allowed to cool to ambient temperature and concentrated. The residue was purified by column chromatography on silica gel (eluent: ethyl acetate/dichloromethane 1:9) to give 3-[(2,3-dichloro-6-fluoro-phenylmethanesulfonyl)-ethyl-amino]-pyrazine-2-carboxylic acid ethyl ester as a beige solid (0.206 g). 1H-NMR (400 MHz, CDCl$_3$): 8.62 (d, 1H), 8.58 (d, 1H), 7.41-7.44 (m, 1H), 6.97-7.01 (m, 1H), 4.70 (m, 2H), 4.47 (q, 2H), 4.10 (q, 3H), 1.43 (t, 3H), 1.27 (t, 3H) ppm.

In this example, N-alkylation was accompanied by transesterification (that is, the starting material was a methyl ester and the product isolated was identified as an ethyl ester). In the analogous reactions listed below, transesterification was during the N-alkylation was observed only in one further case.

The following compounds were made using the same method:

3-[(2,6-Bis-(trifluoromethyl)-phenylmethanesulfonyl)-ethyl-amino]-pyrazine-2-carboxylic acid methyl ester. 1H-NMR (400 MHz, CDCl$_3$): 8.66 (m, 2H), 7.88 (d, 2H), 7.59 (t, 1H), 4.89 (s, 2H), 4.10 (q, 2H), 3.95 (s, 3H), 1.27 (t, 3H) ppm.

3-[(2-Chloro-6-trifluoromethyl-phenylmethanesulfonyl)-ethyl-amino]-pyrazine-2-carboxylic acid methyl ester. The crude compound was used directly for further synthesis.

3-[(2-Trifluoromethoxy-phenylmethanesulfonyl)-ethyl-amino]-pyrazine-2-carboxylic acid methyl ester. The crude compound was used directly for further synthesis.

3-[(2-Chloro-5-iodo-phenylmethanesulfonyl)-ethyl-amino]-pyrazine-2-carboxylic acid methyl ester. 1H-NMR (400 MHz, CDCl$_3$): 8.58 (d, 1H), 8.55 (d, 1H), 7.77 (d, 1H), 7.54-7.57 (dd, 1H), 7.13 (d, 1H), 4.52 (s, 2H), 4.02 (q, 2H), 4.00 (s, 3H), 1.22-1.25 (m, 3H) ppm.

3-[(2-Chloro-3-trifluoromethyl-phenylmethanesulfonyl)-ethyl-amino]-pyrazine-2-carboxylic acid methyl ester. 1H-NMR (400 MHz, CDCl$_3$): 8.52 (d, 1H), 8.46 (d, 1H), 7.66 (d, 2H), 7.26 (t, 1H), 4.69 (s, 2H), 4.08 (q, 2H), 3.99 (s, 3H), 1.26 (t, 3H) ppm.

3-[(4-Chloro-2-trifluoromethyl-phenylmethanesulfonyl)-ethyl-amino]-pyrazine-2-carboxylic acid methyl ester. 1H-NMR (400 MHz, CDCl$_3$): 8.62 (d, 1H), 8.56 (d, 1H), 7.67 (d, 1H), 7.59-7.61 (d, 1H), 7.42-7.44 (dd, 1H), 4.52 (s, 2H), 4.04 (q, 2H), 4.00 (s, 3H), 1.25 (t, 3H) ppm.

3-[(5-Chloro-2-trifluoromethyl-phenylmethanesulfonyl)-ethyl-amino]-pyrazine-2-carboxylic acid methyl ester. 1H-NMR (400 MHz, CDCl$_3$): 8.63 (d, 1H), 8.59 (d, 1H), 7.67 (s, 1H), 7.62 (d, 1H), 7.41 (d, 1H), 4.53 (s, 2H), 4.04 (q, 2H), 4.01 (s, 3H), 1.26 (t, 3H) ppm.

3-[(3-Trifluoromethyl-phenylmethanesulfonyl)-ethyl-amino]-pyrazine-2-carboxylic acid ethyl ester. 1H-NMR (400 MHz, CDCl$_3$): 8.57 (d, 1H), 8.51 (d, 1H), 7.70 (m, 1H), 7.59-7.62 (m, 2H), 7.43-7.47 (m, 1H), 4.46 (q, 2H), 4.38 (s, 2H), 3.85 (q, 2H), 1.44 (t, 3H), 1.13 (t, 3H) ppm.

3-[(2,3-Dichloro-phenylmethanesulfonyl)-ethyl-amino]-pyrazine-2-carboxylic acid methyl ester. 1H-NMR (400 MHz, CDCl$_3$): 8.53 (d, 1H), 8.49 (d, 1H), 7.36-7.42 (m, 2H), 7.09 (t, 1H), 4.63 (s, 2H), 4.06 (q, 2H), 3.99 (s, 3H), 1.23 (t, 3H) ppm.

3-[(2,4-Dichloro-phenylmethanesulfonyl)-ethyl-amino]-pyrazine-2-carboxylic acid methyl ester. 1H-NMR (400 MHz, CDCl$_3$): 8.55 (d, 1H), 8.47 (d, 1H), 7.43 (d, 1H), 7.37-7.39 (d, 1H), 7.12-7.44 (d, 1H), 4.54 (s, 2H), 4.03-4.06 (q, 2H), 4.00 (s, 3H), 1.25 (t, 3H) ppm.

3-[(2,5-Dichloro-6-trifluoromethyl-phenylmethanesulfonyl)-ethyl-amino]-pyrazine-2-carboxylic acid methyl ester. 1H-NMR (400 MHz, CDCl$_3$): 8.66-8.67 (m, 2H), 7.53-7.59 (m, 2H), 4.91 (s, 2H), 4.14 (q, 2H), 3.99 (s, 3H), 1.29 (t, 3H) ppm.

3-[(2-Nitro-phenylmethanesulfonyl)-ethyl-amino]-pyrazine-2-carboxylic acid methyl ester. 1H-NMR (400 MHz, CDCl$_3$): 8.60 (d, 1H), 8.58 (d, 1H), 8.05 (d, 1H), 7.49-7.58 (m, 3H), 4.96 (s, 2H), 3.98 (s, 3H), 3.94 (q, 2H), 1.18 (t, 3H) ppm.

3-[(2,3,6-Trichloro-phenylmethanesulfonyl)-ethyl-amino]pyrazine-2-carboxylic acid methyl ester. 1H-NMR (400 MHz, CDCl$_3$): 8.63-8.64 (m, 2H), 7.39 (d, 1H), 7.28 (d, 1H), 4.88 (s, 2H), 4.14 (q, 2H), 4.00 (s, 3H), 1.29 (t, 3H) ppm.

Example 2.5

Preparation of 3-[(2-trifluoromethylthio-phenylmethanesulfonyl)-methoxymethyl-amino]-pyrazine-2-carboxylic acid methyl ester

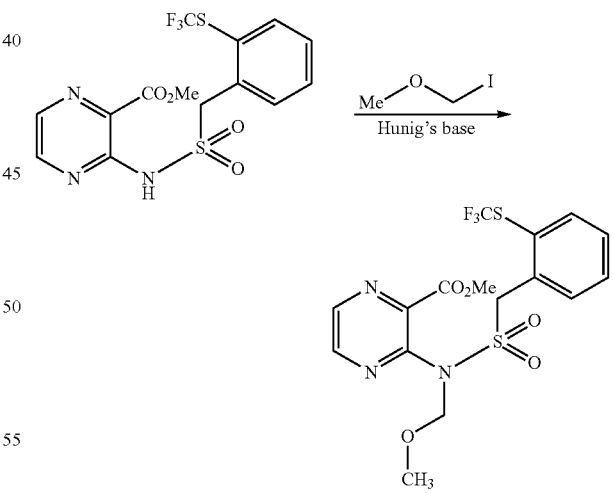

To a solution of 3-(2-trifluoromethylthio-phenylmethanesulfonylamino)-pyrazine-2-carboxylic acid methyl ester (Example 2.1) (250 mg) in acetonitrile (5 ml) was added N,N-diisopropylethylamine ("Hunig's base") (0.12 ml) at ambient temperature. The mixture was stirred for 5 minutes at ambient temperature before addition of the iodomethylmethyl ether (0.105 ml). The reaction mixture was stirred at ambient temperature for 18 hours. The reaction mixture was concentrated. The residue was purified by column chromatography on silica gel (eluent: ethyl acetate/dichloromethane 5:95) to give 3-[(2-trifluoromethylthio-phenylmethanesulfonyl)-methoxymethyl-amino]-pyrazine-2-carboxylic acid methyl ester as a dark orange gum (0.221 g). 1H-NMR (400 MHz, CDCl$_3$): 8.66 (d, 1H), 8.64 (d, 1H), 7.78-7.80 (m, 1H), 7.63-7.66 (m, 1H), 7.41-7.51 (m, 2H), 5.18 (s, 2H), 4.98 (s, 2H), 4.01 (s, 3H), 3.51 (s, 3H) ppm.

The following compound was made using the same method:

3-[(2,4-Dichloro-phenylmethanesulfonyl)-methoxymethyl-amino]-pyrazine-2-carboxylic acid methyl ester. 1H-NMR (400 MHz, CDCl$_3$): 8.60 (d, 1H), 7.78-7.80 (m, 1H), 7.45-7.47 (m, 2H), 7.19-7.22 (dd, 1H), 5.23 (s, 2H), 4.78 (s, 2H), 4.01 (s, 3H), 3.51 (s, 3H) ppm.

Example 2.6

Preparation of 3-[(2-chloro-5-trifluoromethyl-phenylmethanesulfonyl)-(2,2-difluoro-ethyl)-amino]-pyrazine-2-carboxylic acid methyl ester

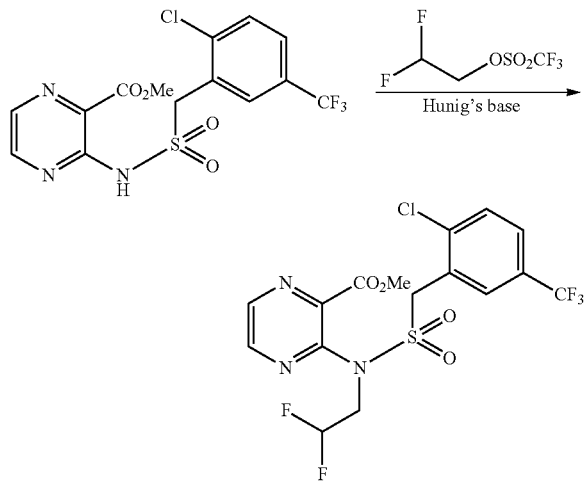

To a solution of 3-(2-chloro-5-trifluoromethyl-phenylmethanesulfonylamino)-pyrazine-2-carboxylic acid methyl ester (Example 2.1) (1.5 g) in acetonitrile (15 ml) was added N,N-diisopropylethylamine ("Hunig's base") (0.71 ml) at ambient temperature. The mixture was stirred for 5 minutes at ambient temperature before dropwise addition of a solution of 2,2-difluoroethyltrifluoromethanesulfonate (1.2 g) in acetonitrile (5 ml) at ambient temperature. The reaction mixture was stirred at ambient temperature for 44 hours. The reaction mixture was concentrated. The residue was purified by column chromatography on silica gel (eluent: dichloromethane) to give 3-[(2-chloro-5-trifluoromethyl-phenylmethanesulfonyl)-(2,2-difluoro-ethyl)-amino]-pyrazine-2-carboxylic acid methyl ester as a light yellow solid (1.300 g). 1H-NMR (400 MHz, CDCl$_3$): 8.63 (s, 1H), 8.53 (s, 1H), 7.76 (m, 1H), 7.53-7.59 (m, 2H), 6.15 (tt, 1H), 4.69 (s, 2H), 4.23-4.31 (m, 2H), 4.02 (s, 3H) ppm.

The following compounds were made using the same method:

3-[(2,4-Bis-(trifluoromethyl)-phenylmethanesulfonyl)-(2,2-difluoro-ethyl)-amino]-pyrazine-2-carboxylic acid methyl ester. 1H-NMR (400 MHz, CDCl$_3$): 8.66 (d, 1H), 8.52 (d, 1H), 7.95 (s, 1H), 7.80 (d, 1H), 7.72 (s, 1H), 6.01-6.31 (tt, 1H), 4.70 (s, 2H), 4.29-4.36 (dt, 2H), 4.01 (s, 3H) ppm.

3-[(2,5-Bis-(trifluoromethyl)-phenylmethanesulfonyl)-(2,2-difluoro-ethyl)-amino]-pyrazine-2-carboxylic acid methyl ester. 1H-NMR (400 MHz, CDCl$_3$): 8.69 (d, 1H), 8.58 (d, 1H), 7.94 (s, 1H), 7.86 (d, 1H), 7.73 (d, 1H), 6.02-6.32 (tt, 1H), 4.71 (s, 2H), 4.27-4.34 (dt, 2H), 4.02 (s, 3H) ppm.

3-[(2,6-Bis-(trifluoromethyl)-phenylmethanesulfonyl)-(2,2-difluoro-ethyl)-amino]-pyrazine-2-carboxylic acid methyl ester. 1H-NMR (400 MHz, CDCl$_3$): 8.73 (d, 1H), 8.69 (d, 1H), 7.91 (d, 2H), 7.63 (t, 1H), 6.04-6.34 (tt, 1H), 5.00 (s, 2H), 4.36-4.43 (dt, 2H), 3.99 (s, 3H) ppm.

3-[(3-Bromo-2-chloro-6-fluoro-phenylmethanesulfonyl)-(2,2-difluoro-ethyl)-amino]-pyrazine-2-carboxylic acid methyl ester. 1H-NMR (400 MHz, CDCl$_3$): 8.64 (d, 1H), 8.57 (d, 1H), 7.59-7.63 (m, 1H), 6.92-6.97 (m, 1H), 6.05-6.33 (tt, 1H), 4.80 (s, 2H), 4.34-4.42 (m, 2H), 4.01 (s, 3H) ppm.

3-[(2-Bromo-phenylmethanesulfonyl)-(2,2-difluoro-ethyl)-amino]pyrazine-2-carboxylic acid methyl ester. 1H-NMR (400 MHz, CDCl$_3$): 8.58 (d, 1H), 8.48 (d, 1H), 7.45-7.63 (m, 2H), 7.17-7.23 (m, 2H), 5.98-6.28 (tt, 1H), 4.65 (s, 2H), 4.26-4.34 (m, 2H), 4.01 (s, 3H) ppm.

3-[(2-Bromo-5-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.64 (d, 1H), 8.55 (d, 1H), 7.75-7.77 (m, 2H), 7.45-7.47 (m, 1H), 6.00-6.30 (tt, 1H), 4.71 (s, 2H), 4.24-4.32 (dt, 2H), 4.02 (s, 3H) ppm.

3-[(4-Bromo-2-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.66 (d, 1H), 8.53 (d, 1H), 7.83 (d, 1H), 7.57-7.60 (dd, 1H), 7.49 (d, 1H), 6.00-6.30 (tt, 1H), 4.57 (s, 2H), 4.26-4.34 (dt, 2H), 4.01 (s, 3H) ppm.

3-[(2-Chloro-6-fluoro-3-methoxy-phenylmethanesulfonyl)-(2,2-difluoro-ethyl)-amino]-pyrazine-2-carboxylic acid methyl ester. 1H-NMR (400 MHz, CDCl$_3$): 8.63 (d, 1H), 8.57 (d, 1H), 6.98-7.03 (m, 1H), 6.88-6.91 (m, 1H), 6.03-6.33 (tt, 1H), 4.75 (s, 2H), 4.35-4.42 (m, 2H), 4.00 (s, 3H), 3.87 (s, 3H) ppm.

3-[(2-Chloro-6-fluoro-5-methoxy-phenylmethanesulfonyl)-(2,2-difluoro-ethyl)-amino]-pyrazine-2-carboxylic acid methyl ester. 1H-NMR (400 MHz, CDCl$_3$): 8.62 (d, 1H), 8.55 (d, 1H), 7.13 (d, 1H), 6.90 (t, 1H), 6.03-6.32 (m, 1H), 4.71 (s, 2H), 4.35-4.42 (dt, 2H), 4.00 (s, 3H), 3.88 (s, 3H) ppm.

3-[(2-Chloro-6-fluoro-3-methyl-phenylmethanesulfonyl)-(2,2-difluoro-ethyl)-amino]pyrazine-2-carboxylic acid methyl ester. 1H-NMR (400 MHz, CDCl$_3$): 8.62 (d, 1H), 8.55 (d, 1H), 7.19-7.22 (m, 1H), 6.91-6.96 (m, 1H), 6.03-6.33 (tt, 1H), 4.75 (s, 2H), 4.35-4.42 (m, 2H), 4.00 (s, 3H), 2.34 (s, 3H) ppm.

3-[(2-Chloro-4-iodo-phenylmethanesulfonyl)-(2,2-difluoro-ethyl)-amino]-pyrazine-2-carboxylic acid methyl ester. 1H-NMR (400 MHz, CDCl$_3$): 8.60 (d, 1H), 8.47 (d, 1H), 7.80 (s, 1H), 7.48 (d, 1H), 7.13 (d, 1H), 5.98-6.28 (tt, 1H), 4.57 (s, 2H), 4.25-4.32 (dt, 2H), 4.00 (s, 3H) ppm.

3-[(2-Chloro-5-iodo-phenylmethanesulfonyl)-(2,2-difluoro-ethyl)-amino]-pyrazine-2-carboxylic acid methyl ester. 1H-NMR (400 MHz, CDCl$_3$): 8.64 (d, 1H), 8.55 (d, 1H), 7.77 (d, 1H), 7.58-7.60 (dd, 1H), 7.16 (d, 1H), 6.00-6.30 (tt, 1H), 4.56 (s, 2H), 4.24-4.32 (m, 2H), 4.02 (s, 3H) ppm.

3-[(2-Chloro-3-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.56 (d, 1H), 8.42 (d, 1H), 7.62-7.68 (m, 2H), 7.26 (t, 1H), 6.00-6.30 (tt, 1H), 4.73 (s, 2H), 4.29-4.37 (dt, 2H), 4.00 (s, 3H) ppm.

3-[(2-Chloro-6-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.71 (d, 1H), 8.66

(d, 1H), 7.62-7.64 (m, 2H), 7.41-7.44 (m, 1H), 6.07-6.31 (tt, 1H), 4.94 (s, 2H), 4.40-4.46 (m, 2H), 4.00 (s, 3H) ppm.

3-[(3-Chloro-5-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.67 (d, 1H), 8.59 (d, 1H), 7.62 (s, 2H), 7.60 (s, 1H), 5.93-6.23 (tt, 1H), 4.41 (s, 2H), 4.09-4.17 (dt, 2H), 4.02 (s, 3H) ppm.

3-[(5-Chloro-2-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.68 (d, 1H), 8.58 (d, 1H), 7.64 (s, 1H), 7.63 (d, 1H), 7.43 (d, 1H), 6.02-6.31 (tt, 1H), 4.60 (s, 2H), 4.27-4.35 (dt, 2H), 4.02 (s, 3H) ppm.

3-[(2-Cyano-phenylmethanesulfonyl)-(2,2-difluoro-ethyl)-amino]-pyrazine-2-carboxylic acid methyl ester. 1H-NMR (400 MHz, d$_6$-DMSO): 8.72 (d, 1H), 8.70 (d, 1H), 7.80 (d, 1H), 7.62-7.66 (m, 1H), 7.55-7.57 (m, 1H), 7.49 (t, 1H), 6.05-6.35 (tt, 1H), 4.84 (s, 2H), 4.30-4.38 (dt, 2H), 3.78 (s, 3H) ppm.

3-[(2,6-Dibromo-phenylmethanesulfonyl)-(2,2-difluoro-ethyl)-amino]-pyrazine-2-carboxylic acid methyl ester. 1H-NMR (400 MHz, CDCl$_3$): 8.64-8.68 (m, 2H), 7.54-7.56 (m, 2H), 7.02-7.06 (m, 1H), 6.06-6.34 (m, 1H), 4.96 (s, 2H), 4.42-4.48 (m, 2H), 4.00 (s, 3H) ppm.

3-[(2,3-Dichloro-6-fluoro-phenylmethanesulfonyl)-(2,2-difluoro-ethyl)-amino]-pyrazine-2-carboxylic acid methyl ester. 1H-NMR (400 MHz, CDCl$_3$): 8.65 (d, 1H), 8.57 (d, 1H), 7.43-7.47 (m, 1H), 6.99-7.03 (m, 1H), 6.04-6.33 (tt, 1H), 4.78 (s, 2H), 4.35-4.42 (m, 2H), 4.01 (s, 3H) ppm.

3-[(2,4-Dichloro-5-fluoro-phenylmethanesulfonyl)-(2,2-difluoro-ethyl)-amino]-pyrazine-2-carboxylic acid methyl ester. 1H-NMR (400 MHz, CDCl$_3$): 8.66 (d, 1H), 8.55 (d, 1H), 7.44 (d, 1H), 7.33 (d, 1H), 6.00-6.30 (tt, 1H), 4.58 (s, 2H), 4.25-4.33 (dt, 2H), 4.01 (s, 3H) ppm.

3-[(2,3-Dichloro-phenylmethanesulfonyl)-(2,2-difluoro-ethyl)-amino]-pyrazine-2-carboxylic acid methyl ester. 1H-NMR (400 MHz, CDCl$_3$): 8.57 (d, 1H), 8.48 (d, 1H), 7.44 (d, 1H), 7.36 (d, 1H), 7.10 (t, 1H), 5.99-6.29 (tt, 1H), 4.68 (s, 2H), 4.27-4.34 (dt, 2H), 4.01 (s, 3H) ppm.

3-[(2,6-Dichloro-phenylmethanesulfonyl)-(2,2-difluoro-ethyl)-amino]-pyrazine-2-carboxylic acid methyl ester. 1H-NMR (400 MHz, CDCl$_3$): 8.67 (d, 1H), 8.62 (d, 1H), 7.33-7.35 (m, 2H), 7.21-7.27 (m, 1H), 6.04-6.34 (tt, 1H), 4.90 (s, 2H), 4.38-4.46 (m, 2H), 4.00 (s, 3H) ppm.

3-[(2,3-Dichloro-6-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.72 (d, 1H), 8.67 (d, 1H), 7.55-7.61 (m, 2H), 6.07-6.31 (tt, 1H), 4.99 (s, 2H), 4.39-4.45 (dt, 2H), 4.00 (s, 3H) ppm.

3-[(2,5-Dichloro-6-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.72 (d, 1H), 8.67 (d, 1H), 7.55-7.61 (m, 2H), 6.05-6.34 (tt, 1H), 4.99 (s, 2H), 4.38-4.46 (dt, 2H), 4.00 (s, 3H) ppm.

3-[(3-Ethoxycarbonyl-6-trifluoromethyl-pyrid-2-yl-methanesulfonyl)-(2,2-difluoro-ethyl)-amino]-pyrazine-2-carboxylic acid methyl ester. 1H-NMR (400 MHz, CDCl$_3$): 8.59 (d, 1H), 8.50 (d, 1H), 8.35 (d, 1H), 7.73 (d, 2H), 6.04-6.28 (tt, 1H), 5.33 (s, 2H), 4.36 (q, 2H), 4.28-4.34 (dt, 2H), 3.98 (s, 3H), 1.37 (t, 3H) ppm.

3-[(2-Fluoro-6-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.68 (s, 1H), 8.64 (s, 1H), 7.45-7.51 (m, 2H), 7.30-7.34 (t, 1H), 6.03-6.33 (tt, 1H), 4.79 (s, 2H), 4.36-4.44 (dt, 2H), 4.00 (s, 3H) ppm.

3-[(2-Iodo-phenylmethanesulfonyl)-(2,2-difluoro-ethyl)-amino]pyrazine-2-carboxylic acid methyl ester. 1H-NMR (400 MHz, CDCl$_3$): 8.61 (d, 1H), 8.53 (d, 1H), 7.88 (d, 1H), 7.48 (dd, 1H), 7.27 (t, 1H), 7.01 (dt, 1H), 6.00-6.29 (tt, 1H), 4.63 (s, 2H), 4.32 (dt, 2H), 4.01 (s, 3H) ppm.

3-[(5-Methyl-2-trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.63 (d, 1H), 8.53 (d, 1H), 7.57 (d, 1H), 7.41 (s, 1H), 7.23 (d, 1H), 6.00-6.30 (tt, 1H), 4.57 (s, 2H), 4.27-4.35 (dt, 2H), 4.01 (s, 3H), 2.33 (s, 3H) ppm.

3-[(2-Nitro-phenylmethanesulfonyl)-(2,2-difluoro-ethyl)-amino]-pyrazine-2-carboxylic acid methyl ester. 1H-NMR (400 MHz, CDCl$_3$): 8.64 (d, 1H), 8.57 (d, 1H), 8.09 (d, 1H), 7.52-7.62 (m, 3H), 5.94-6.24 (m, 1H), 5.02 (s, 2H), 4.16-4.24 (dt, 2H), 3.98 to (s, 3H) ppm.

3-[(2,3,6-Trichloro-phenylmethanesulfonyl)-(2,2-difluoro-ethyl)-amino]-pyrazine-2-carboxylic acid methyl ester. 1H-NMR (400 MHz, CDCl$_3$): 8.69 (d, 1H), 8.63 (d, 1H), 7.41 (d, 1H), 7.29 (d, 1H), 6.04-6.34 (tt, 1H), 4.95 (s, 2H), 4.38-4.45 (m, 2H), 4.01 (s, 3H) ppm.

3-[(2-Trifluoromethoxy-phenylmethanesulfonyl)-(2,2-difluoro-ethyl)-amino]-pyrazine-2-carboxylic acid methyl ester. 1H-NMR (400 MHz, CDCl$_3$): 8.57 (d, 1H), 8.46 (d, 1H), 7.48-7.50 (m, 1H), 7.30-7.41 (m, 2H), 7.17-7.22 (m, 1H), 5.96-6.26 (tt, 1H), 4.51 (s, 2H), 4.17-4.25 (m, 2H), 4.00 (s, 3H) ppm.

3-[(2-Trifluoromethyl-phenylmethanesulfonyl)-(2,2-difluoro-ethyl)-amino]-pyrazine-2-carboxylic acid methyl ester. 1H-NMR (400 MHz, CDCl$_3$): 8.61 (d, 1H), 8.53 (d, 1H), 7.61-7.69 (m, 2H), 7.41-7.48 (m, 2H), 6.00-6.30 (tt, 1H), 4.63 (s, 2H), 4.27-4.35 (dt, 2H), 3.99 (s, 3H) ppm.

3-[(2-Trifluoromethylthio-phenylmethanesulfonyl)-(2,2-difluoro-ethyl)-amino]-pyrazine-2-carboxylic acid methyl ester. 1H-NMR (400 MHz, CDCl$_3$): 8.62 (d, 1H), 8.55 (d, 1H), 7.77-7.79 (m, 1H), 7.59-7.62 (m, 1H), 7.40-7.49 (m, 2H), 5.98-6.27 (tt, 1H), 4.78 (s, 2H), 4.19-4.27 (m, 2H), 4.00 (s, 3H) ppm.

Example 2.7

Preparation of 3-[(2,4-dichloro-phenylmethanesulfonyl)-(2,2,2-trifluoro-ethyl)-amino]-pyrazine-2-carboxylic acid methyl ester and 3-(2,4-dichloro-phenyl)-4-(2,2,2-trifluoro-ethoxy)-1-(2,2,2-trifluoro-ethyl)-1H-2-thia-1,5,8-triaza-naphthalene 2,2-dioxide (Compound No. C106 of Table C)

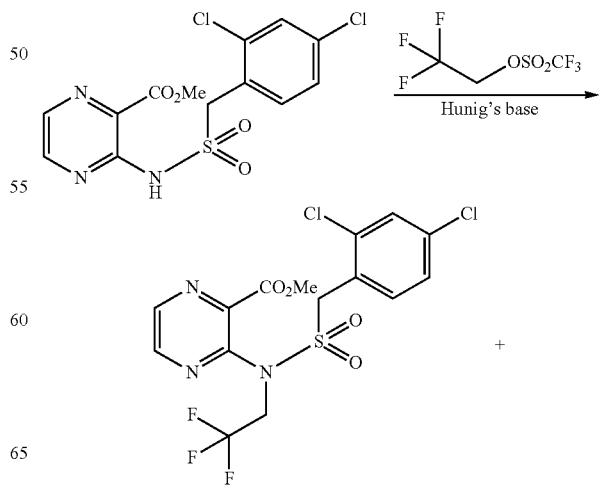

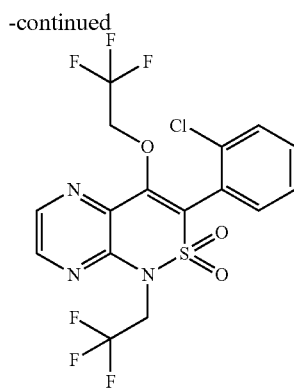

To a solution of 3-(2,4-dichloro-phenylmethanesulfonylamino)-pyrazine-2-carboxylic acid methyl ester (Example 2.1) (0.1 g) in acetonitrile (1 ml) was added N,N-diisopropylethylamine ("Hunig's base") (0.051 ml) and 2,2,2-trifluoroethyltrifluoromethanesulfonate (0.123 g). The reaction mixture was heated in a microwave at 120° C. for 25 minutes. The reaction mixture was allowed to cool to ambient temperature and then concentrated. The residue was purified by column chromatography on silica gel (eluent: iso-hexane/ethyl acetate 4:1) to give 3-[(2,4-dichloro-phenylmethanesulfonyl)-(2,2,2-trifluoro-ethyl)-amino]-pyrazine-2-carboxylic acid methyl ester (0.024 g). 1H-NMR (400 MHz, CDCl$_3$): 8.70 (d, 1H), 8.56 (d, 1H), 7.50 (s, 1H), 7.40-7.42 (m, 1H), 7.20-7.23 (m, 1H), 4.74 (s, 2H), 4.59-4.69 (m, 2H), 4.05 (s, 3H) ppm.

A cyclized by-product, Compound No. C106 of Table C, was also isolated (0.046 g).

Example 2.8

Preparation of 3-[(2-chloro-5-trifluoromethylphenylmethanesulfonyl)-(2,2-dichloro-ethyl)-amino]-pyrazine-2-carboxylic acid methyl ester

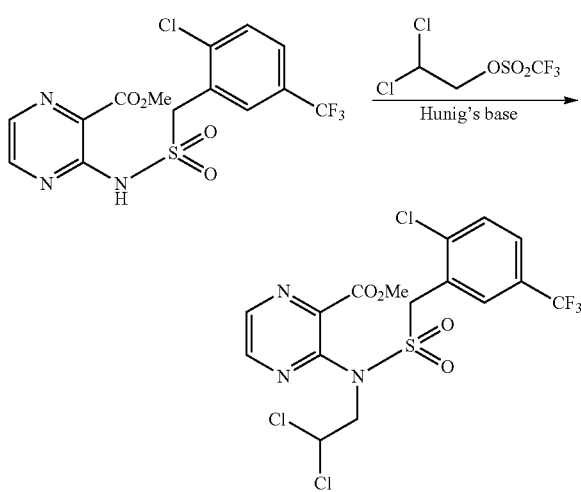

To a solution of 3-(2-chloro-5-trifluoromethyl-phenylmethanesulfonylamino)-pyrazine-2-carboxylic acid methyl ester (Example 2.1) (0.5 g) in acetonitrile (5 ml) was added N,N-diisopropylethylamine ("Hunig's base") (0.71 ml) at ambient temperature. The mixture was stirred for 5 minutes at ambient temperature before dropwise addition of 2,2-dichloroethyltrifluoromethanesulfonate (0.603 g) at ambient temperature. The reaction mixture was stirred at ambient temperature for 20 hours. The reaction mixture was concentrated and the residue purified by column chromatography on silica gel (eluent: iso-hexane/ethyl acetate 4:1) to give 3-[(2-chloro-5-trifluoromethyl-phenylmethanesulfonyl)-(2,2-dichloro-ethyl)-amino]-pyrazine-2-carboxylic acid methyl ester as a white solid (0.179 g). 1H-NMR (400 MHz, CDCl$_3$): 8.61 (d, 1H), 8.51 (d, 1H), 7.73 (s, 1H), 7.53-7.59 (m, 2H), 5.99-6.02 (m, 1H), 4.71 (s, 2H), 4.58 (d, 2H), 4.02 (s, 3H) ppm.

Example 2.9

Preparation of 3-[(2-nitro-phenylmethanesulfonyl)-prop-2-ynyl-amino]-pyrazine-2-carboxylic acid methyl ester

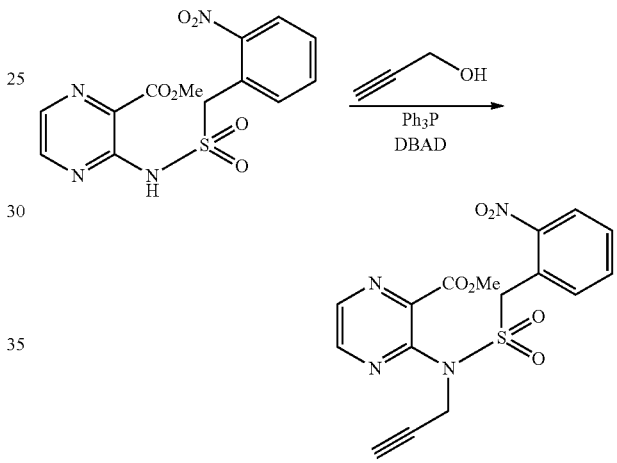

To a solution of 3-(2-nitro-phenylmethanesulfonylamino)-pyrazine-2-carboxylic acid methyl ester (Example 2.1) (0.5 g) in tetrahydrofuran (7 ml) was added polymer bound triphenyl phosphine (0.388 g) and prop-2-yn-1-ol (0.066 g) at ambient temperature. The mixture was cooled to 0-5° C. under nitrogen atmosphere and di-tert-butyl azodicarboxylate ("DBAD") was added dropwise. The reaction mixture was allowed to warm slowly to ambient temperature and stirred for 20 hours. Further polymer bound triphenyl phosphine (0.9 g) was added and the reaction mixture stirred at ambient temperature for a further 72 hours. The reaction was filtered to remove the polymer and concentrated. The residue was purified by column chromatography on silica gel (eluent: iso-hexane/ethyl acetate 3:1) to give 3-[(2-nitro-phenylmethanesulfonyl)-prop-2-ynyl-amino]-pyrazine-2-carboxylic acid methyl ester (0.131 g). 1H-NMR (400 MHz, CDCl$_3$): 8.64 (s, 2H), 7.99 (d, 1H), 7.48-7.64 (m, 3H), 5.29 (s, 2H), 4.60 (s, 2H), 3.96 (s, 3H), 2.35 (t, 1H) ppm.

The following compound was made using the same method:

3-[(2,5-Dichloro-6-trifluoromethyl-phenylmethanesulfonyl)-prop-2-ynyl-amino]-pyrazine-2-carboxylic acid methyl ester. 1H-NMR (400 MHz, CDCl$_3$): 8.69 (s, 2H), 7.54-7.59 (m, 2H), 5.31 (s, 2H), 4.79 (d, 2H), 3.98 (s, 3H), 2.40 (t, 1H) ppm.

The following compound was made using the same method with but-2-yn-1-ol as reagent:

3-[(2,5-Dichloro-6-trifluoromethyl-phenylmethanesulfonyl)-but-2-ynyl-amino]-pyrazine-2-carboxylic acid methyl ester. 1H-NMR (400 MHz, CDCl$_3$): 8.69-8.71 (m, 2H), 7.57-7.62 (m, 2H), 5.36 (s, 2H), 4.73-4.74 (m, 2H), 4.01 (s, 3H), 1.80 (t, 1H) ppm.

The following compound was made using the same method with prop-2-en-1-ol as reagent:

3-[(5-Chloro-2-trifluoromethyl-phenylmethanesulfonyl)-prop-2-en-amino]-pyrazine-2-carboxylic acid methyl ester. 1H-NMR (400 MHz, CDCl$_3$): 8.62 (d, 1H), 8.59 (d, 1H), 7.69 (s, 1H), 7.63 (d, 1H), 7.42 (d, 1H), 5.92-6.02 (m, 1H), 5.17-5.33 (m, 2H), 4.62 (s, 2H), 4.57-4.58 (d, 2H), 4.02 (s, 3H) ppm.

The following compound was made using the same method with 2-methyl-prop-2-en-1-ol as reagent:

3-[(2,3-Dichloro-phenylmethanesulfonyl)-(2-methyl-allyl)-amino]-pyrazine-2-carboxylic acid methyl ester. 1H-NMR (400 MHz, CDCl$_3$): 8.50 (d, 1H), 8.49 (d, 1H), 7.41 (d, 1H), 7.36 (d, 1H), 7.11 (t, 1H), 5.01 (s, 1H), 4.85 (s, 1H), 4.69 (s, 2H), 4.60 (s, 2H), 4.00 (s, 3H), 1.87 (s, 3H) ppm.

Example 2.10

Preparation of 3-(2-chloro-5-trifluoromethyl-phenyl)-1-(2,2-difluoro-ethyl)-2,2-dioxo-1,2-dihydro-2-λ-6-thia-1,5,8-triaza-naphthalen-4-ol (Compound No. D16 of Table D)

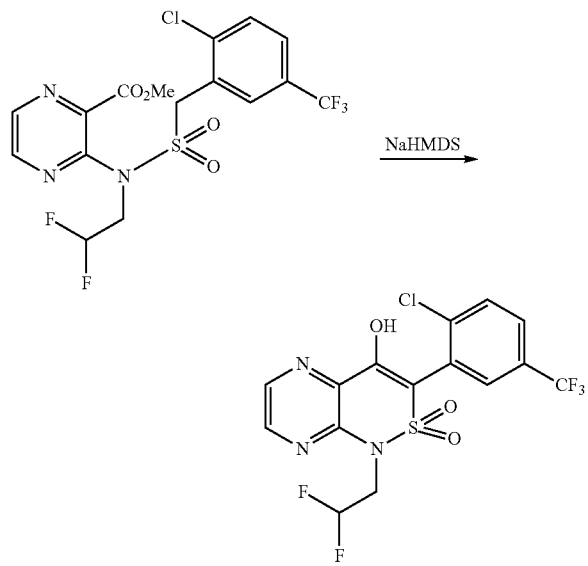

To a solution of 3-[(2-chloro-5-trifluoromethyl-phenylmethanesulfonyl)-(2,2-difluoro-ethyl)-amino]-pyrazine-2-carboxylic acid methyl ester (Example 2.6) (186 mg) in tetrahydrofuran (7.1 ml) under nitrogen atmosphere was added in portions a solution of sodium hexamethyldisilazide ("NaHMDS") (0.97 ml) (1M in THF) at ambient temperature. The reaction mixture was stirred for 3 hours at ambient temperature. The reaction mixture was acidified by addition of aqueous hydrochloric acid (1M) (5 ml). The phases were separated and the aqueous phase extracted with ethyl acetate. The combined organic extracts were washed three times with de-ionized water, dried over magnesium sulfate and concentrated to give Compound No. D16 of Table D (172 mg) as a pale orange oil which crystallized on standing.

The following compounds were made using the same method: Compound Nos. D1-D8, D10-D15, D17-D19, and D21-D60 of Table D.

On one occasion some rearrangement of the propargyl group occurred which resulted in the formation a propa-1,2-dien-1-yl group. The isomers could not be separated by column chromatography and were isolated as a 1:1 mixture. Consequently, Compound No. D40 of Table D is a 1:1 mixture of 3-(2-nitro-phenyl)-2,2-dioxo-1-prop-2-ynyl-1,2-dihydro-2-λ-6-thia-1,5,8-triaza-naphthalen-4-ol and 3-(2-nitro-phenyl)-2,2-dioxo-1-propa-1,2-dienyl-1,2-dihydro-2-λ-6-thia-1,5,8-triaza-naphthalen-4-ol.

On one occasion some transesterification of an ethyl ester group occurred which resulted in a mixture of compounds being isolated which could not be separated by column chromatography. Consequently, Compound No. D58 of Table D is a 3:1 mixture of 2-[1-(3,3-difluoro-propyl)-4-hydroxy-2,2-dioxo-1,2-dihydro-2-λ-6-thia-1,5,8-triaza-naphthalen-3-yl]-6-trifluoromethyl-nicotinic acid ethyl ester and 2-[1-(3,3-difluoro-propyl)-4-hydroxy-2,2-dioxo-1,2-dihydro-2-λ-6-thia-1,5,8-triaza-naphthalen-3-yl]-6-trifluoromethyl-nicotinic acid methyl ester.

Example 2.11

Preparation of 2,2-dimethyl-propionic acid 3-(2-chloro-5-trifluoromethyl-phenyl)-1-(2,2-difluoro-ethyl)-2,2-dioxo-1,2-dihydro-2-λ-6-thia-1,5,8-triaza-naphthalen-4-yl ester (Compound No. C34 of Table C)

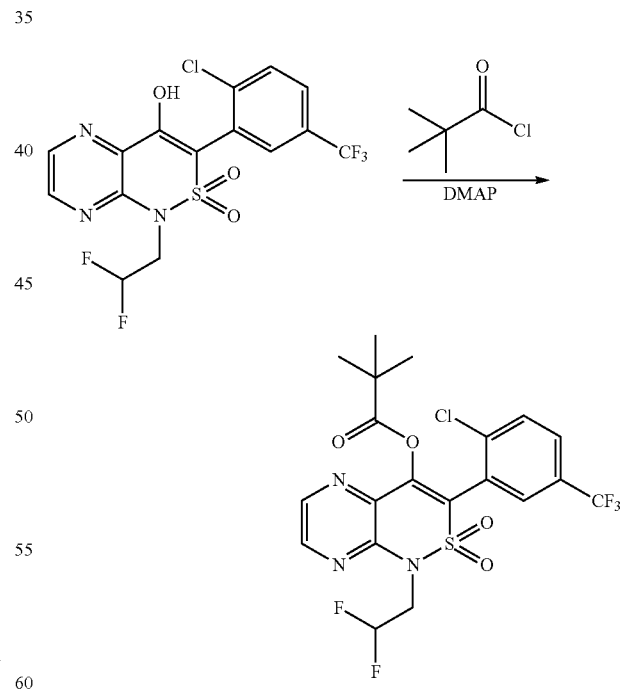

To a solution of Compound No. D16 of Table D (Example 2.10) (110 mg) in acetonitrile (1.6 ml) was added 4-dimethylaminopyridine ("DMAP") (5 mg) followed by 2,2-dimethylpropionyl chloride (65 pd). The reaction mixture was heated in a microwave at 150° C. for 1500 seconds. The reaction mixture was concentrated and the residue purified by column chromatography on silica gel (eluent: ethyl acetate/ hexane 1:9) to give Compound No. C34 of Table C (71 mg).

Example 2.12

Preparation of isobutyric acid 1-ethyl-2,2-dioxo-3-(2-trifluoromethyl-sulfanyl-phenyl)-1,2-dihydro-2-λ-6-thia-1,5,8-triaza-naphthalen-4-yl ester (Compound No. C19 of Table C)

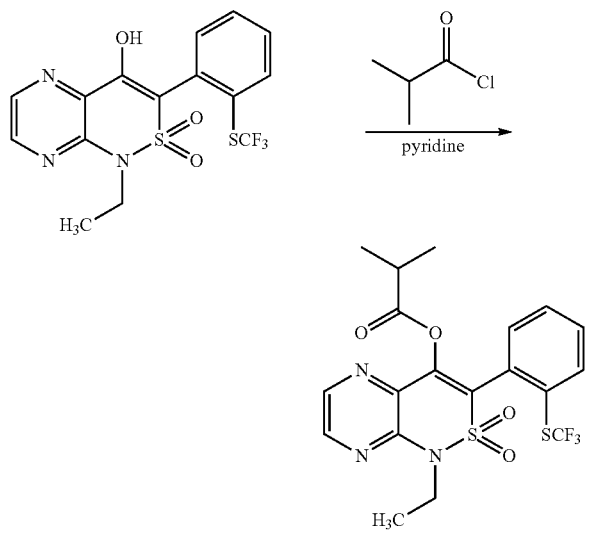

To a solution of Compound No. D7 of Table D (Example 2.10) (110 mg) in dichloromethane (5 ml) was added pyridine (33 μl) followed by isobutyryl chloride (35 μl). The reaction mixture was stirred at ambient temperature for 3 hours. The reaction mixture was concentrated and the residue purified by column chromatography on silica gel (eluent: ethyl acetate/ hexane 15:85) to give Compound No. C19 of Table C (91 mg).

Example 2.13

Preparation of carbonic acid 1-(2,2-difluoro-ethyl)-3-(5-methyl-2-trifluoromethyl-phenyl)-2,2-dioxo-1,2-dihydro-2-λ-6-thia-1,5,8-triaza-naphthalen-4-yl ester ethyl ester (Compound No. C147 of Table C)

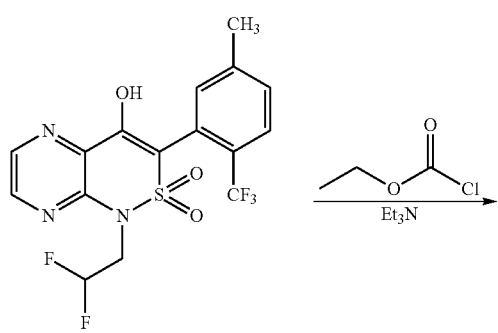

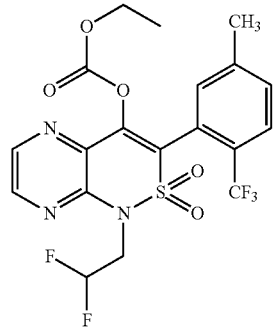

To a solution of Compound No. D41 of Table D (Example 2.10) (190 mg) in dichloromethane (5 ml) was added triethylamine (95 μl) followed by ethyl chloroformate (52 μl). The reaction mixture was stirred at ambient temperature for 3 hours. The reaction mixture was concentrated and the residue purified by column chromatography on silica gel (eluent: ethyl acetate/hexane 15:85) to give Compound No. C147 of Table C (205 mg).

The following compounds were made using one of the methods as described in Example 2.11, Example 2.12, or Example 2.13 using isobutyryl chloride, 2,2-dimethylpropionyl chloride, cyclopropanecarbonyl chloride, ethyl chloroformate, S-methyl chlorothioformate, S-ethyl chlorothioformate or S-phenyl chlorothioformate as reagent: Compound Nos. C1-C2, C4, C9, C14-C18, C20-C28, C30-C33, C35-C39, C41, C43-C47, C49-055, C57, C59-C82, C84-C94, C96-C105, C107-C115, C117-C120, C124-C135, C139-C146, and C148-C149 of Table C.

On one occasion an impurity of starting material resulted in a mixture of tert-butylcarbonyloxy- and methoxy-compounds being isolated. Compound Nos. C40 and C41 of Table C were separated using column chromatography.

On one occasion some elimination occurred from the 2,2-dichloro-ethyl group which resulted in the formation of an (E,Z)-2-chloro-vinyl group. Compound Nos. C114 and C115 of Table C were separated using column chromatography.

On one occasion some transesterification of an ethyl ester group occurred which resulted in a mixture of compounds being isolated which could not be separated by column chromatography. Consequently, Compound No. C139 of Table C is a 2:1 mixture of 2-[1-(3,3-difluoro-propyl)-4-methylsulfanylcarbonyloxy-2,2-dioxo-1,2-dihydro-2-λ-6-thia-1,5,8-triaza-naphthalen-3-yl]-6-trifluoromethyl-nicotinic acid ethyl ester and 2-[1-(3,3-difluoro-propyl)-4-methylsulfanylcarbonyloxy-2,2-dioxo-1,2-dihydro-2-λ-6-thia-1,5,8-triaza-naphthalen-3-yl]-6-trifluoromethyl-nicotinic acid methyl ester.

3. Reactions that are Covered by Scheme 3

Example 3.1

Preparation of 3-(2-chloro-3,6-difluoro-phenyl)-2,2-dioxo-1,2-dihydro-2-λ-6-thia-1,5,8-triaza-naphthalen-4-ol (Compound No. A2 of Table A)

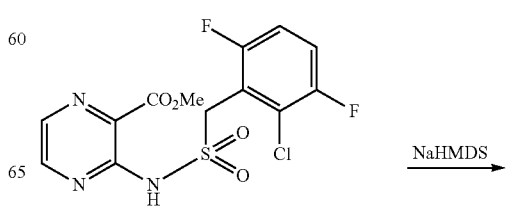

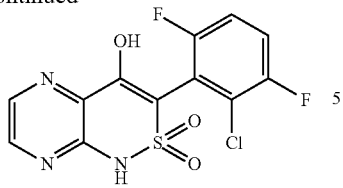

3-(2-Chloro-3,6-difluoro-phenylmethanesulfonylamino)-pyrazine-2-carboxylic acid methyl ester (Example 2.1) (480 mg) was dissolved in N,N-dimethylformamide (7.5 ml) and heated, under a nitrogen atmosphere, to 40° C. in order to obtain a complete solution. Sodium hexamethyldisilazide ("NaHMDS") (3.9 ml) (1M in THF) was added in one portion. The reaction mixture was heated to 40° C. for 5 hours and then stored at ambient temperature for 16 hours. The reaction mixture was partitioned between water and dichloromethane. The phases were separated. The aqueous layer was washed with dichloromethane. The aqueous layer was acidified with aqueous hydrochloric acid (2M) to give a yellow solid. The solid was isolated by filtration, washed with water and dried under vacuum at 50° C. to give Compound No. A2 of Table A (375 mg) as a yellow solid.

The following compounds were made using the same method: Compound Nos. A1 and A3-A6 of Table A.

Example 3.2

Preparation of 2,2-dimethyl-propionic acid-3-(2-chloro-3,6-difluoro-phenyl)-2,2-dioxo-1,2-dihydro-2-λ-6-thia-1,5,8-triaza-naphthalen-4-yl ester (Compound No. B3 of Table B)

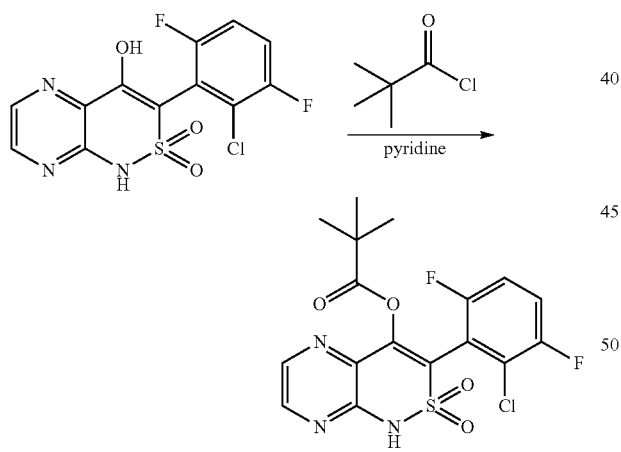

To a suspension of Compound No. A2 (Example 3.1) in dichloromethane (10 ml) was added pyridine (0.205 ml) followed by 2,2-dimethylpropionyl chloride (0.15 ml). The reaction mixture was heated to 40° C. for 4 hours and then stored at ambient temperature of 16 hours. The reaction mixture was partition between dichloromethane (30 ml) and aqueous hydrochloric acid (2M) (30 ml). The phases were separated. The aqueous layer was extracted with ethyl acetate. The combined organic extracts were concentrated. The residue was triturated with iso-hexane and dried under vacuum to give Compound No. B3 of Table B (408 mg) as a yellow solid.

The following compounds were made using the same method: Compound Nos. B1-B2 and B4-B6 of Table B.

4. Reactions that are Covered by Scheme 4

Example 4.1

Preparation of 2,2-dimethyl-propionic acid-3-(2,4-dichloro-phenyl)-1-(2,2-difluoroethyl)-2,2-dioxo-1,2-dihydro-2-λ-6-thia-1,5,8-triaza-naphthalen-4-yl ester (Compound No. C12 of Table C) and 2,2-dimethylpropionic acid-3-(2,4-dichloro-phenyl)-8-(2,2-difluoroethyl)-2,2-dioxo-2,8-dihydro-2-λ-6-thia-1,5,8-triaza-naphthalen-4-yl ester

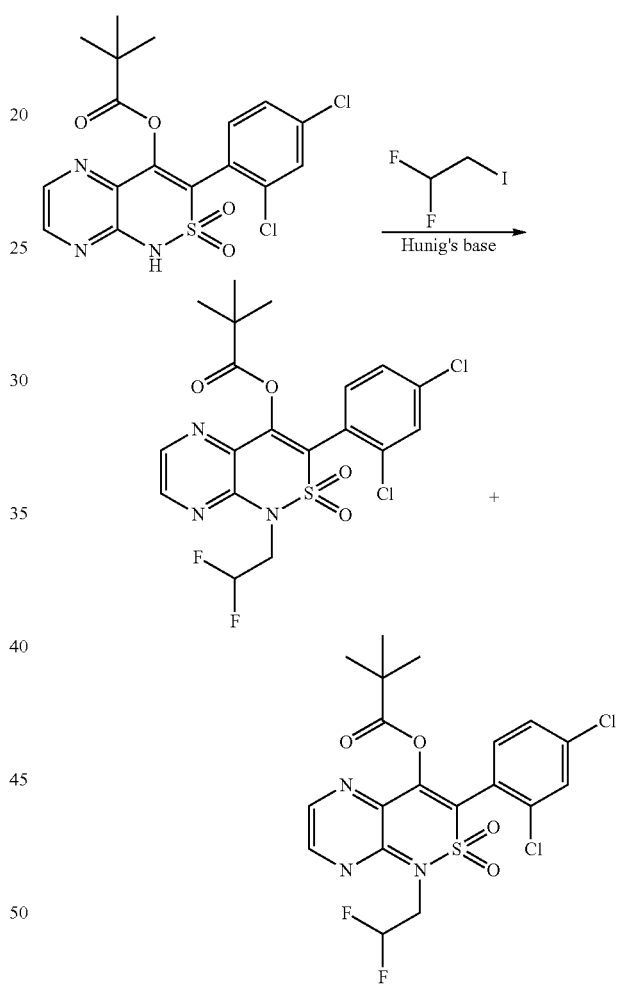

To a solution of Compound No. B1 of Table B (Example 3.2) (250 mg) in acetonitrile (4 ml) was added N,N-diisopropylethylamine ("Hunig's base") (0.2 ml) and 1,1-difluoro-2-iodoethane (224 mg). The reaction mixture was heated in a microwave at 130° C. for 1500 seconds. The reaction mixture was concentrated and the residue purified by column chromatography on silica gel (eluent: ethyl acetate/dichloromethane 0:10 to 1:9) to give Compound No. C12 of Table C (7 mg).

The other isomer, 2,2-dimethylpropionic acid-3-(2,4-dichloro-phenyl)-8-(2,2-difluoroethyl)-2,2-dioxo-2,8-dihydro-2-λ-6-thia-1,5,8-triaza-naphthalen-4-yl ester, was also isolated (9 mg). 1H-NMR (400 MHz, CDCl$_3$): 7.84 (d, 1H), 7.52-7.54 (m, 2H), 7.41-7.42 (m, 1H), 7.33-7.36 (m, 1H), 6.24-6.53 (tt, 1H), 4.56-4.65 (m, 2H), 1.10 (s, 9H) ppm.

The following compounds were made using the same method: Compound Nos. C5-C8, C10-C11, C13, C116, and C121-C123 of Table C.

Example 4.2

Preparation of 3-(2,3-dichloro-6-fluoro-phenyl)-1-(2,2-difluoro-ethyl)-2,2-dioxo-1,2-dihydro-2-λ-6-thia-1,5,8-triaza-naphthalen-4-ol (Compound No. D9 of Table D)

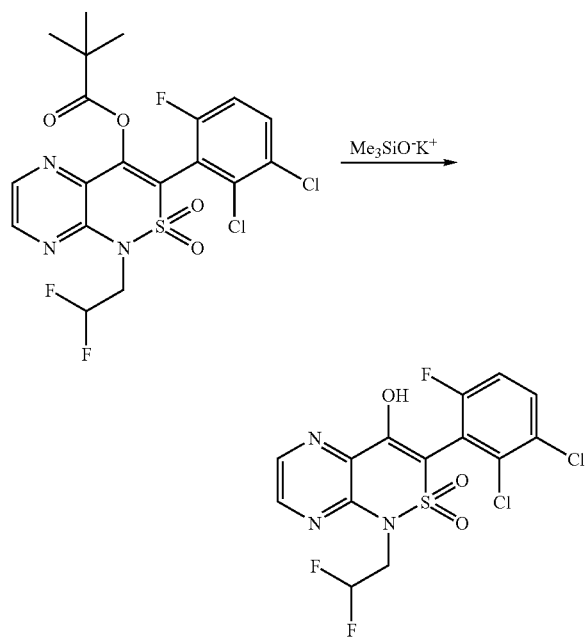

To a solution of Compound No. C20 of Table C (Example 2.8) (110 mg) in tetrahydrofuran (5 ml) was added potassium trimethylsilanolate (40 mg). The reaction mixture was stirred at ambient temperature for 16 hours. The reaction mixture was acidified by addition of glacial acetic acid. The mixture was concentrated and the residue purified by column chromatography on silica gel (eluent: ethyl acetate/hexane 15:85 to 100:0) to give Compound No. D9 of Table D (68 mg).

Example 4.3

Preparation of 3-(2,4-dichloro-phenyl)-4-methoxy-1-methyl-1H-2-thia-1,5,8-triazanaphthalen-2,2-dioxide (Compound No. C3 of Table C)

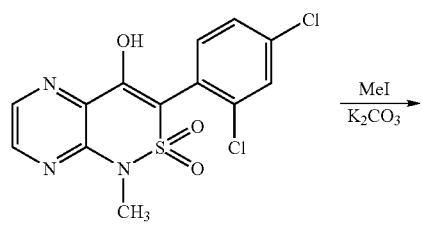

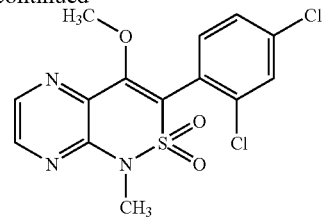

To a solution of Compound No. D1 of Table D (Example 2.7) (50.5 mg) in acetonitrile (4 ml) under a nitrogen atmosphere was added potassium carbonate (19.5 mg) followed by methyl iodide (22 mg). The reaction mixture was heated in a microwave at 150° C. for 1800 seconds. The reaction mixture was acidified by addition of aqueous hydrochloric acid (2M) and the mixture partitioned between water and dichloromethane. The phases were separated and the aqueous layer was extracted with further dichloromethane. The combined organic extracts were dried over magnesium sulfate and concentrated to give Compound No. C3 of Table C (38 mg) as a brown solid.

5. Reactions that are Covered by Scheme 5

Example 5.1

Preparation of trifluoromethanesulfonic acid-3-(4-chloro-2-trifluoromethylphenyl)-1-ethyl-2,2-dioxo-1,2-dihydro-2-λ-6-thia-1,5,8-triaza-naphthalen-4-yl ester (Compound No. C29 of Table C)

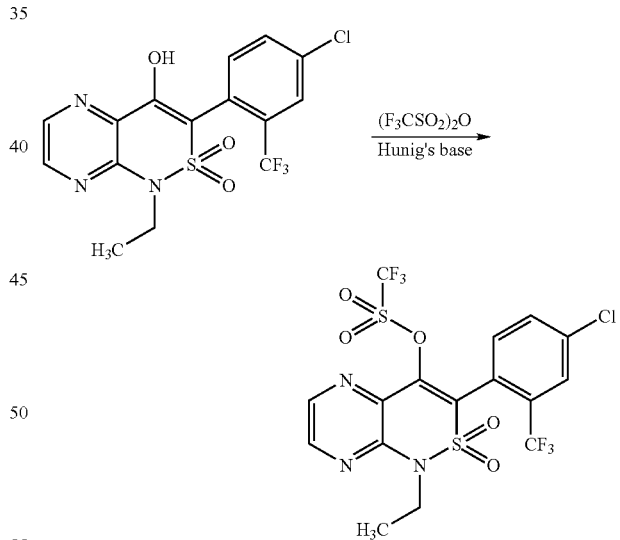

To a solution of Compound No. D10 of Table D (Example 2.7) (100 mg) in dichloromethane (2 ml) was added N,N-diisopropylethylamine ("Hunig's base") (64 μl). The reaction mixture was cooled to −78° C. and trifluoromethanesulfonic anhydride (64 μl) was added in portions over a period of 5 minutes. The reaction mixture was stirred at −78° C. for 1.5 hours and then allowed to warm to ambient temperature and stirred for a further 2 hours. The reaction mixture was quenched by addition of water. The mixture was extracted with dichloromethane. The combined organic extracts were dried over magnesium sulfate and concentrated. The residue was purified by column chromatography on silica gel (eluent: ethyl acetate/hexane 1:4) to give Compound No. C29 of Table C (15 mg) a yellow solid.

Example 5.2

Preparation of methanesulfonic acid 3-(2-chloro-5-trifluoromethyl-phenyl)-1-(2,2-difluoro-ethyl)-2,2-dioxo-1,2-dihydro-2-λ-6-thia-1,5,8-triaza-naphthalen-4-yl ester (Compound No. C83 of Table C)

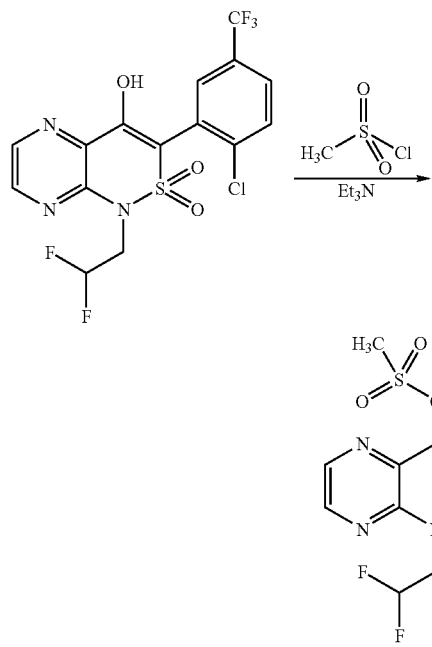

To a solution of Compound No. D16 of Table D (Example 2.7) (610 mg) in dichloromethane (20 ml) was added triethylamine (390 μl) followed by methanesulfonyl chloride (160 mg). The reaction mixture was stirred at ambient temperature for 3 hours. The reaction mixture was concentrated and the residue purified by column chromatography on silica gel (eluent: dichloromethane) to give Compound No. C83 of Table C (595 mg).

The following compound was made using the same method: Compound No. C95 of Table C.

6. Reactions which are Covered by Scheme 6

Example 6.1

Preparation of 1-bromo-3-bromomethyl-2-chloro-4-fluoro-benzene

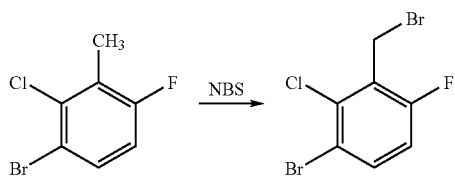

A mixture of 3-bromo-2-chloro-6-fluoro-toluene (commercially available) (8.0 g), N-bromosuccinimide ("NBS") (6.42 g) and benzoyl peroxide (catalytic amount) in carbon tetrachloride (40 ml) was heated to reflux. A 500 watt tungsten halogen lamp was used to initiate the reaction. The reaction mixture was heated to reflux and irradiated for 30 minutes. The reaction mixture was allowed to cool to ambient temperature and then filtered. The filtrate was concentrated to give a colorless oil which solidified on standing to give 1-bromo-3-bromomethyl-2-chloro-4-fluoro-benzene as an off-white solid (10.7 g). 1H-NMR (400 MHz, CDCl$_3$): 7.58 (dd, 1H), 6.94 (t, 1H), 4.64 (d, 21-1) ppm.

7. Reactions that are Covered by Scheme 7

Example 7.1

Preparation of 2,2-dimethylpropionic acid-3-(2,3'-dichloro-4-fluoro-biphenyl-3-yl)-1-(2,2-difluoroethyl)-2,2-dioxo-1,2-dihydro-2-λ-6-thia-1,5,8-triaza-naphthalen-4-yl ester (Compound No. C42 of Table C)

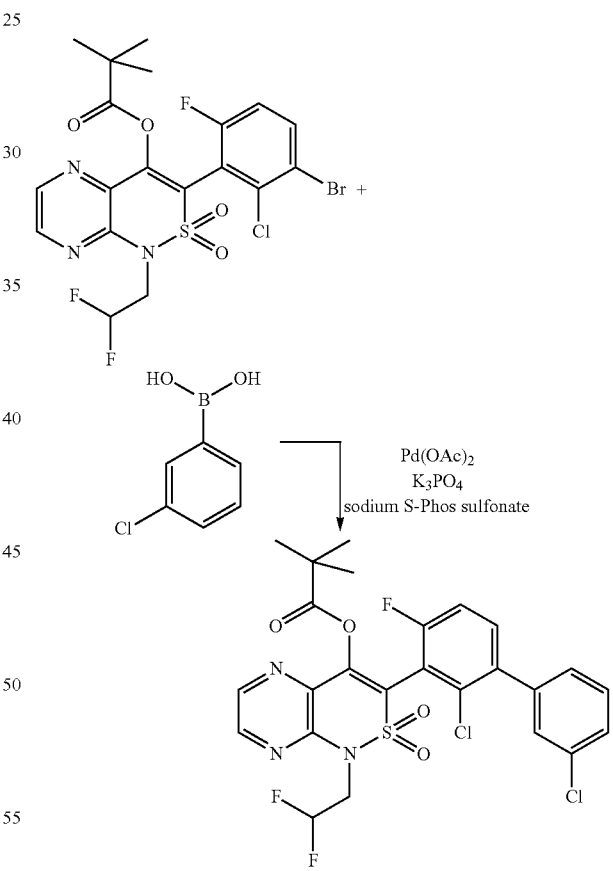

To Compound No. C35 of Table C (0.089 g) was added successively 3-chloro-phenyl boronic acid (0.038 g), palladium(II) acetate (0.0072 g), 2'-dicyclohexyl-phosphino-2,6-dimethoxy-3-sulfonato-1,1'-biphenyl hydrate sodium salt ("sodium S-Phos sulfonate") (0.012 g) and toluene (1 ml). To this mixture was added a solution of potassium phosphate (0.070 g) in degassed water (0.2 ml). The mixture was pre-stirred at ambient temperature for 3 minutes and then heated in a microwave at 110° C. for 900 seconds. The reaction mixture was diluted with ethyl acetate and washed with aqueous hydrochloric acid (2M). The organic phase was dried over magnesium sulfate and concentrated. The residue was purified by reverse phase column chromatography to give Compound No. C42 of Table C (15 mg).

The following compounds were made using the same method: Compound Nos. C56 and C142 of Table C, and Compound No. D₂O of Table D.

8. Reactions that are Covered by Scheme 8

Example 8.1

Preparation of C-(2,4-dichloro-phenyl)-N-(2-fluoro-ethyl)-methanesulfonamide

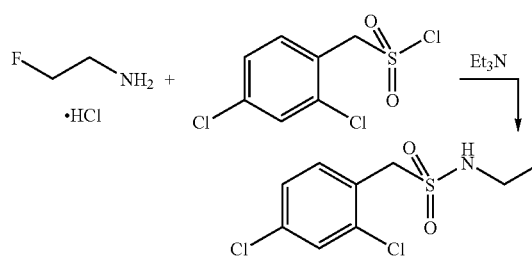

To a suspension of 2-fluoroethylamine hydrochloride (0.287 g) in dichloro-methane (4 ml) was added triethylamine (0.4 ml) followed by (2,4-dichloro-phenyl)-methanesulfonyl chloride (Example 1.2) (0.25 g). The reaction mixture was stirred at ambient temperature for 3 hours then left to stand at ambient temperature for 16 hours. Dichloromethane (20 ml) was added to the reaction mixture and the mixture was washed with water (20 ml). The phases were separated and the organic layer was dried over magnesium sulfate and concentrated to give C-(2,4-dichloro-phenyl)-N-(2-fluoro-ethyl)-methanesulfonamide (15 mg) (60% pure). 1H-NMR (400 MHz, CDCl₃): 7.47-7.51 (m, 2H), 7.29-7.32 (dd, 1H), 4.77 (bs, 1H), 4.49 (s, 2H), 4.51-4.53 (m, 1H), 4.39-4.42 (m, 1H), 3.33-3.36 (m, 1H), 3.27-3.29 (m, 1H) ppm.

Example 8.2

Preparation of isobutyric acid 3-(2,4-dichloro-phenyl)-1-(2-fluoroethyl)-2,2-dioxo-1,2-dihydro-2-λ-6-thia-1,5,8-triaza-naphthalen-4-yl ester (Compound No. C58 of Table C)

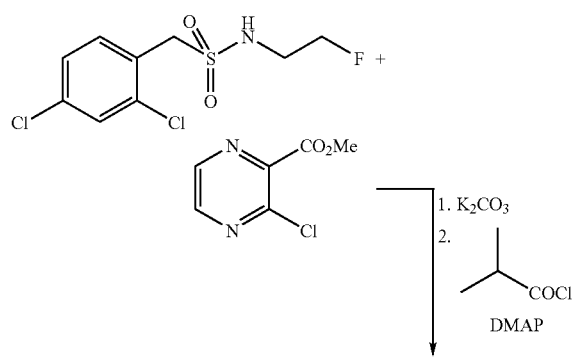

-continued

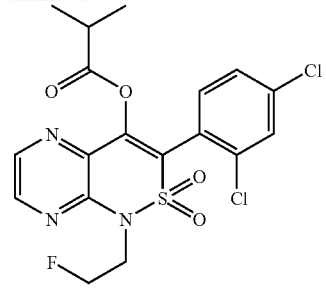

To C-(2,4-dichloro-phenyl)-N-(2-fluoro-ethyl)-methanesulfonamide (Example 8.1) (0.231 g) was added successively 3-chloro-pyrazine-2-carboxylic acid methyl ester (0.151 g), potassium carbonate (0.446 g) and N,N-dimethylformamide (2 ml). The reaction mixture was heated in a microwave for 25 minutes at 120° C. The reaction mixture was diluted with ethyl acetate and washed with aqueous hydrochloric acid (2M). The organic extracts were dried over magnesium sulfate and concentrated. The residue was dissolved in acetonitrile (1 ml) and 4-dimethylaminopyridine ("DMAP") (1 mg) and 2,2-dimethylpropionyl chloride (7 µl) were added. The reaction mixture was heated in a microwave at 120° C. for 25 minutes. The reaction mixture was concentrated and the residue purified by column chromatography on silica gel (eluent: ethyl acetate/hexane 15:85) to give Compound No. C58 of Table C (21 mg).

9. Reactions that are Covered by Scheme 9

Example 9.1

Preparation of 3-methoxylcarbonylmethanesulfonylamino-pyrazine-2-carboxylic acid methyl ester

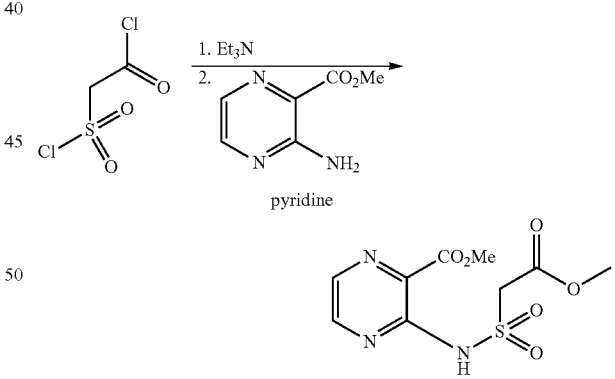

A solution of chlorosulfonylacetyl chloride (3.0 g) in dichloromethane (18 ml) was cooled to 0-5° C. and a mixture of methanol (0.83 ml) and triethylamine (2.87 ml) in dichloromethane was added dropwise. The reaction mixture was stirred at 0-5° C. for one hour and then at ambient temperature for a further hour. 3-Amino-pyrazine-2-carboxylic acid methyl ester (2.34 g) was added followed by dropwise addition of a solution of pyridine (6 ml) in dichloromethane (10 ml) over a period of 5 minutes at ambient temperature. The reaction mixture was stirred at ambient temperature for 23 hours. Dichloromethane (50 ml) was added to the reaction mixture and the mixture was washed with aqueous hydrochloric acid (2M) (4×30 ml). The phases were separated and the organic layer was concentrated. The residue was purified by column chromatography on silica gel (eluent: ethyl acetate/dichloromethane from 0:10 to 1:9) to give 3-methoxy-carbonylmethanesulfonylamino-pyrazine-2-carboxylic acid methyl ester (1.212 g). 1H-NMR (400 MHz, CDCl$_3$): 10.52 (s, 1H), 8.53 (d, 1H), 8.45 (d, 1H), 4.64 (s, 2H), 4.07 (s, 3H), 3.80 (s, 3H) ppm.

The following compound was made using the same method:

3-tert-Butoxycarbonylmethanesulfonylamino-pyrazine-2-carboxylic acid methyl ester. 1H-NMR (400 MHz, CDCl$_3$): 10.47 (s, 1H), 8.53 (s, 1H), 8.44 (s, 1H), 4.52 (s, 2H), 4.07 (s, 3H), 1.45 (s, 9H) ppm.

Example 9.2

Preparation of 3-[(2,2-difluoro-ethyl)-methoxycarbonylmethanesulfonylamino]-pyrazine-2-carboxylic acid methyl ester

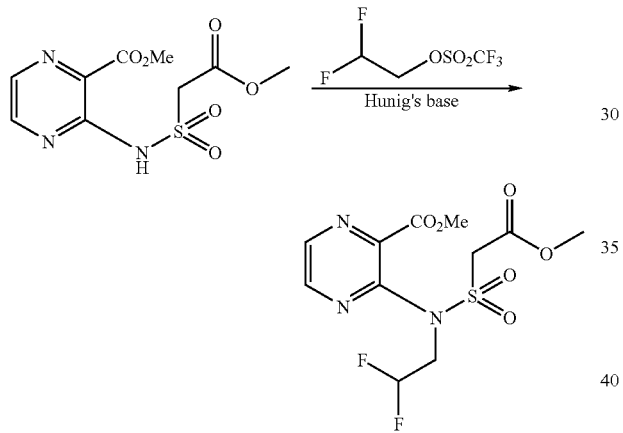

To a solution of 3-methoxycarbonylmethanesulfonylamino-pyrazine-2-carboxylic acid methyl ester (Example 9.1) (1.212 g) in acetonitrile (12 ml) was added N,N-diisopropylethylamine ("Hunig's base") (0.8 ml) at ambient temperature. The mixture was stirred at ambient temperature for 5 minutes before dropwise addition of a solution of 2,2-difluoroethyltrifluoromethanesulfonate (0.978 g) in acetonitrile (5 ml) at ambient temperature. The reaction mixture was stirred at ambient temperature for 20 hours. The reaction mixture was concentrated and the residue partitioned between ethyl acetate (30 ml) and aqueous sulfuric acid (2M) (30 ml). The phases were separated and the organic layer was concentrated. The residue was purified by column chromatography on silica gel (eluent: ethyl acetate/hexane 1:2) to give 3-[(2,2-difluoro-ethyl)-methoxycarbonyl-methanesulfonyl-amino]-pyrazine-2-carboxylic acid methyl ester (0.819 g). 1H-NMR (400 MHz, CDCl$_3$): 8.70 (d, 1H), 8.65 (d, 1H), 6.06-6.29 (m, 1H), 4.32-4.38 (m, 2H), 4.18 (s, 2H), 4.02 (s, 3H), 3.78 (s, 3H) ppm.

The following compound was made using the same method:

3-[tert-Butoxycarbonylmethanesulfonyl-(2,2-difluoroethyl)-amino]-pyrazine-2-carboxylic acid methyl ester. 1H-NMR (400 MHz, CDCl$_3$): 8.69 (s, 1H), 8.65 (s, 1H), 6.18 (tt, 1H), 4.31-4.39 (m, 2H), 4.04 (s, 2H), 4.02 (s, 3H), 1.48 (s, 9H) ppm.

Example 9.3

Preparation of 1-(2,2-difluoro-ethyl)-4-hydroxy-2,2-dioxo-1,2-dihydro-2-λ-6-thia-1,5,8-triaza-naphthalene-3-carboxylic acid methyl ester

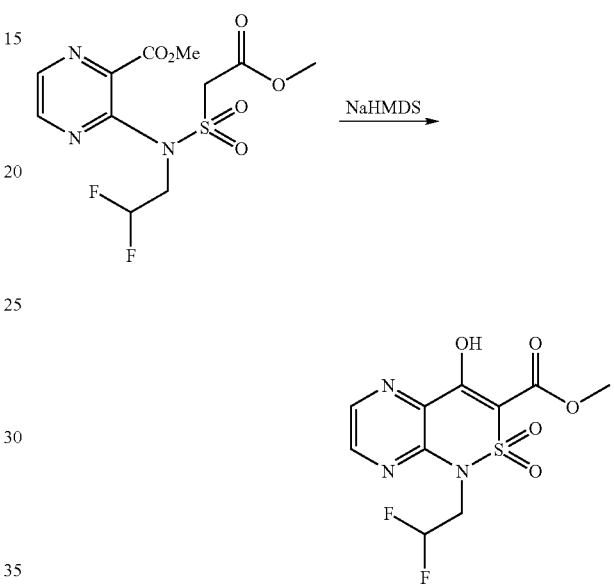

To a solution of 3-[(2,2-difluoro-ethyl)-methoxycarbonyl-methanesulfonyl-amino]-pyrazine-2-carboxylic acid methyl ester (Example 9.2) (0.819 g) in tetrahydrofuran (40 ml) under nitrogen atmosphere was added in portions a solution of sodium hexamethyldisilazide ("NaHMDS") (5.8 ml) (1M in THF) at ambient temperature. The reaction mixture was stirred for 3 hours at ambient temperature. The reaction was quenched by addition of glacial acetic acid and the mixture was concentrated. The residue was partitioned between ethyl acetate (30 ml) and aqueous hydrochloric acid (2M) (15 ml). The phases were separated and the organic layer was concentrated to give 1-(2,2-difluoro-ethyl)-4-hydroxy-2,2-dioxo-1,2-dihydro-2-λ-6-thia-1,5,8-triaza-naphthalene-3-carboxylic acid methyl ester (0.520 g). 1H-NMR (400 MHz, CDCl$_3$): 8.65 (d, 1H), 8.59 (d, 1H), 6.02-6.32 (m, 1H), 4.60-4.67 (m, 2H), 4.13 (s, 3H) ppm.

The following compounds were made using the same method:

1-(2,2-Difluoro-ethyl)-4-hydroxy-2,2-dioxo-1,2-dihydro-2-λ-6-thia-1,5,8-triaza-naphthalene-3-carboxylic acid tert-butyl ester. 1H-NMR (400 MHz, CDCl$_3$): 8.61 (m, 1H), 8.56 (m, 1H), 6.04-6.35 (tt, 1H), 4.59-4.66 (dt, 2H), 1.67 (s, 9H) ppm.

4-Hydroxy-2,2-dioxo-1,2-dihydro-2-λ-6-thia-1,5,8-triaza-naphthalene-3-carboxylic acid ethyl ester. 1H-NMR (400 MHz, d$_6$-DMSO): 8.24 (d, 1H), 8.14 (d, 1H), 4.31 (q, 2H), 1.28 (t, 3H) ppm.

Example 9.4

Preparation of 1-(2,2-difluoro-ethyl)-2,2-dioxo-2,3-dihydro-1H-2-λ-6-thia-1,5,8-triaza-naphthalen-4-one

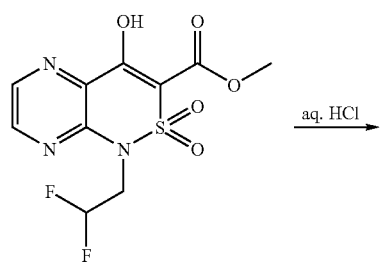

aq. HCl →

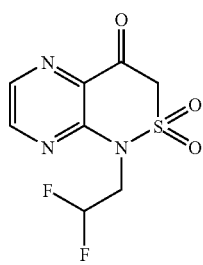

To a solution of 1-(2,2-difluoro-ethyl)-4-hydroxy-2,2-dioxo-1,2-dihydro-2-λ-6-thia-1,5,8-triaza-naphthalene-3-carboxylic acid methyl ester (0.520 g) (Example 9.3) in ethanol (3 ml) was added aqueous hydrochloric acid (2M) (1 ml). The mixture was heated in a microwave for 20 minutes at 150° C. twice. The reaction mixture was concentrated to give 1-(2,2-difluoro-ethyl)-2,2-dioxo-2,3-dihydro-1H-2-λ-6-thia-1,5,8-triaza-naphthalen-4-one (0.203 g). 1H-NMR (400 MHz, CDCl₃): 8.66 (d, 1H), 8.61 (d, 1H), 6.03-6.33 (m, 1H), 4.61 (s, 2H), 4.54-4.61 (m, 2H) ppm.

Example 9.5

Preparation of isobutyric acid 3-(2-chloro-4-methyl-phenyl)-1-(2,2-difluoro-ethyl)-2,2-dioxo-1,2-dihydro-2-λ-6-thia-1,5,8-triaza-naphthalen-4-yl ester (Compound No. C136 of Table C)

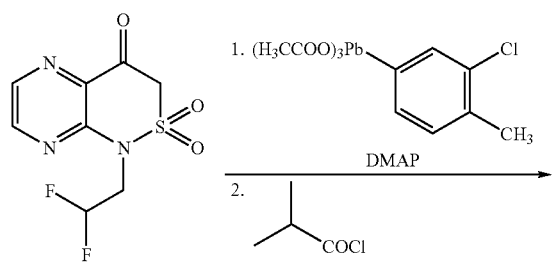

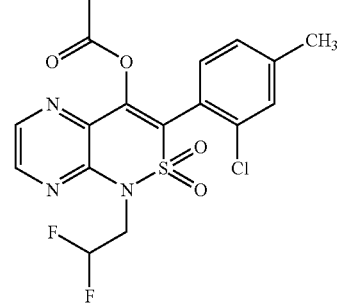

A mixture of 2-chloro-4-methyl-phenyl lead triacetate (0.153 g), 1-(2,2-difluoro-ethyl)-2,2-dioxo-2,3-dihydro-1H-2-λ-6-thia-1,5,8-triaza-naphthalen-4-one (Example 9.4) (0.070 g) and 4-dimethylaminopyridine ("DMAP") (0.169 g) in anhydrous chloroform (2 ml) and toluene (1 ml) under a nitrogen atmosphere was heated to reflux for four hours. Isobutyryl chloride (53 μl) was added and the reaction mixture heated to reflux for a further two hours. The reaction mixture was then allowed to cool to ambient temperature and diluted with dichloromethane and aqueous hydrochloric acid (2M). The solids were removed by filtration and the filtrate was separated. The aqueous layer was extracted with further dichloromethane. The combined organic extracts were concentrated. The residue was purified by column chromatography on silica gel (eluent: ethyl acetate/hexane 1:6) to give Compound No. C136 of Table C (0.019 g).

The following compounds were made using the same method: Compound Nos. C48, C137 and C138 of Table C.

10. Reactions which are Covered by Scheme 10

Example 10.1

Preparation of 3-(2-chloro-5-trifluoromethyl-phenyl)-1-(2,2-difluoro-ethyl)-2,2-dioxo-5-oxy-1,2-dihydro-2-λ-6-thia-1,5,8-triaza-naphthalen-4-ol (Compound No. E1 of Table E)

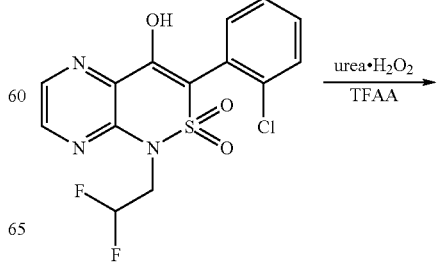

urea·H₂O₂ / TFAA →

-continued

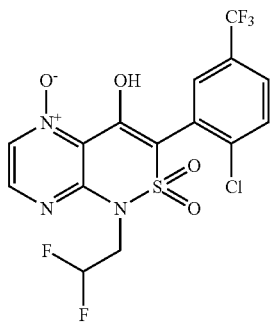

A mixture of Compound No. D16 of Table D (0.869 g) and freshly ground urea hydrogen peroxide (1.430 g) was stirred in dichloromethane (50 ml) and trifluoroacetic anhydride ("TFAA") (0.868 ml) was added dropwise at ambient temperature. The reaction mixture was stirred at ambient temperature for 72 hours. The reaction mixture was quenched by addition of aqueous sodium metabisulfite (1M) (50 ml). The phases were separated and the organic phase was dried over magnesium sulfate and concentrated to give Compound No. E1 of Table E (0.118 g).

11. Separation of Atropisomers

Example 11.1

Separation of the atropisomers of 3-(2-chloro-6-trifluoromethyl-phenyl)-1-(2,2-difluoro-ethyl)-2,2-dioxo-1,2-dihydro-2-λ-6-thia-1,5,8-triaza-naphthalen-4-ol A sample of 3-(2-chloro-6-trifluoromethyl-phenyl)-1-(2, 2-difluoro-ethyl)-2,2-dioxo-1,2-dihydro-2-λ-6-thia-1,5,8-triaza-naphthalen-4-ol was subjected to preparative chromatography (100 mg).

| Preparative method: | |
|---|---|
| Column: | 250 × 20 mm CHIRALPAK ® AS-H 5 µm |
| Eluent: | heptane/ethanol/trifluoroacetic acid (80:20:0.1) |
| Flow rate: | 20 ml/min |
| Detection: | UV 260 nm |
| Temperature: | 21° C. |
| Analytical method: | |
| Column: | 250 × 4.6 mm CHIRALPAK ® AS-H 5µm |
| Eluent: | heptane/ethanol/trifluoroacetic acid (80:20:0.1) |
| Flow rate: | 1 ml/min |
| Detection: | DAD 230 nm |
| Temperature: | 25° C. |

Compound No. D61 of Table D (atropisomer A, unknown stereochemistry) was obtained in >92% chemical purity and >99% enantiomeric excess (47 mg); this compound has a retention time of 8.16 minutes. Compound No. D62 of Table D (atropisomer B, unknown stereochemistry) was obtained in >97% chemical purity and >99% enantiomeric excess (40 mg); this compound has a retention time of 10.59 minutes.

TABLE A

Compounds of formula (A'), i.e. a compound of formula (I) wherein $R^1$, $R^2$ and $R^3$ is hydrogen, $R^5$ is hydroxy, and $R^4$ has the values as described in the table below.

(A')

| Compound No. | $R^4$ | 1H-NMR (400 MHz, CDCl$_3$ except where indicated; chemical shifts in ppm) |
|---|---|---|
| A1 | 2,4-di-Cl-phenyl- | d$_6$-DMSO: 8.17 (d, 1H), 7.81 (d, 1H), 7.66 (m, 1H), 7.45-7.57 (m, 2H). |
| A2 | 2-Cl-3,6-di-F-phenyl- | d$_6$-DMSO: 11.04 (bs, 1H), 8.18 (d, 1H), 8.09 (d, 1H), 7.54-7.58 (m, 1H), 7.33-7.38 (m, 1H). |
| A3 | 2-F$_3$CO-phenyl- | d$_6$-DMSO: 10.63 (bs, 1H), 8.14 (d, 1H), 8.06 (d, 1H), 7.56-7.61 (m, 2H), 7.43-7.47 (m, 2H). |
| A4 | 3,4-di-Cl-phenyl- | d$_6$-DMSO: 10.80 (bs, 1H), 8.10 (d, 1H), 8.03 (d, 1H), 7.84 (m, 1H), 7.73-7.76 (m, 1H), 7.62-7.65 (m, 1H). |
| A5 | 2-F$_3$C-phenyl- | d$_6$-DMSO: 10.55 (bs, 1H), 8.15 (d, 1H), 8.07 (d, 1H), 7.84 (d, 1H), 7.76 (t, 1H), 7.68 (t, 1H), 7.57 (d, 1H). |
| A6 | 2-Cl-5-F$_3$C-phenyl- | Compound used crude. |

Key:
bs = broad singlet; d = doublet; t = triplet; m = multiplet.

TABLE B

Compounds of formula (B'), i.e. a compound of formula (I) wherein $R^1$, $R^2$ and $R^3$ are hydrogen, and $R^4$ and $R^5$ have the values as described in the table below.

(B')

| Compound No. | $R^4$ | $R^5$ | 1H-NMR (400 MHz, CDCl$_3$ except where indicated; chemical shifts in ppm) |
|---|---|---|---|
| B1 | 2,4-di-Cl-phenyl- | t-Bu—(CO)O— | d$_4$-MeOH: 8.03 (d, 1H), 7.96 (d, 1H), 7.65 (m, 1H), 7.45-7.52 (m, 2H), 1.09 (s, 9H). |
| B2 | 2,4-di-Cl-phenyl- | i-Pr(CO)O— | d$_6$-DMSO: 8.15 (d, 1H), 8.07 (d, 1H), 7.85 (m, 1H), 7.42 (d, 1H), 2.65 (sept, 1H), 0.95 (d, 3H), 0.85 (d, 3H). |
| B3 | 2-Cl-3,6-di-F-phenyl- | t-Bu—(CO)O— | d$_6$-DMSO: 8.20 (d, 1H), 8.11 (d, 1H), 7.67-7.72 (m, 1H), 7.46-7.51 (m, 1H), 1.01 (s, 9H). |
| B4 | 3,4-di-Cl-phenyl- | t-Bu(CO)O— | d$_6$-DMSO: 8.14 (d, 1H), 8.07 (d, 1H), 7.83 (d, 1H), 7.67 (m, 1H), 7.48-7.51 (m, 1H), 1.13 (s, 9H). |
| B5 | 2-F$_3$C-phenyl- | i-Pr(CO)O— | 8.90 (bs, 1H), 7.79-7.81 (d, 2H), 7.56-7.70 (m, 4H), 2.59-2.68 (m, 1H), 1.24 (d, 3H), 1.00 (d, 3H). |
| B6 | 2-Cl-5-F$_3$C-phenyl- | i-Pr(CO)O— | 8.11 (d, 1H), 8.04 (d, 1H), 7.85-7.89 (m, 1H), 7.68 (m, 2H), 2.64-2.72 (m, 1H), 0.97-1.07 (m, 6H). |

Key:
s = singlet; bs = broad singlet; d = doublet; sept = septet; m = multiplet; Pr = propyl; Bu = butyl.

TABLE C

Compounds of formula (C'), i.e. a compound of formula (I) wherein $R^1$ and $R^2$ are hydrogen, and $R^3$, $R^4$ and $R^5$ have the values as described in the table below.

(C')

| Compound No. | $R^3$ | $R^4$ | $R^5$ | 1H-NMR (400 MHz, CDCl$_3$ except where indicated; chemical shifts in ppm) |
|---|---|---|---|---|
| C1 | Me | 2,4-di-Cl-phenyl- | c-Pr—(CO)O— | 8.43 (d, 1H), 8.46 (d, 1H), 7.60 (m, 1H), 7.50 (d, 1H), 7.37-7.40 (dd, 1H), 3.70 (s, 3H), 1.70-1.75 (m, 1H), 0.96-1.06 (m, 4H). |
| C2 | Me | 2,4-di-Cl-phenyl- | t-Bu—(CO)O— | 8.45 (d, 1H), 8.40 (d, 1H), 7.58 (d, 1H), 7.51 (d, 1H), 7.36-7.39 (m, 1H), 3.70 (s, 3H), 1.14 (s, 9H). |
| C3 | Me | 2,4-di-Cl-phenyl- | MeO— | 8.51 (d, 1H), 8.50 (d, 1H), 7.55-7.59 (m, 2H), 7.38-7.41 (m, 1H), 3.84 (s, 3H), 3.66 (s, 3H). |
| C4 | Me | 2-Cl-3,6-di-F-phenyl- | t-Bu—(CO)O— | 8.49 (d, 1H), 8.44 (d, 1H), 7.28-7.33 (m, 1H), 7.12-7.17 (m, 1H), 3.73 (s, 3H), 1.15 (s, 9H). |
| C5 | Et | 2,4-di-Cl-phenyl- | t-Bu—(CO)O— | 8.45 (d, 1H), 8.41 (d, 1H), 7.57 (m, 1H), 7.51 (m, 1H), 7.36-7.38 (dd, 1H), 4.39 (q, 2H), 1.49 (t, 3H), 1.14 (s, 9H). |
| C6 | Et | 2,4-di-Cl-phenyl- | i-Pr—(CO)O— | 8.46 (d, 1H), 8.41 (d, 1H), 7.57 (d, 1H), 7.50 (d, 1H), 7.36-7.38 (dd, 1H), 4.34-4.44 (m, 2H), 2.72 (sept, 1H), 1.50 (t, 3H), 1.12 (d, 3H), 1.07 (d, 3H). |
| C7 | Et | 2-Cl-3,6-di-F-phenyl- | t-Bu—(CO)O— | 8.49 (d, 1H), 8.44 (d, 1H), 7.27-7.32 (m, 1H), 7.11-7.16 (m, 1H), 4.41 (q, 2H), 1.49 (t, 3H), 1.15 (s, 9H). |
| C8 | Me | 3,4-di-Cl-phenyl- | t-Bu—(CO)O— | 8.45 (d, 1H), 8.41 (d, 1H), 7.65 (d, 1H), 7.57 (d, 1H), 7.43-7.46 (m, 1H), 3.70 (s, 3H), 1.25 (s, 9H). |
| C9 | Me | 2-Cl-3,6-di-F-phenyl- | i-Pr—(CO)O— | 8.50 (d, 1H), 8.44 (d, 1H), 7.29-7.34 (m, 1H), 7.12-7.17 (m, 1H), 3.73 (s, 3H), 2.74 (sept, 1H), 1.12 (d, 3H), 1.10 (d, 3H). |
| C10 | Et | 3,4-di-Cl-phenyl- | t-Bu—(CO)O— | 8.44 (d, 1H), 8.40 (d, 1H), 7.65 (d, 1H), 7.56 (d, 1H), 7.43-7.46 (m, 1H), 4.37 (q, 2H), 1.51 (t, 3H), 1.25 (s, 9H). |
| C11 | MeO—H$_2$C— | 2,4-di-Cl-phenyl- | t-Bu—(CO)O— | 8.53 (d, 1H), 8.50 (d, 1H), 7.57 (d, 1H), 7.50 (d, 1H), 7.37-7.40 (m, 1H), 5.67-5.82 (m, 2H), 3.52 (s, 3H), 1.15 (s, 9H). |
| C12 | F$_2$HC—H$_2$C— | 2,4-di-Cl-phenyl- | t-Bu—(CO)O— | 8.50 (d, 1H), 8.48 (d, 1H), 7.58 (d, 1H), 7.50 (d, 1H), 7.38-7.40 (m, 1H), 6.10-6.37 (tt, 1H), 4.54-4.79 (m, 2H), 1.15 (s, 9H). |
| C13 | Et | 2-F$_3$CO-phenyl- | i-Pr—(CO)O— | 8.45 (d, 1H), 8.40 (d, 1H), 7.53-7.63 (m, 2H), 7.38-7.43 (m, 2H), 4.30-4.46 (m, 2H), 2.71 (sept, 1H), 1.48 (t, 3H), 1.12 (d, 3H), 1.08 (d, 3H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

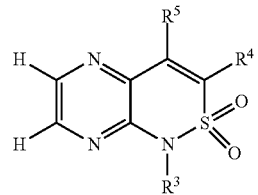

(C')

| Compound No. | $R^3$ | $R^4$ | $R^5$ | 1H-NMR (400 MHz, CDCl$_3$ except where indicated; chemical shifts in ppm) |
|---|---|---|---|---|
| C14 | Et | 3-F$_3$C-phenyl- | t-Bu—(CO)O— | 8.45 (d, 1H), 8.41 (d, 1H), 7.75-7.82 (m, 3H), 7.61-7.65 (m, 1H), 4.38 (q, 2H), 1.52 (t, 3H), 1.19 (s, 9H). |
| C15 | Et | 4-Cl-2-F$_3$C-phenyl- | t-Bu—(CO)O— | 8.46 (d, 1H), 8.42 (d, 1H), 7.81-7.82 (m, 1H), 7.60-7.66 (m, 2H), 4.29-4.48 (m, 2H), 1.46 (t, 3H), 1.08 (s, 9H). |
| C16 | Et | 2,3-di-Cl-6-F-phenyl- | t-Bu—(CO)O— | 8.49 (d, 1H), 8.44 (d, 1H), 7.57-7.61 (m, 1H), 7.11-7.16 (m, 1H), 4.41 (q, 2H), 1.49 (t, 3H), 1.14 (s, 9H). |
| C17 | Et | 2-Cl-6-F$_3$C-phenyl- | t-Bu—(CO)O— | 8.48 (d, 1H), 8.43 (d, 1H), 7.74-7.78 (m, 2H), 7.55-7.60 (m, 1H), 4.38 (q, 2H), 1.50 (t, 3H), 1.07 (s, 9H). |
| C18 | F$_2$HC—H$_2$C— | 2-F$_3$CS-phenyl- | i-Pr—(CO)O— | 8.51 (d, 1H), 8.49 (m, 1H), 7.90-7.92 (m, 1H), 7.59-7.67 (m, 3H), 6.12-6.42 (tt, 1H), 4.74-4.85 (m, 1H), 4.49-4.60 (m, 1H), 2.68 (sept, 1H), 1.08 (d, 3H), 1.01 (d, 3H). |
| C19 | Et | 2-F$_3$CS-phenyl- | i-Pr—(CO)O— | 8.46 (d, 1H), 8.42 (d, 1H), 7.89-7.91 (m, 1H), 7.57-7.67 (m, 3H), 4.32-4.48 (m, 2H), 2.67 (sept, 1H), 1.50 (t, 3H), 1.07 (d, 3H), 1.00 (d, 3H). |
| C20 | F$_2$HC—H$_2$C— | 2,3-di-Cl-6-F-phenyl- | t-Bu—(CO)O— | 8.53 (d, 1H), 8.51 (d, 1H), 7.59-7.63 (m, 1H), 7.13-7.17 (m, 1H), 6.09-6.39 (tt, 1H), 4.62-4.72 (m, 2H), 1.14 (s, 9H). |
| C21 | F$_2$HC—H$_2$C— | 2-F$_3$CO-phenyl- | t-Bu—(CO)O— | 8.49 (d, 1H), 8.47 (d, 1H), 7.55-7.61 (m, 2H), 7.39-7.43 (m, 2H), 6.06-6.37 (tt, 1H), 4.69-4.80 (m, 1H), 4.49-4.61 (m, 1H), 1.15 s, 9H). |
| C22 | F$_2$HC—H$_2$C— | 2-F$_3$CO-phenyl- | i-Pr—(CO)O— | 8.50 (d, 1H), 8.47 (d, 1H), 7.55-7.61 (m, 2H), 7.40-7.45 (m, 2H), 6.07-6.37 (tt, 1H), 4.68-4.79 (m, 1H), 4.50-4.61 (m, 1H), 2.72 (sept, 1H), 1.13 (d, 3H), 1.09 (d, 3H). |
| C23 | MeO—H$_2$C— | 2-F$_3$CS-phenyl- | t-Bu—(CO)O— | 8.52 (d, 1H), 8.51 (d, 1H), 7.89-7.91 (m, 1H), 7.58-7.67 (m, 3H), 5.67-5.84 (m, 2H), 3.55 (s, 3H), 1.10 (s, 9H). |
| C24 | Et | 2-Cl-6-F-3-MeO-phenyl- | t-Bu—(CO)O— | 8.47 (d, 1H), 8.42 (d, 1H), 7.02-7.14 (m, 2H), 4.37 (q, 2H), 3.92 (t, 3H), 1.49 (t, 3H), 1.12 (s, 9H). |
| C25 | F$_2$HC—H$_2$C— | 2-Cl-6-F-3-MeO-phenyl- | t-Bu—(CO)O— | 8.51 (d, 1H), 8.49 (d, 1H), 7.04-7.15 (m, 2H), 6.09-6.40 (tt, 1H), 4.61-4.72 (m, 2H), 3.93 (t, 3H), 1.13 (s, 9H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

(C')

| Compound No. | $R^3$ | $R^4$ | $R^5$ | 1H-NMR (400 MHz, CDCl$_3$ except where indicated; chemical shifts in ppm) |
|---|---|---|---|---|
| C26 | Et | 3,4-di-Cl-phenyl- | i-Pr—(CO)O— | 8.45 (d, 1H), 8.41 (d, 1H), 7.66 (d, 1H), 7.57 (d, 1H), 7.42-7.45 (m, 1H), 4.37 (q, 2H), 2.80 (sept, 1H), 1.51 (t, 3H), 1.20-1.21 (m, 6H). |
| C27 | MeO—H$_2$C— | 2,4-di-Cl-phenyl- | i-Pr—(CO)O— | 8.53 (d, 1H), 8.51 (d, 1H), 7.58 (d, 1H), 7.50 (d, 1H), 7.37-7.40 (m, 1H), 5.67-5.82 (m, 2H), 3.52 (s, 3H), 2.73 (sept, 1H), 1.13 (d, 3H), 1.09 (d, 3H). |
| C28 | F$_2$HC—H$_2$C— | 2,6-di-Cl-phenyl- | t-Bu—(CO)O— | 8.52 (d, 1H), 8.49 (d, 1H), 7.47-7.49 (m, 2H), 7.36-7.40 (m, 1H), 6.12-6.43 (tt, 1H), 4.64-4.71 (m, 2H), 1.11 (s, 9H). |
| C29 | Et | 4-Cl-2-F$_3$C-phenyl- | F$_3$C—(SO$_2$)O— | 8.61 (s, 2H), 7.85-7.86 (m, 1H), 7.68-7.74 (m, 2H), 4.32-4.49 (m, 2H), 1.48 (t, 3H). |
| C30 | Et | 2-Cl-6-F$_3$C-phenyl- | i-Pr—(CO)O— | 8.48 (d, 1H), 8.43 (d, 1H), 7.74-7.78 (m, 2H), 7.56-7.60 (m, 1H), 4.38 (q, 2H), 2.67 (sept, 1H), 1.50 (t, 3H), 1.04 (d, 3H), 1.02 (d, 3H). |
| C31 | F$_2$HC—H$_2$C— | 2-Cl-6-F$_3$C-phenyl- | t-Bu—(CO)O— | 8.51 (m, 1H), 8.49 (m, 1H), 7.76-7.79 (m, 2H), 7.58-7.61 (m, 1H), 6.17-6.41 (tt, 1H), 4.60-4.65 (m, 2H), 1.07 (s, 9H). |
| C32 | F$_2$HC—H$_2$C— | 2,3-di-Cl-6-F-phenyl- | EtS—(CO)O— | 8.59 (d, 1H), 8.54 (d, 1H), 7.61-7.65 (m, 1H), 7.14-7.18 (m, 1H), 6.08-6.38 (tt, 1H), 4.57-4.76 (m, 2H), 2.86 (q, 2H), 1.27 (t, 3H). |
| C33 | Et | 2-Cl-5-F$_3$C-phenyl- | t-Bu—(CO)O— | 8.47 (d, 1H), 8.42 (d, 1H), 7.81 (m, 1H), 7.66-7.71 (m, 2H), 4.35-4.46 (m, 2H), 1.51 (t, 3H), 1.10 (s, 9H). |
| C34 | F$_2$HC—H$_2$C— | 2-Cl-5-F$_3$C-phenyl- | t-Bu—(CO)O— | 8.52 (d, 1H), 8.50 (d, 1H), 7.80 (m, 1H), 7.68-7.74 (m, 2H), 6.11-6.41 (tt, 1H), 4.54-4.80 (m, 2H), 1.11 (s, 9H). |
| C35 | F$_2$HC—H$_2$C— | 3-Br-2-Cl-6-F-phenyl- | t-Bu—(CO)O— | 8.52 (d, 1H), 8.51 (d, 1H), 7.76-7.79 (m, 1H), 7.06-7.11 (m, 1H), 6.09-6.39 (tt, 1H), 4.62-4.72 (m, 2H), 1.14 (s, 9H). |
| C36 | F$_2$HC—H$_2$C— | 2,3-di-Cl-6-F-phenyl- | i-Pr—(CO)O— | 8.51-8.53 (m, 2H), 7.60-7.63 (m, 1H), 7.13-7.17 (m, 1H), 6.09-6.39 (tt, 1H), 4.58-4.76 (m, 2H), 2.74 (sept, 1H), 1.12 (d, 3H), 1.10 (d, 3H). |
| C37 | F$_2$HC—H$_2$C— | 2,3,6-tri-Cl-phenyl- | EtS—(CO)O— | 8.58 (d, 1H), 8.53 (d, 1H), 7.57 (d, 1H), 7.44 (d, 1H), 6.10-6.41 (tt, 1H), 4.63-4.71 (m, 2H), 2.85 (q, 2H), 1.27 (t, 3H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

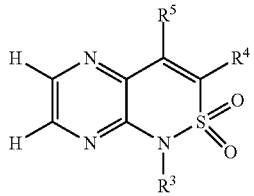

(C')

| Compound No. | $R^3$ | $R^4$ | $R^5$ | 1H-NMR (400 MHz, CDCl$_3$ except where indicated; chemical shifts in ppm) |
|---|---|---|---|---|
| C38 | F$_2$HC—H$_2$C— | 2,3,6-tri-Cl-phenyl- | i-Pr—(CO)O— | 8.51-8.53 (m, 2H), 7.56 (d, 1H), 7.43 (d, 1H), 6.12-6.42 (tt, 1H), 4.63-4.71 (m, 2H), 2.73 (sept, 1H), 1.10 (d, 3H), 1.08 (d, 3H). |
| C39 | F$_2$HC—H$_2$C— | 2-Br-phenyl- | i-Pr—(CO)O— | 8.50 (d, 1H), 8.48 (d, 1H), 7.74 (d, 1H), 7.53-7.55 (m, 1H), 7.35-7.46 (m, 2H), 6.11-6.42 (tt, 1H), 4.73-4.84 (m, 1H), 4.52-4.63 (m, 1H), 2.69 (sept, 2H), 1.07 (d, 3H), 1.01 (d, 3H). |
| C40 | Me | 2-Cl-quinolin-3-yl- | MeO— | 8.54 (d, 1H), 8.53 (d, 1H), 8.45 (s, 1H), 8.10 (d, 1H), 7.91 (d, 1H), 7.84 (dt, 1H), 7.65 (dt, 1H), 3.95 (s, 3H), 3.70 (s, 3H). |
| C41 | Me | 2-Cl-quinolin-3-yl- | t-Bu—(CO)O— | 8.49 (d, 1H), 8.44 (m, 2H), 8.09 (d, 1H), 7.83-7.94 (m, 2H), 7.63-7.67 (m, 1H), 3.75 (s, 3H), 1.08 (s, 9H). |
| C42 | F$_2$HC—H$_2$C— | 2-Cl-6-F-3-(3'-Cl-Ph)-phenyl- | t-Bu—(CO)O— | 8.53 (d, 1H), 8.51 (d, 1H), 7.45-7.49 (m, 1H), 7.37-7.40 (m, 3H), 7.22-7.29 (m, 2H), 6.10-6.40 (tt, 1H), 4.64-4.73 (m, 2H), 1.16 (s, 9H). |
| C43 | Et | 2-F-6-F$_3$C-phenyl- | t-Bu—(CO)O— | 8.47 (d, 1H), 8.43 (d, 1H), 7.63-7.65 (m, 2H), 7.42-7.46 (m, 1H), 4.36-4.42 (m, 2H), 1.48 (t, 3H), 1.08 (s, 9H). |
| C44 | F$_2$HC—H$_2$C— | 2,5-bis-F$_3$C-phenyl- | t-Bu—(CO)O— | 8.53 (d, 1H), 8.51 (d, 1H), 7.90-7.99 (m, 3H), 6.10-6.40 (tt, 1H), 4.53-4.84 (m, 2H), 1.10 (s, 9H). |
| C45 | Et | 2,4-di-Cl-5-F-phenyl- | t-Bu—(CO)O— | 8.47 (d, 1H), 8.42 (d, 1H), 7.62 (d, 1H), 7.40 (d, 1H), 4.34-4.44 (m, 2H), 1.50 (t, 3H), 1.17 (s, 9H). |
| C46 | Et | 2,5-bis-F$_3$C-phenyl- | t-Bu—(CO)O— | 8.49 (d, 1H), 8.44 (d, 1H), 7.91-7.99 (m, 3H), 4.30-4.49 (m, 2H), 1.48 (t, 3H), 1.04 (s, 9H). |
| C47 | F$_2$HC—H$_2$C— | 2,4-di-Cl-5-F-phenyl- | t-Bu—(CO)O— | 8.51 (d, 1H), 8.49 (d, 1H), 7.63 (d, 1H), 7.39 (d, 1H), 6.08-6.39 (tt, 1H), 4.53-4.78 (m, 2H), 1.18 (s, 9H). |
| C48 | F$_2$HC—H$_2$C— | 2,6-di-Et-4-Me-phenyl- | i-Pr—(CO)O— | 8.47 (d, 1H), 8.44 (d, 1H), 7.04 (s, 2H), 6.09-6.39 (tt, 1H), 4.62-4.70 (dt, 2H), 2.60-2.72 (m, 5H), 2.37 (s, 3H), 1.20 (t, 6H), 0.98 (d, 6H). |
| C49 | F$_2$HC—H$_2$C— | 2,6-di-Br-phenyl- | i-Pr—(CO)O— | 8.52 (d, 1H), 8.50 (d, 1H), 7.70 (d, 2H), 7.22 (t, 1H), 6.17-6.47 (tt, 1H), 4.63-4.71 (dt, 2H), 2.73 (sept, 2H), 1.07 (d, 6H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

(C')

| Compound No. | $R^3$ | $R^4$ | $R^5$ | 1H-NMR (400 MHz, CDCl$_3$ except where indicated; chemical shifts in ppm) |
|---|---|---|---|---|
| C50 | Et | 2,5-di-Cl-6-F$_3$C-phenyl- | i-Pr—(CO)O— | 8.49 (d, 1H), 8.44 (d, 1H), 7.75 (d, 1H), 7.69 (d, 1H), 4.38 (q, 2H), 2.69 (sept, 2H), 1.50 (t, 3H), 1.06 (d, 3H), 1.05 (d, 3H). |
| C51 | Et | 2-Cl-5-I-phenyl- | i-Pr—(CO)O— | 8.47 (d, 1H), 8.42 (d, 1H), 7.85 (d, 1H), 7.73-7.76 (dd, 1H), 7.27 (d, 1H), 4.32-4.46 (m, 2H), 2.72 (sept, 2H), 1.50 (t, 3H), 1.11 (d, 3H), 1.07 (d, 3H). |
| C52 | F$_2$HC—H$_2$C— | 2,5-di-Cl-6-F$_3$C-phenyl- | t-Bu—(CO)O— | 8.52 (d, 1H), 8.51 (d, 1H), 7.77 (d, 1H), 7.70 (d, 1H), 6.13-6.44 (tt, 1H), 4.58-4.66 (m, 2H), 1.09 (s, 9H). |
| C53 | F$_2$HC—H$_2$C— | 2,5-di-Cl-6-F$_3$C-phenyl- | i-Pr—(CO)O— | 8.52 (d, 1H), 8.51 (d, 1H), 7.77 (d, 1H), 7.70 (d, 1H), 6.14-6.44 (tt, 1H), 4.57-4.66 (m, 2H), 2.69 (sept, 2H), 1.07 (d, 3H), 1.06 (d, 3H). |
| C54 | F$_2$HC—H$_2$C— | 2-Cl-5-I-phenyl- | i-Pr—(CO)O— | 8.51 (d, 1H), 8.48 (d, 1H), 7.84 (d, 1H), 7.75-7.77 (dd, 1H), 7.28 (d, 1H), 6.10-6.40 (tt, 1H), 4.68-4.79 (m, 1H), 4.53-4.64 (m, 1H), 2.71 (sept, 2H), 1.12 (d, 3H), 1.08 (d, 3H). |
| C55 | F$_2$HC—H$_2$C— | 2-Cl-5-I-phenyl- | t-Bu—(CO)O— | 8.51 (d, 1H), 8.48 (d, 1H), 7.84 (d, 1H), 7.75-7.77 (dd, 1H), 7.28 (d, 1H), 6.10-6.40 (tt, 1H), 4.68-4.79 (m, 1H), 4.53-4.64 (m, 1H), 1.14 (s, 9H). |
| C56 | F$_2$HC—H$_2$C— | 2-Cl-5-(3'-Cl—Ph)-phenyl- | t-Bu—(CO)O— | 8.51 (d, 1H), 8.48 (d, 1H), 7.73 (m, 1H), 7.63 (m, 1H), 7.55 (m, 1H), 7.34-7.46 (m, 4H), 6.12-6.42 (m, 1H), 4.71-4.82 (m, 1H), 4.54-4.66 (m, 1H), 1.12 (s, 9H). |
| C57 | F$_3$C—H$_2$C— | 2,4-di-Cl-phenyl- | i-Pr—(CO)O— | 8.53 (d, 1H), 8.51 (d, 1H), 7.59 (m, 1H), 7.46 (d, 1H), 7.38 (dd, 1H), 4.88-5.06 (m, 2H), 2.73 (sept, 1H), 1.14 (d, 3H), 1.08 (d, 3H). |
| C58 | FH$_2$C—H$_2$C— | 2,4-di-Cl-phenyl- | i-Pr—(CO)O— | 8.46 (s, 2H), 7.58 (d, 1H), 7.50 (d, 1H), 7.38 (dd, 1H), 4.52-4.86 (m, 4H), 2.73 (sept, 1H), 1.12 (d, 3H), 1.08 (d, 3H). |
| C59 | F$_2$HC—H$_2$C— | 2-Br-5-F$_3$C-phenyl- | i-Pr—(CO)O— | 8.53 (d, 1H), 8.51 (d, 1H), 7.89 (d, 1H), 7.78 (m, 1H), 7.63-7.65 (dd, 1H), 6.12-6.42 (tt, 1H), 4.73-4.84 (m, 1H), 4.52-4.64 (m, 1H), 2.71 (sept, 1H), 1.08 (d, 3H), 1.03 (d, 3H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

(C')

| Compound No. | $R^3$ | $R^4$ | $R^5$ | 1H-NMR (400 MHz, CDCl$_3$ except where indicated; chemical shifts in ppm) |
|---|---|---|---|---|
| C60 | F$_2$HC—H$_2$C— | 2-Br-5-F$_3$C-phenyl- | EtS—(CO)O— | 8.59 (d, 1H), 8.53 (d, 1H), 7.90 (d, 1H), 7.79 (m, 1H), 7.64-7.66 (dd, 1H), 6.11-6.41 (tt, 1H), 4.74-4.85 (m, 1H), 4.51-4.63 (m, 1H), 2.77-2.92 (m, 2H), 1.25 (t, 3H). |
| C61 | F$_2$HC—H$_2$C— | 2-F$_3$C-phenyl- | i-Pr—(CO)O— | 8.50 (d, 1H), 8.47 (d, 1H), 7.82-7.85 (m, 1H), 7.63-7.70 (m, 3H), 6.07-6.37 (m, 1H), 4.78-4.88 (m, 1H), 4.44-4.55 (m, 1H), 2.65 (sept, 1H), 1.02 (d, 3H), 0.95 (d, 3H). |
| C62 | F$_2$HC—H$_2$C— | 2-F$_3$C-phenyl- | t-Bu—(CO)O— | 8.50 (d, 1H), 8.48 (d, 1H), 7.82-7.85 (m, 1H), 7.64-7.69 (m, 3H), 6.06-6.37 (m, 1H), 4.79-4.90 (m, 1H), 4.44-4.56 (m, 1H), 1.04 (s, 9H). |
| C63 | Et | 2-F$_3$C-phenyl- | i-Pr—(CO)O— | 8.46 (d, 1H1), 8.42 (d, 1H), 7.81-7.83 (m, 1H), 7.63-7.67 (m, 3H), 4.30-4.48 (m, 2H), 2.64 (sept, 1H), 1.47 (t, 3H), 1.02 (d, 3H), 0.94 (d, 3H). |
| C64 | Et | 2-F$_3$C-phenyl- | t-Bu—(CO)O— | 8.46 (d, 1H), 8.42 (d, 1H), 7.81-7.83 (m, 1H), 7.63-7.67 (m, 3H), 4.32-4.47 (m, 2H), 1.47 (t, 3H), 1.04 (s, 9H). |
| C65 | F$_2$HC—H$_2$C— | 2-nitro-phenyl- | i-Pr—(CO)O— | 8.50 (d, 1H), 8.49 (d, 1H), 8.26 (d, 1H), 7.71-7.81 (m, 3H), 6.15-6.46 (m, 1H), 4.76-4.87 (m, 1H), 4.43-4.55 (m, 1H), 2.68 (sept, 1H), 1.09 (d, 3H), 1.05 (d, 3H). |
| C66 | F$_2$HC—H$_2$C— | 2-nitro-phenyl- | t-Bu—(CO)O— | 8.51 (d, 1H), 8.48 (d, 1H), 8.25 (d, 1H), 7.70-7.81 (m, 3H), 6.15-6.46 (m, 1H), 4.77-4.87 (m, 1H), 4.44-4.56 (m, 1H), 1.10 (s, 9H). |
| C67 | Et | 2-nitro-phenyl- | i-Pr—(CO)O— | 8.50 (d, 1H), 8.45 (d, 1H), 8.25 (d, 1H), 7.71-7.80 (m, 3H), 4.35-4.52 (m, 2H), 2.72 (sept, 1H), 1.55 (t, 3H), 1.12 (d, 3H), 1.08 (d, 3H). |
| C68 | HC≡C—H$_2$C— | 2-nitro-phenyl- | i-Pr—(CO)O— | 8.53 (d, 1H), 8.47 (d, 1H), 8.23 (d, 1H), 7.69-7.80 (m, 3H), 5.02 (d, 2H), 2.67 (sept, 1H), 2.36 (t, 1H), 1.08 (d, 3H), 1.03 (d, 3H). |
| C69 | Et | 2-Br-5-F$_3$C-phenyl- | t-Bu—(CO)O— | 8.48 (d, 1H), 8.43 (d, 1H), 7.86-7.88 (m, 1H), 7.79 (bs, 1H), 7.59-7.62 (m, 1H), 4.36-4.47 (m, 2H), 1.51 (t, 3H), 1.09 (s, 9H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

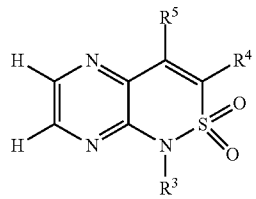

(C')

| Compound No. | $R^3$ | $R^4$ | $R^5$ | 1H-NMR (400 MHz, CDCl$_3$ except where indicated; chemical shifts in ppm) |
|---|---|---|---|---|
| C70 | Et | 2-Br-5-F$_3$C-phenyl- | i-Pr—(CO)O— | 8.48 (d, 1H), 8.44 (d, 1H), 7.88 (d, 1H), 7.79 (bs, 1H), 7.60-7.62 (m, 1H), 4.34-4.49 (m, 2H), 2.70 (sept, 1H), 1.52 (t, 3H), 1.07 (d, 3H), 1.01 (d, 3H). |
| C71 | Et | 2,3,6-tri-Cl-phenyl- | EtS—(CO)O— | 8.51 (d, 1H), 8.50 (d, 1H), 7.55 (d, 1H), 7.43 (d, 1H), 4.41 (q, 2H), 2.85 (q, 2H), 1.50 (t, 3H), 1.27 (t, 3H). |
| C72 | Et | 2,3,6-tri-Cl-phenyl- | t-Bu—(CO)O— | 8.49 (d, 1H), 8.44 (d, 1H), 7.53 (d, 1H), 7.42 (d, 1H), 4.41 (q, 2H), 1.50 (t, 3H), 1.13 (s, 9H). |
| C73 | F$_2$HC—H$_2$C— | 2-Cl-3-F$_3$C-phenyl- | i-Pr—(CO)O— | 8.52 (d, 1H), 8.50 (d, 1H), 7.87 (d, 1H), 7.76 (d, 1H), 7.52 (t, 1H), 6.10-6.41 (tt, 1H), 4.54-4.81 (m, 2H), 2.71 (sept, 1H), 1.06 (d, 3H), 1.02 (d, 3H). |
| C74 | F$_2$HC—H$_2$C— | 2-Cl-3-F$_3$C-phenyl- | t-Bu—(CO)O— | 8.52 (d, 1H), 8.50 (d, 1H), 7.87 (d, 1H), 7.77 (d, 1H), 7.52 (t, 1H), 6.11-6.41 (tt, 1H), 4.55-4.81 (m, 2H), 1.10 (s, 9H). |
| C75 | Et | 2-Cl-3-F$_3$C-phenyl- | i-Pr—(CO)O— | 8.48 (d, 1H), 8.43 (d, 1H), 7.86 (d, 1H), 7.77 (bs, 1H), 7.51 (t, 1H), 4.34-4.48 (m, 2H), 2.70 (sept, 1H), 1.51 (t, 3H), 1.06 (d, 3H), 1.01 (d, 3H). |
| C76 | Et | 2-Cl-3-F$_3$C-phenyl- | t-Bu—(CO)O— | 8.47 (d, 1H), 8.43 (d, 1H), 7.85 (d, 1H), 7.78 (bs, 1H), 7.50 (t, 1H), 4.36-4.46 (m, 2H), 1.51 (t, 3H), 1.09 (s, 9H). |
| C77 | F$_2$HC—H$_2$C— | 2-F-6-F$_3$C-phenyl- | i-Pr—(CO)O— | 8.56 (d, 1H), 8.54 (d, 1H), 7.70-7.72 (m, 2H), 7.48-7.53 (m, 1H), 6.13-6.44 (tt, 1H), 4.57-4.81 (m, 2H), 2.73 (sept, 1H), 1.09 (d, 3H), 1.07 (d, 3H). |
| C78 | F$_2$HC—H$_2$C— | 2-F-6-F$_3$C-phenyl- | t-Bu—(CO)O— | 8.56 (d, 1H), 8.54 (d, 1H), 7.69-7.72 (m, 2H), 7.48-53 (t, 1H), 6.13-6.43 (tt, 1H), 4.58-4.81 (m, 2H), 1.13 (s, 9H). |
| C79 | F$_2$HC—H$_2$C— | 2,6-bis-F$_3$C-phenyl- | i-Pr—(CO)O— | 8.49 (d, 1H), 8.48 (d, 1H), 8.07 (d, 2H), 7.82 (t, 1H), 6.16-6.46 (tt, 1H), 4.50-4.58 (dt, 2H), 2.64 (sept, 1H), 1.07 (d, 6H). |
| C80 | F$_2$HC—H$_2$C— | 2-Br-5-F$_3$C-phenyl- | t-Bu—(CO)O— | 8.52 (d, 1H), 8.50 (d, 1H), 7.89 (d, 1H), 7.78 (s, 1H), 7.61-7.64 (dd, 1H), 6.12-6.42 (tt, 1H), 4.73-4.84 (m, 1H), 4.53-4.64 (m, 1H), 1.10 (s, 9H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

(C')

| Compound No. | $R^3$ | $R^4$ | $R^5$ | 1H-NMR (400 MHz, CDCl$_3$ except where indicated; chemical shifts in ppm) |
|---|---|---|---|---|
| C81 | F$_2$HC—H$_2$C— | 2-I-phenyl- | t-Bu—(CO)O— | 8.54 (d, 1H), 8.51 (d, 1H), 8.03 (d, 1H), 7.49-7.57 (m, 2H), 7.21-7.25 (dt, 1H), 6.18-6.49 (tt, 1H), 4.83-4.94 (m, 1H), 4.54-4.66 (m, 1H), 1.13 (s, 9H). |
| C82 | F$_2$HC—H$_2$C— | 2-I-phenyl- | EtS—(CO)O— | 8.56 (d, 1H), 8.50 (d, 1H), 8.00 (d, 1H), 7.47-7.55 (m, 2H), 7.20-7.24 (dt, 1H), 6.15-6.45 (tt, 1H), 4.80-4.91 (m, 1H), 4.48-4.59 (m, 1H), 2.81-2.87 (m, 2H), 1.25 (t, 3H). |
| C83 | F$_2$HC—H$_2$C— | 2-Br-5-F$_3$C-phenyl- | Me—(SO$_2$)O— | 8.62 (d, 1H), 8.59 (d, 1H), 7.88-7.92 (m, 2H), 7.66-7.69 (dd, 1H), 6.11-6.41 (tt, 1H), 4.77-4.87 (m, 1H), 4.51-4.63 (m, 1H), 3.38 (s, 3H). |
| C84 | HC≡C—H$_2$C— | 2,5-di-Cl-6-F$_3$C-phenyl- | i-Pr—(CO)O— | 8.57 (d, 1H), 8.51 (d, 1H), 7.76 (d, 1H), 7.70 (d, 1H), 5.02-5.03 (m, 2H), 2.69 (sept, 1H), 2.33 (t, 1H), 1.04-1.07 (dd, 6H). |
| C85 | HC≡C—H$_2$C— | 2,5-di-Cl-6-F$_3$C-phenyl- | EtS—(CO)O— | 8.59 (d, 1H), 8.57 (d, 1H), 7.77 (d, 1H), 7.70 (d, 1H), 5.01-5.03 (m, 2H), 2.83 (q, 1H), 2.34 (t, 1H), 1.30 (t, 3H). |
| C86 | HC≡C—H$_2$C— | 2,5-di-Cl-6-F$_3$C-phenyl- | t-Bu—(CO)O— | 8.56 (d, 1H), 8.51 (d, 1H), 7.76 (d, 1H), 7.70 (d, 1H), 5.02-5.04 (m, 2H), 2.33 (t, 1H), 1.09 (s, 9H). |
| C87 | Et | 2-Cl-5-F$_3$C-phenyl- | EtS—(CO)O— | 8.51 (d, 1H), 8.50 (d, 1H), 7.82 (s, 1H), 7.68-7.74 (m, 2H), 4.33-4.38 (m, 2H), 2.77-2.91 (m, 2H), 1.26 (t, 3H). |
| C88 | F$_2$HC—H$_2$C— | 2,4-di-Cl-5-F-phenyl- | EtS—(CO)O— | 8.58 (d, 1H), 8.52 (d, 1H), 7.65 (d, 1H), 7.39 (d, 1H), 6.08-6.38 (tt, 1H), 4.51-4.79 (m, 2H), 2.86 (q, 2H), 1.29 (t, 3H). |
| C89 | Me | 2-Cl-5-F$_3$C-phenyl- | EtS—(CO)O— | 8.51 (d, 1H), 8.49 (d, 1H), 7.83 (bs, 1H), 7.69-7.74 (m, 2H), 3.73 (s, 3H), 2.77-2.91 (m, 2H), 1.25 (t, 3H). |
| C90 | Me | 2-Cl-5-F$_3$C-phenyl- | i-Pr—(CO)O— | 8.48 (d, 1H), 8.43 (d, 1H), 7.81 (bs, 1H), 7.68-7.73 (m, 2H), 3.73 (s, 3H), 2.71 (sept, 1H), 1.09 (d, 3H), 1.03 (d, 3H). |
| C91 | F$_2$HC—H$_2$C— | 2-Cl-5-F$_3$C-phenyl- | i-Pr—(CO)O— | 8.52 (d, 1H), 8.51 (d, 1H), 7.79 (bs, 1H), 7.69-7.74 (m, 2H), 6.11-6.41 (tt, 1H), 4.69-4.80 (m, 1H), 4.54-4.65 (m, 1H), 2.71 (sept, 1H), 1.09 (d, 3H), 1.04 (d, 3H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

(C')

| Compound No. | $R^3$ | $R^4$ | $R^5$ | 1H-NMR (400 MHz, CDCl$_3$ except where indicated; chemical shifts in ppm) |
|---|---|---|---|---|
| C92 | Me | 2,3,6-tri-Cl-phenyl- | i-Pr—(CO)O— | 8.49 (d, 1H), 8.44 (d, 1H), 7.53-7.56 (d, 1H), 7.41-7.44 (d, 1H), 3.73 (s, 3H), 2.73 (sept, 1H), 1.10 (d, 3H), 1.08 (d, 3H). |
| C93 | Me | 2,3,6-tri-Cl-phenyl- | t-Bu—(CO)O— | 8.49 (d, 1H), 8.44 (d, 1H), 7.53-7.55 (d, 1H), 7.41-7.43 (d, 1H), 3.73 (s, 3H), 1.13 (s, 9H). |
| C94 | Me | 2,3,6-tri-Cl-phenyl- | EtS—(CO)O— | 8.51 (d, 1H), 8.50 (d, 1H), 7.55-7.57 (d, 1H), 7.42-7.45 (d, 1H), 3.73 (s, 3H), 2.83-2.88 (q, 2H), 1.27 (t, 3H). |
| C95 | F$_2$HC—H$_2$C— | 2-Cl-5-F$_3$C-phenyl- | Me—(SO$_2$)O— | 8.62 (d, 1H), 8.59 (d, 1H), 7.89 (bs, 1H), 7.71-7.78 (m, 2H), 6.09-6.40 (tt, 1H), 4.73-4.84 (m, 1H), 4.53-4.65 (m, 1H), 3.38 (s, 3H). |
| C96 | Me—C≡C—H$_2$C— | 2,5-di-Cl-6-F$_3$C-phenyl- | t-Bu—(CO)O— | 8.56 (d, 1H), 8.49 (d, 1H), 7.75 (d, 1H), 7.69 (d, 2H), 4.97-5.00 (m, 2H), 1.80 (t, 1H), 1.09 (s, 9H). |
| C97 | Me—C≡C—H$_2$C— | 2,5-di-Cl-6-F$_3$C-phenyl- | EtS—(CO)O— | 8.58 (d, 1H), 8.54 (d, 1H), 7.76 (d, 1H), 7.70 (d, 2H), 4.96-4.98 (m, 2H), 2.83 (q, 2H), 1.80 (t, 1H), 1.31 (t, 3H). |
| C98 | Et | 2,3-di-Cl-phenyl- | t-Bu—(CO)O— | 8.46 (d, 1H), 8.42 (d, 1H), 7.60 (d, 1H), 7.49 (d, 1H), 7.32 (t, 1H), 4.35-4.46 (m, 2H), 1.50 (t, 3H), 1.11 (s, 9H). |
| C99 | Et | 2,3-di-Cl-phenyl- | EtS—(CO)O— | 8.52 (d, 1H), 8.51 (d, 1H), 7.66 (dd, 1H), 7.53 (dd, 1H), 7.38 (t, 1H), 4.36-4.51 (m, 2H), 2.89 (q, 2H), 1.54 (t, 3H), 1.34 (t, 3H). |
| C100 | F$_2$HC—H$_2$C— | 2,3-di-Cl-phenyl- | t-Bu—(CO)O— | 8.55 (d, 1H), 8.52 (d, 1H), 7.66 (dd, 1H), 7.52 (dd, 1H), 7.38 (t, 1H), 6.14-6.45 (tt, 1H), 4.74-4.85 (m, 1H), 4.58-4.69 (m, 1H), 1.16 (s, 9H). |
| C101 | F$_2$HC—H$_2$C— | 2,3-di-Cl-phenyl- | EtS—(CO)O— | 8.61 (d, 1H), 8.55 (d, 1H), 7.68 (dd, 1H), 7.52 (dd, 1H), 7.39 (t, 1H), 6.13-6.43 (tt, 1H), 4.74-4.85 (m, 1H), 4.55-4.66 (m, 1H), 2.89 (q, 2H), 1.34 (t, 3H). |
| C102 | F$_2$HC—H$_2$C— | 2,3-di-Cl-phenyl- | i-Pr—(CO)O— | 8.51 (d, 1H), 8.49 (d, 1H), 7.63 (dd, 1H), 7.47 (dd, 1H), 7.34 (t, 1H), 6.10-6.40 (tt, 1H), 4.70-4.81 (m, 1H), 4.53-4.64 (m, 1H), 2.71 (sept, 2H), 1.10 (d, 3H), 1.05 (d, 3H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

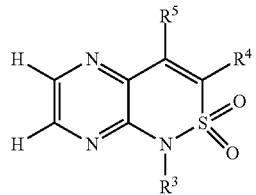

(C')

| Compound No. | $R^3$ | $R^4$ | $R^5$ | 1H-NMR (400 MHz, $CDCl_3$ except where indicated; chemical shifts in ppm) |
|---|---|---|---|---|
| C103 | $F_2HC\text{—}H_2C\text{—}$ | 2,5-di-Cl-6-$F_3$C-phenyl- | EtS—(CO)O— | 8.58 (d, 1H), 8.53 (d, 1H), 7.78 (d, 1H), 7.71 (d, 2H), 6.13-6.43 (tt, 1H), 4.56-4.66 (m, 2H), 2.83 (q, 2H), 1.25 (t, 3H). |
| C104 | $F_3C\text{—}H_2C\text{—}$ | 2,4-di-Cl-phenyl- | t-Bu—(CO)O— | 8.54 (d, 1H), 8.50 (d, 1H), 7.58 (d, 1H), 7.46 (d, 1H), 7.38 (dd, 1H), 4.89-5.07 (m, 2H), 1.15 (s, 9H). |
| C105 | $F_2HC\text{—}H_2C\text{—}$ | 2-Cl-6-$F_3$C-phenyl- | EtS—(CO)O— | 8.57 (d, 1H), 8.52 (d, 1H), 7.77-7.81 (m, 2H), 7.60-7.64 (m, 1H), 6.13-6.43 (tt, 1H), 4.53-4.71 (m, 2H), 2.82 (q, 2H), 1.26 (t, 3H). |
| C106 | $F_3C\text{—}H_2C\text{—}$ | 2,4-di-Cl-phenyl- | $F_3C\text{—}H_2C\text{—}O\text{—}$ | 8.62 (d, 1H), 8.57 (d, 1H), 7.60 (d, 1H), 7.45 (d, 1H), 7.40 (dd, 1H), 4.90-5.06 (m, 2H), 4.71-4.80 (m, 1H), 4.44-4.53 (m, 1H). |
| C107 | $F_2HC\text{—}H_2C\text{—}$ | 3-Br-2-Cl-6-F-phenyl- | EtS—(CO)O— | 8.58 (d, 1H), 8.53 (d, 1H), 7.77-7.81 (m, 1H), 7.08-7.12 (m, 1H), 6.07-6.38 (tt, 1H), 4.57-4.75 (m, 2H), 2.85 (q, 2H), 1.27 (t, 3H). |
| C108 | Et | 5-Cl-2-$F_3$C-phenyl- | t-Bu—(CO)O— | 8.47 (d, 1H), 8.43 (d, 1H), 7.76 (d, 1H), 7.66 (s, 1H), 7.62 (d, 1H), 4.30-4.48 (m, 2H), 1.47 (t, 3H), 1.08 (s, 9H). |
| C109 | Et | 5-Cl-2-$F_3$C-phenyl- | EtS—(CO)O— | 8.50 (d, 1H), 8.49 (d, 1H), 7.77 (d, 1H), 7.68 (s, 1H), 7.64 (d, 1H), 4.25-4.53 (m, 2H), 2.79-2.90 (m, 2H), 1.47 (t, 3H), 1.30 (t, 3H). |
| C110 | Et | 5-Cl-2-$F_3$C-phenyl- | i-Pr—(CO)O— | 8.48 (d, 1H), 8.43 (d, 1H), 7.76 (d, 1H), 7.66 (s, 1H), 7.62 (d, 1H), 4.30-4.48 (m, 2H), 2.68 (sept, 1H), 1.47 (t, 3H), 1.07 (d, 3H), 1.01 (d, 3H). |
| C111 | $F_2HC\text{—}H_2C\text{—}$ | 5-Cl-2-$F_3$C-phenyl- | t-Bu—(CO)O— | 8.52 (d, 1H), 8.49 (d, 1H), 7.77 (d, 1H), 7.65 (s, 1H), 7.64 (d, 1H), 6.06-6.36 (m, 1H), 4.78-4.88 (m, 1H), 4.43-4.55 (m, 1H), 1.08 (s, 9H). |
| C112 | $F_2HC\text{—}H_2C\text{—}$ | 5-Cl-2-$F_3$C-phenyl- | EtS—(CO)O— | 8.56 (d, 1H), 8.51 (d, 1H), 7.78 (d, 1H), 7.67 (s, 1H), 7.65 (d, 1H), 6.06-6.36 (m, 1H), 4.76-4.87 (m, 1H), 4.42-4.53 (m, 1H), 2.84-2.95 (m, 2H), 1.25 (t, 3H). |
| C113 | $F_2HC\text{—}H_2C\text{—}$ | 5-Cl-2-$F_3$C-phenyl- | i-Pr—(CO)O— | 8.52 (d, 1H), 8.50 (d, 1H), 7.77 (d, 1H), 7.65 (s, 1H), 7.64 (d, 1H), 6.06-6.37 (m, 1H), 4.77-4.87 (m, 1H), 4.43-4.55 (m, 1H), 2.69 (sept, 1H), 1.07 (d, 3H), 1.02 (d, 3H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

(C')

| Compound No. | $R^3$ | $R^4$ | $R^5$ | 1H-NMR (400 MHz, CDCl$_3$ except where indicated; chemical shifts in ppm) |
|---|---|---|---|---|
| C114 | (E,Z)-ClHC=HC— | 2-Cl-5-F$_3$C-phenyl- | i-Pr—(CO)O— | 8.51-8.53 (m, 2H), 7.79 (s, 1H), 7.69-7.75 (m, 2H), 6.91-7.01 (m, 2H), 2.71 (sept, 1H), 1.09 (d, 3H), 1.04 (d, 3H). |
| C115 | Cl$_2$HC—H$_2$C— | 2-Cl-5-F$_3$C-phenyl- | i-Pr—(CO)O— | 8.52-8.54 (m, 2H), 7.78 (s, 1H), 7.69-7.74 (m, 2H), 6.20-6.24 (m, 1H), 5.02-5.07 (m, 1H), 4.79-4.85 (m, 1H), 2.71 (sept, 1H), 1.09 (d, 3H), 1.04 (d, 3H). |
| C116 | Cl$_2$HC—H$_2$C— | 2,4-di-Cl-phenyl- | i-Pr—(CO)O— | 8.50-8.52 (m, 2H), 7.59 (s, 1H), 7.47 (d, 1H), 7.38 (d, 1H), 6.18-6.21 (m, 1H), 5.00-5.04 (m, 1H), 4.80-4.84 (m, 1H), 2.72 (sept, 1H), 1.13 (d, 3H), 1.09 (d, 3H). |
| C117 | F$_2$HC—H$_2$C— | 2-I-phenyl- | i-Pr—(CO)O— | 8.51 (d, 1H), 8.48 (d, 1H), 7.99 (d, 1H), 7.46-7.53 (m, 2H), 7.18-7.22 (m, 1H), 6.14-6.45 (tt, 1H), 4.79-4.90 (m, 1H), 4.50-4.61 (m, 1H), 2.69 (sept, 1H), 1.06 (d, 3H), 1.00 (d, 3H). |
| C118 | H$_2$C=HC—H$_2$C— | 5-Cl-2-F$_3$C-phenyl- | t-Bu—(CO)O— | 8.46 (d, 1H), 8.44 (d, 1H), 7.76 (d, 1H), 7.65 (s, 1H), 7.62 (d, 1H), 5.99-6.08 (m, 1H), 5.26-5.41 (m, 2H), 4.90-4.93 (m, 2H), 1.08 (s, 9H). |
| C119 | H$_2$C=HC—H$_2$C— | 5-Cl-2-F$_3$C-phenyl- | EtS—(CO)O— | 8.49-8.51 (m, 2H), 7.77 (d, 1H), 7.67 (s, 1H), 7.64 (d, 1H), 5.99-6.08 (m, 1H), 5.26-5.41 (m, 2H), 4.89-4.92 (m, 2H), 2.79-2.90 (m, 2H), 1.26 (t, 3H). |
| C120 | F$_2$HC—H$_2$C— | 5-Cl-2-F$_3$C-phenyl- | EtO—(CO)O— | 8.56 (d, 1H), 8.53 (d, 1H), 7.79 (d, 1H), 7.68 (s, 1H), 7.66 (d, 1H), 6.06-6.36 (m, 1H), 4.78-4.88 (m, 1H), 4.42-4.54 (m, 1H), 4.23 (q, 2H), 1.27 (t, 3H). |
| C121 | ClH$_2$C—H$_2$C— | 2-F$_3$C-phenyl- | i-Pr—(CO)O— | 7.81 (d, 1H), 7.77-7.80 (m, 1H), 7.58-7.65 (m, 3H), 7.54 (d, 1H), 4.52-4.65 (m, 2H), 4.09 (t, 2H), 2.59 (sept, 1H), 0.99 (d, 3H), 0.88 (d, 3H). |
| C122 | F$_2$HC—F$_2$C—H$_2$C— | 2,4-di-Cl-phenyl- | i-Pr—(CO)O— | 8.57 (d, 1H), 8.45 (d, 1H), 7.58 (d, 1H), 7.46 (d, 1H), 7.38 (dd, 1H), 5.79-6.09 (m, 1H), 4.48-5.07 (m, 2H), 2.74 (sept, 1H), 1.08-1.14 (m, 6H). |
| C123 | ClH$_2$C—H$_2$C— | 2-Cl-5-F$_3$C-phenyl- | i-Pr—(CO)O— | 8.45-8.48 (m, 2H), 7.79 (s, 1H), 7.68-7.73 (m, 2H), 4.55-4.72 (m, 2H), 3.88-3.92 (m, 2H), 2.70 (sept, 1H), 1.13 (d, 3H), 1.08 (d, 3H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

(C')

| Compound No. | $R^3$ | $R^4$ | $R^5$ | 1H-NMR (400 MHz, CDCl$_3$ except where indicated; chemical shifts in ppm) |
|---|---|---|---|---|
| C124 | F$_2$HC—H$_2$C— | 3-Cl-5-F$_3$C-phenyl- | EtO—(CO)O— | 8.57 (d, 1H), 8.53 (d, 1H), 7.78-7.79 (m, 2H), 7.73 (s, 1H), 6.12-6.42 (m, 1H), 4.60-4.68 (dt, 2H), 4.29 (q, 2H), 1.33 (t, 3H). |
| C125 | F$_2$HC—H$_2$C— | 2-Cl-6-F$_3$C-phenyl- | PhS—(CO)O— | 8.60 (d, 1H), 8.51 (d, 1H), 7.78-7.81 (m, 2H), 7.64 (t, 1H), 7.32-7.42 (m, 5H), 6.10-6.40 (tt, 1H), 4.51-4.68 (m, 2H). |
| C126 | F$_2$HC—H$_2$C— | 2,3,6-tri-Cl-phenyl- | PhS—(CO)O— | 8.61 (d, 1H), 8.53 (d, 1H), 7.60 (d, 1H), 7.35-7.47 (m, 6H), 6.07-6.38 (tt, 1H), 4.61-4.68 (dt, 2H). |
| C127 | F$_2$HC—H$_2$C— | 2,4-bis-F$_3$C-phenyl- | i-Pr—(CO)O— | 8.53 (d, 1H), 8.52 (d, 1H), 8.09 (s, 1H), 7.96 (d, 1H), 7.83 (d, 1H), 6.06-6.36 (tt, 1H), 4.77-4.88 (m, 1H), 4.45-4.56 (m, 1H), 2.67 (sept, 1H), 1.06 (d, 3H), 0.99 (d, 3H). |
| C128 | F$_2$HC—H$_2$C— | 2-cyano-phenyl- | i-Pr—(CO)O— | 8.53 (d, 1H), 8.51 (d, 1H), 7.85 (d, 1H), 7.72-7.75 (m, 2H), 7.63-7.67 (m, 1H), 6.16-6.46 (tt, 1H), 4.67-4.82 (m, 1H), 4.52-4.64 (m, 1H), 2.72 (sept, 1H), 1.11 (d, 3H), 1.05 (d, 3H). |
| C129 | F$_2$HC—H$_2$C— | 2-Cl-6-F$_3$C-phenyl- | MeS—(CO)O— | 8.57 (d, 1H), 8.52 (d, 1H), 7.78 (t, 2H), 7.62 (t, 1H), 6.13-6.43 (tt, 1H), 4.58-4.66 (m, 2H), 2.31 (s, 3H). |
| C130 | F$_2$HC—H$_2$C— | 2,3,6-tri-Cl-phenyl- | MeS—(CO)O— | 8.58 (d, 1H), 8.53 (d, 1H), 7.57 (d, 1H), 7.44 (d, 1H), 6.11-6.41 (tt, 1H), 4.63-4.71 (dt, 2H), 2.34 (s, 3H). |
| C131 | F$_2$HC—H$_2$C— | 2,4-bis-F$_3$C-phenyl- | MeS—(CO)O— | 8.59 (d, 1H), 8.54 (d, 1H), 8.10 (s, 1H), 7.97 (d, 1H), 7.84 (d, 1H), 6.06-6.37 (m, 1H), 4.77-4.88 (m, 1H), 4.44-4.55 (m, 1H), 2.33 (s, 3H). |
| C132 | F$_2$HC—H$_2$C— | 4-Br-2-F$_3$C-phenyl- | i-Pr—(CO)O— | 8.51 (d, 1H), 8.49 (d, 1H), 7.98 (d, 1H), 7.82 (dd, 1H), 7.53 (d, 1H), 6.05-6.35 (tt, 1H), 4.76-4.87 (m, 1H), 4.43-4.55 (m, 1H), 2.68 (sept, 1H), 1.08 (d, 3H), 1.02 (d, 3H). |
| C133 | F$_2$HC—H$_2$C— | 4-Br-2-F$_3$C-phenyl- | MeS—(CO)O— | 8.57 (d, 1H), 8.52 (d, 1H), 7.98 (d, 1H), 7.84 (dd, 1H), 7.54 (d, 1H), 6.05-6.35 (m, 1H), 4.76-4.87 (m, 1H), 4.42-4.54 (m, 1H), 2.33 (s, 3H). |
| C134 | F$_2$HC—H$_2$C— | 2,3-di-Cl-6-F$_3$C-phenyl- | i-Pr—(CO)O— | 8.52 (d, 1H), 8.51 (d, 1H), 7.77 (d, 1H), 7.70 (s, 1H), 6.13-6.44 (tt, 1H), 4.58-4.66 (m, 2H), 2.69 (sept, 1H), 2.41 (s, 3H), 1.07 (d, 3H), 1.06 (d, 3H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

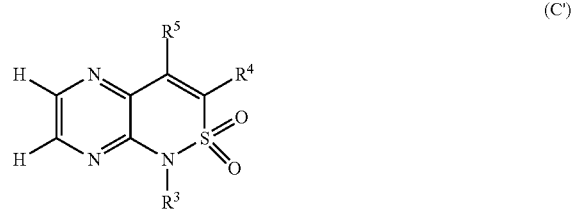

(C')

| Compound No. | $R^3$ | $R^4$ | $R^5$ | 1H-NMR (400 MHz, CDCl$_3$ except where indicated; chemical shifts in ppm) |
|---|---|---|---|---|
| C135 | F$_2$HC—H$_2$C— | 2,3-di-Cl-6-F$_3$C-phenyl- | EtS—(CO)O— | 8.58 (d, 1H), 8.53 (d, 1H), 7.78 (d, 1H), 7.71 (s, 1H), 6.15-6.40 (m, 1H), 4.54-4.69 (m, 2H), 2.84 (q, 2H), 1.26 (t, 3H). |
| C136 | F$_2$HC—H$_2$C— | 2-Cl-4-Me-phenyl- | i-Pr—(CO)O— | 8.49 (d, 1H), 8.46 (d, 1H), 7.42 (d, 1H), 7.37 (s, 1H), 7.19 (d, 1H), 6.10-6.40 (m, 1H), 4.68-4.79 (m, 1H), 4.52-4.64 (m, 1H), 2.71 (sept, 1H), 2.41 (s, 3H), 1.10 (d, 3H), 1.05 (d, 3H). |
| C137 | F$_2$HC—H$_2$C— | 2-F-6-MeO-phenyl- | i-Pr—(CO)O— | 8.48 (d, 1H), 8.45 (d, 1H), 7.41-7.47 (m, 1H), 6.80-6.84 (m, 2H), 6.08-6.39 (m, 1H), 4.51-4.69 (m, 2H), 3.87 (s, 3H), 2.72 (sept, 1H), 1.12 (d, 6H). |
| C138 | F$_2$HC—H$_2$C— | 2-F-5-MeO-phenyl- | i-Pr(—CO)O— | 8.49 (d, 1H), 8.46 (d, 1H), 7.11-7.16 (m, 1H), 7.00-7.04 (m, 2H), 6.12-6.43 (m, 1H), 4.53-4.74 (m, 2H), 3.82 (s, 3H), 2.77 (sept, 1H), 1.17 (d, 6H). |
| C139 | F$_2$HC—H$_2$C— | 3-EtO(CO)-6-F$_3$C-pyrid-2-yl- | MeS—(CO)O— | 2:1 Mixture of ethyl ester and methyl ester. Ethyl ester: 8.58-8.59 (m, 1H), 8.55 (d, 1H), 8.51-8.52 (m, 1H), 7.89-7.92 (m, 1H), 6.15-6.47 (m, 1H), 4.44-4.87 (m, 2H), 4.28-4.37 (m, 2H), 2.34 (s, 3H), 1.27 (t, 3H). Methyl ester: 8.58-8.59 (m, 1H), 8.55 (d, 1H), 8.51-8.52 (m, 1H), 7.89-7.92 (m, 1H), 6.15-6.47 (m, 1H), 4.44-4.87 (m, 2H), 2.34 (s, 3H), 3.86 (s, 3H). |
| C140 | H$_2$C=(Me)C—H$_2$C— | 2,3-di-Cl-phenyl- | t-Bu—(CO)O— | 8.44 (d, 1H), 8.43 (d, 1H), 7.60 (d, 1H), 7.47 (d, 1H), 7.31 (t, 1H), 4.88-4.96 (m, 4H), 1.81 (s, 3H), 1.12 (s, 9H). |
| C141 | F$_2$HC—H$_2$C— | 2-Cl-4-I-phenyl- | t-Bu—(CO)O— | 8.48 (d, 1H), 8.45 (d, 1H), 7.93 (s, 1H), 7.73 (d, 1H), 7.26 (d, 1H), 6.09-6.39 (m, 1H), 4.52-4.77 (m, 2H), 1.14 (s, 9H). |
| C142 | F$_2$HC—H$_2$C— | 2-Cl-4-(4'-Cl-2'-F-Ph)-phenyl- | t-Bu—(CO)O— | 8.51 (m, 1H), 8.47 (m, 1H), 7.71 (s, 1H), 7.62 (d, 1H), 7.53 (d, 1H), 7.34-7.43 (m, 1H), 7.22-7.26 (m, 2H), 6.11-6.42 (m, 1H), 4.55-4.81 (m, 2H), 1.13 (s, 9H). |

TABLE C-continued

Compounds of formula (C'), i.e. a compound of formula (I) wherein $R^1$ and $R^2$ are hydrogen, and $R^3$, $R^4$ and $R^5$ have the values as described in the table below.

(C')

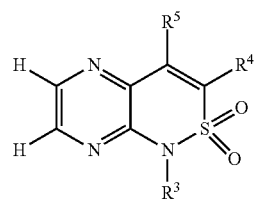

| Compound No. | $R^3$ | $R^4$ | $R^5$ | 1H-NMR (400 MHz, CDCl$_3$ except where indicated; chemical shifts in ppm) |
|---|---|---|---|---|
| C143 | F$_2$HC—H$_2$C— | 2-Cl-6-F-5-MeO-phenyl- | i-Pr—(CO)O— | 8.51 (d, 1H), 8.49 (d, 1H), 7.28 (d, 1H), 7.06 (t, 1H), 6.10-6.40 (m, 1H), 4.59-4.75 (m, 2H), 3.92 (s, 3H), 2.73 (sept, 1H), 1.10 (dd, 6H). |
| C144 | F$_2$HC—H$_2$C— | 2-Cl-6-F-5-MeO-phenyl- | t-Bu—(CO)O— | 8.50 (d, 1H), 8.48 (d, 1H), 7.27 (d, 1H), 7.05 (t, 1H), 6.10-6.40 (m, 1H), 4.62-4.71 (m, 2H), 3.91 (s, 3H), 1.14 (s, 9H). |
| C145 | F$_2$HC—H$_2$C— | 2-Cl-6-F-5-MeO-phenyl- | EtS—(CO)O— | 8.56 (d, 1H), 8.51 (d, 1H), 7.29 (d, 1H), 7.07 (t, 1H), 6.09-6.39 (m, 1H), 4.57-4.75 (m, 2H), 3.92 (s, 3H), 2.85 (q, 2H), 1.26 (t, 3H). |
| C146 | F$_2$HC—H$_2$C— | 5-Me-2-F$_3$C-phenyl- | i-Pr—(CO)O— | 8.50 (d, 1H), 8.48 (d, 1H), 7.71 (d, 1H), 7.44-7.45 (m, 2H), 6.06-6.37 (m, 1H), 4.79-4.89 (m, 1H), 4.43-4.54 (m, 1H), 2.66 (sept, 1H), 1.04 (d, 3H), 0.97 (d, 3H). |
| C147 | F$_2$HC—H$_2$C— | 5-Me-2-F$_3$C-phenyl- | EtO—(CO)O— | 8.53 (d, 1H), 8.51 (d, 1H), 7.72 (d, 1H), 7.47 (s, 1H), 7.46 (d, 1H), 6.06-6.37 (m, 1H), 4.78-4.89 (m, 1H), 4.41-4.53 (m, 1H), 4.18-4.23 (q, 2H), 2.48 (s, 3H), 1.25 (t, 3H). |
| C148 | F$_2$HC—H$_2$C— | 5-Me-2-F$_3$C-phenyl- | t-Bu—(CO)O— | 8.50 (d, 1H), 8.47 (d, 1H), 7.70 (d, 1H), 7.45 (s, 1H), 7.44 (d, 1H), 6.06-6.36 (m, 1H), 4.79-4.90 (m, 1H), 4.42-4.54 (m, 1H), 2.47 (s, 3H), 1.05 (s, 9H). |
| C149 | F$_2$HC—H$_2$C— | 3-Cl-5-F$_3$C-phenyl- | i-Pr—(CO)O— | 8.52 (d, 1H), 8.50 (d, 1H), 7.76-7.77 (m, 2H), 7.71 (s, 1H), 6.12-6.42 (m, 1H), 4.60-4.68 (dt, 2H), 2.80 (sept, 1H), 1.19-1.20 (d, 6H). |

Key:
s = singlet; bs = broad singlet; d = doublet; t = triplet; q = quartet; dd = double doublet; dt = double triplet; tt = triple triplet; sept = septet; m = multiplet; Me = methyl; Et = ethyl; Pr = propyl; Bu = butyl.

TABLE D

Compound of formula (D'), i.e. a compound of formula (I) wherein $R^1$ and $R^2$ are hydrogen, $R^5$ is hydroxy, and $R^3$ and $R^4$ have the values as described in the table below.

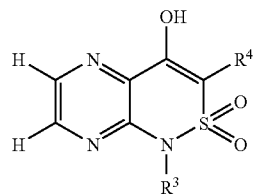
(D')

| Compound No. | $R^3$ | $R^4$ | 1H-NMR (400 MHz, CDCl$_3$ except where indicated; chemical shifts in ppm) |
|---|---|---|---|
| D1 | Me | 2,4-di-Cl-phenyl- | 8.55 (d, 1H), 8.35 (d, 1H), 8.23 (bs, 1H), 7.58-7.60 (m, 2H), 7.37-7.40 (m, 1H), 3.68 (s, 3H). |
| D2 | Me | 2-Cl-3,6-di-F-phenyl- | 8.59 (d, 1H), 8.38 (d, 1H), 8.24 (bs, 1H), 7.27-7.33 (m, 1H), 7.12-7.18 (m, 1H), 3.70 (s, 3H). |
| D3 | Et | 3-F$_3$C-phenyl- | 8.55 (d, 1H), 8.36 (d, 1H), 8.32 (bs, 1H), 7.92-8.00 (m, 2H), 7.60-7.72 (m, 2H), 4.38 (q, 2H), 1.50 (t, 3H). |
| D4 | Et | 2,3-di-Cl-6-F-phenyl- | d$_4$-MeOH: 8.62 (d, 1H), 8.52 (d, 1H), 7.68-7.72 (m, 1H), 7.25-7.29 (m, 1H), 4.29-4.35 (m, 2H), 1.43 (t, 3H). |
| D5 | Et | 2-F$_3$CO-phenyl- | 8.56 (d, 1H), 8.36 (d, 1H), 8.18 (bs, 1H), 7.70-7.72 (m, 1H), 7.52-7.56 (m, 1H), 7.39-7.43 (m, 2H), 4.32-4.41 (m, 2H), 1.48 (t, 3H). |
| D6 | Et | 2-Cl-6-F$_3$C-phenyl- | 8.58 (m, 1H), 8.37 (m, 1H), 7.74-7.79 (m, 2H), 7.54-7.58 (m, 1H), 4.33-4.38 (m, 2H), 1.46 (t, 3H). |
| D7 | Et | 2-F$_3$CS-phenyl- | 8.56 (d, 1H), 8.36 (d, 1H), 7.89-7.91 (m, 1H), 7.76-7.78 (m, 1H), 7.54-7.64 (m, 2H), 4.31-4.47 (m, 2H), 1.49 (t, 3H). |
| D8 | Et | 3,4-di-Cl-phenyl- | 8.55 (d, 1H), 8.36 (d, 1H), 7.84 (m, 1H), 7.54-7.60 (m, 2H), 4.36 (q, 2H), 1.49 (t, 3H). |
| D9 | F$_2$HC—H$_2$C— | 2,3-di-Cl-6-F-phenyl- | 8.62 (d, 1H), 8.49 (d, 1H), 7.59-7.63 (m, 1H), 7.13-7.17 (m, 1H), 6.05-6.36 (tt, 1H), 4.60-4.79 (m, 2H). |
| D10 | Et | 4-Cl-2-F$_3$C-phenyl- | 8.57 (d, 1H), 8.37 (d, 1H), 8.10 (bs, 1H), 7.83 (m, 1H), 7.64-7.69 (m, 2H), 4.28-4.47 (m, 2H), 1.46 (t, 3H). |
| D11 | F$_2$HC—H$_2$C— | 2-Cl-6-F$_3$C-phenyl- | 8.61 (m, 1H), 8.48 (m, 1H), 7.76-7.80 (m, 2H), 7.56-7.60 (m, 1H), 6.08-6.32 (tt, 1H), 4.56-4.77 (m, 2H). |
| D12 | F$_2$HC—H$_2$C— | 2-Cl-6-F-3-Me-phenyl- | 8.60 (d, 1H), 8.47 (d, 1H), 7.36-7.39 (m, 1H), 7.0-7.10 (m, 1H), 6.06-6.36 (tt, 1H), 4.60-4.79 (m, 2H), 2.43 (s, 3H). |
| D13 | Et | 3-Br-2-Cl-6-F-phenyl- | 8.50 (bs, 1H), 8.05 (m, 1H), 7.76-7.80 (m, 1H), 7.15-7.19 (m, 1H), 4.22-4.31 (m, 2H), 1.38-1.41 (t, 3H). |
| D14 | F$_2$HC—H$_2$C— | 3-Br-2-Cl-6-F-phenyl- | 8.54 (m, 2H), 7.79-7.83 (m, 1H), 7.15-7.20 (m, 1H), 6.08-6.38 (m, 1H), 4.51-4.67 (m, 2H). |
| D15 | Et | 2-Cl-5-F$_3$C-phenyl- | 8.58 (d, 1H), 8.36 (d, 1H), 7.91 (m, 1H), 7.66-7.71 (m, 2H), 4.36-4.42 (m, 2H), 1.50 (t, 3H). |
| D16 | F$_2$HC—H$_2$C— | 2-Cl-5-F$_3$C-phenyl- | 8.61 (d, 1H), 8.48 (d, 1H), 7.89 (m, 1H), 7.69-7.73 (m, 2H), 6.08-6.39 (tt, 1H), 4.57-4.82 (m, 2H). |
| D17 | F$_2$HC—H$_2$C— | 2,3,6-tri-Cl-phenyl- | 8.62 (d, 1H), 8.49 (d, 1H), 8.13 (bs, 1H), 7.55 (d, 1H), 7.44 (d, 1H), 6.06-6.36 (tt, 1H), 4.67-4.75 (m, 2H). |
| D18 | F$_2$HC—H$_2$C— | 2-Br-phenyl- | 8.58 (d, 1H), 8.45 (d, 1H), 8.15 (bs, 1H), 7.76 (d, 1H), 7.62-7.64 (m, 1H), 7.35-7.48 (m, 2H), 6.09-6.40 (tt, 1H), 4.54-4.65 (m, 1H), 4.75-4.86 (m, 1H). |
| D19 | F$_2$HC—H$_2$C— | 3-Cl-5-F$_3$C-phenyl- | 8.60 (d, 1H), 8.48 (d, 1H), 8.41 (bs, 1H), 7.89 (d, 2H), 7.70 (s, 1H), 6.07-6.38 (tt, 1H), 4.63-4.71 (dt, 2H). |

TABLE D-continued

Compound of formula (D'), i.e. a compound of formula (I) wherein $R^1$ and $R^2$ are hydrogen, $R^5$ is hydroxy, and $R^3$ and $R^4$ have the values as described in the table below.

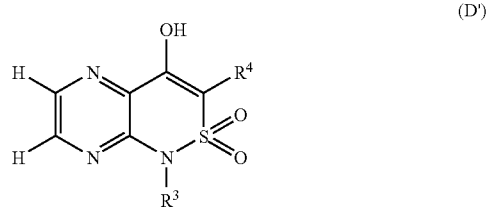

(D')

| Compound No. | $R^3$ | $R^4$ | 1H-NMR (400 MHz, $CDCl_3$ except where indicated; chemical shifts in ppm) |
| --- | --- | --- | --- |
| D20 | $F_2HC—H_2C—$ | 2-Cl-6-F-3-(3'-Cl—Ph)-phenyl- | 8.61 (d, 1H), 8.48 (d, 1H), 8.20 (bs, 1H), 7.45-7.49 (m, 1H), 7.33-7.39 (m, 3H), 7.23-7.27 (m, 2H), 6.06-6.37 (tt, 1H), 4.61-4.80 (m, 2H). |
| D21 | Et | 2-F-6-$F_3$C-phenyl- | 8.59 (d, 1H), 8.38 (d, 1H), 8.11 (bs, 1H), 7.62-7.66 (m, 2H), 7.43-7.48 (m, 1H), 4.32-4.43 (m, 2H), 1.46 (t, 3H). |
| D22 | $F_2HC—H_2C—$ | 2,5-bis-$F_3$C-phenyl- | 8.60 (d, 1H), 8.46 (d, 1H), 7.96-7.99 (m, 2H), 7.89-7.91 (m, 1H), 6.03-6.33 (m, 1H), 4.79-4.90 (m, 1H), 4.43-4.55 (m, 1H). |
| D23 | Et | 2,4-di-Cl-5-F-phenyl- | 8.50 (d, 1H), 8.28 (d, 1H), 7.55 (d, 1H), 7.40 (d, 1H), 4.27-4.34 (m, 2H), 1.42 (t, 3H). |
| D24 | Et | 2,5-bis-$F_3$C-phenyl- | 8.59 (d, 1H), 8.37 (d, 1H), 7.96-7.98 (m, 2H), 7.88-7.90 (m, 1H), 4.29-4.47 (m, 2H), 1.46 (t, 3H). |
| D25 | $F_2HC—H_2C—$ | 2,4-di-Cl-5-F-phenyl- | 8.52 (d, 1H), 8.39 (d, 1H), 7.56 (d, 1H), 7.38 (d, 1H), 6.00-6.30 (tt, 1H), 4.47-4.72 (m, 2H). |
| D26 | Et | 2,5-di-Cl-6-$F_3$C-phenyl- | 8.53-8.64 (m, 2H), 8.09 (bs, 1H), 7.80-7.89 (m, 2H), 4.29-4.33 (m, 2H), 1.38-1.48 (m, 3H). |
| D27 | $F_2HC—H_2C—$ | 2,5-di-Cl-6-$F_3$C-phenyl- | 8.51-8.56 (m, 2H), 8.14 (bs, 1H), 7.76-7.82 (m, 2H), 6.08-6.38 (m, 1H), 4.53-4.59 (m, 2H). |
| D28 | $F_2HC—H_2C—$ | 2,6-di-Br-phenyl- | 8.41-8.46 (m, 2H), 7.66-7.70 (m, 2H), 7.15-7.17 (m, 1H), 6.08-6.37 (m, 1H), 4.51-4.56 (m, 2H). |
| D29 | $F_2HC—H_2C—$ | 2-Cl-5-I-phenyl- | 8.59 (d, 1H), 8.46 (d, 1H), 8.21 (bs, 1H), 7.93 (d, 1H), 7.74-7.77 (dd, 1H), 7.29 (d, 1H), 6.08-6.38 (tt, 1H), 4.71-4.82 (m, 1H), 4.55-4.66 (m, 1H). |
| D30 | $F_2HC—H_2C—$ | 2-Br-5-$F_3$C-phenyl- | 8.61 (d, 1H), 8.48 (d, 1H), 8.23 (bs, 1H), 7.86-7.91 (m, 2H), 7.61-7.63 (dd, 1H), 6.09-6.39 (tt, 1H), 4.75-4.86 (m, 1H), 4.55-4.67 (m, 1H). |
| D31 | $F_2HC—H_2C—$ | 2-$F_3$C-phenyl- | 8.56 (d, 1H), 8.43 (d, 1H), 7.83 (d, 1H), 7.61-7.73 (m, 3H), 6.03-6.33 (m, 1H), 4.80-4.91 (m, 1H), 4.42-4.54 (m, 1H). |
| D32 | $F_2HC—H_2C—$ | 2-nitro-phenyl- | 8.57 (d, 1H), 8.44 (d, 1H), 8.15 (d, 1H), 7.74-7.81 (m, 2H), 7.64-7.69 (m, 1H), 6.09-6.39 (m, 1H), 4.75-4.86 (m, 1H), 4.45-4.56 (m, 1H). |
| D33 | Et | 2-$F_3$C-phenyl- | 8.54 (d, 1H), 8.33 (d, 1H), 7.82 (d, 1H), 7.59-7.74 (m, 3H), 4.28-4.46 (m, 2H), 1.45 (t, 3H). |
| D34 | Et | 2-nitro-phenyl- | 8.56 (d, 1H), 8.36 (d, 1H), 8.15 (d, 1H), 7.64-7.84 (m, 3H), 4.30-4.45 (m, 2H), 1.49 (t, 3H). |
| D35 | Et | 2-Br-5-$F_3$C-phenyl- | 8.58 (d, 1H), 8.37 (d, 1H), 8.23 (bs, 1H), 7.87-7.89 (m, 2H), 7.59-7.61 (dd, 1H), 4.36-4.43 (m, 2H), 1.50 (t, 3H). |
| D36 | Et | 2,3,6-tri-Cl-phenyl- | 8.59 (d, 1H), 8.39 (d, 1H), 8.11 (bs, 1H), 7.53 (d, 1H), 7.43 (d, 1H), 4.39 (q, 2H), 1.48 (t, 3H). |
| D37 | $F_2HC—H_2C—$ | 2-Cl-3-$F_3$C-phenyl- | 8.57 (d, 1H), 8.45 (d, 1H), 7.83 (t, 2H), 7.51 (t, 1H), 6.08-6.38 (tt, 1H), 4.54-4.80 (m, 2H). |

TABLE D-continued

Compound of formula (D'), i.e. a compound of formula (I) wherein $R^1$ and $R^2$ are hydrogen, $R^5$ is hydroxy, and $R^3$ and $R^4$ have the values as described in the table below.

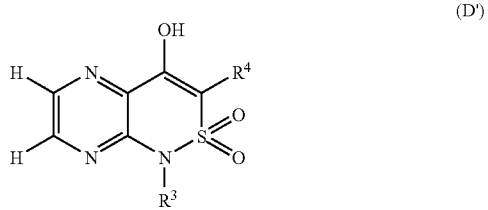

(D')

| Compound No. | $R^3$ | $R^4$ | 1H-NMR (400 MHz, CDCl$_3$ except where indicated; chemical shifts in ppm) |
|---|---|---|---|
| D38 | Et | 2-Cl-3-F$_3$C-phenyl- | 8.56 (d, 1H), 8.35 (d, 1H), 7.84 (d, 2H), 7.50 (t, 1H), 4.33-4.43 (m, 2H), 1.49 (t, 3H). |
| D39 | F$_2$HC—H$_2$C— | 2-F-6-F$_3$C-phenyl- | 8.54 (d, 1H), 8.41 (d, 1H), 7.57-7.99 (m, 2H), 7.38-7.42 (m, 1H), 5.96-6.26 (tt, 1H), 4.43-4.78 (m, 2H). |
| D40 | HC≡C—H$_2$C— | 2-nitro-phenyl- | 1:1 Mixture of prop-2-yn-1-yl isomer and propa-1,2-dien-1-yl isomer.<br>Prop-2-yn-1-yl isomer:<br>8.43 (d, 1H), 8.41 (d, 1H), 8.16 (d, 1H), 7.65-7.84 (m, 3H), 5.02 (t, 2H), 2.34 (t, 3H).<br>Propa-1,2-dien-1-yl isomer:<br>8.64 (d, 1H), 8.59 (d, 1H), 8.16 (d, 1H), 7.65-7.84 (m, 3H), 6.70 (t, 1H), 5.49 (d, 2H). |
| D41 | F$_2$HC—H$_2$C— | 5-Me-2-F$_3$C-phenyl- | 8.58 (d, 1H), 8.46 (d, 1H), 8.06 (s, 1H), 7.72 (d, 1H), 7.52 (s, 1H), 7.43 (d, 1H), 6.03-6.33 (m, 1H), 4.83-4.93 (m, 1H), 4.42-4.54 (m, 1H), 2.48 (s, 3H). |
| D42 | F$_2$HC—H$_2$C— | 2,6-bis-F$_3$C-phenyl- | 8.51 (d, 1H), 8.39 (d, 1H), 8.14 (d, 2H), 7.85 (t, 1H), 6.14-6.44 (m, 1H), 4.49-4.57 (dt, 2H). |
| D43 | Et | 2,6-bis-F$_3$C-phenyl- | 8.61 (d, 1H), 8.40 (d, 1H), 8.06 (d, 2H), 7.77 (t, 1H), 4.32 (q, 2H), 1.49 (t, 3H). |
| D44 | F$_2$HC—H$_2$C— | 2-I-phenyl- | 8.58 (d, 1H), 8.46 (d, 1H), 8.15 (bs, 1H), 8.01-8.03 (d, 1H), 7.61 (dd, 1H), 7.50 (t, 1H), 7.20 (dt, 1H), 6.12-6.42 (m, 1H), 4.80-4.91 (m, 1H), 4.51-4.63 (m, 1H). |
| D45 | HC≡C—H$_2$C— | 2,5-di-Cl-6-F$_3$C-phenyl- | 8.67 (d, 1H), 8.47 (d, 1H), 7.73 (d, 1H), 7.68 (d, 1H), 5.00 (d, 2H), 2.29 (t, 1H). |
| D46 | Me | 2-Cl-5-F$_3$C-phenyl- | 8.58 (d, 1H), 8.37 (d, 1H), 7.91 (bs, 1H), 7.70 (bs, 2H), 3.70 (s, 3H). |
| D47 | Me | 2,3,6-tri-Cl-phenyl- | 8.59 (d, 1H), 8.39 (d, 1H), 8.16 (bs, 1H), 7.53-7.55 (d, 1H), 7.42-7.45 (d, 1H), 3.70 (s, 3H). |
| D48 | Me—C≡C—H$_2$C— | 2,5-di-Cl-6-F$_3$C-phenyl- | 8.58 (d, 1H), 8.35 (d, 1H), 7.58-7.64 (m, 2H), 4.87-4.88 (m, 2H), 1.69-1.70 (m, 3H). |
| D49 | Et | 2,3-di-Cl-phenyl- | 8.56 (d, 1H), 8.36 (d, 1H), 7.59 (t, 2H), 7.34 (t, 1H), 4.32-4.46 (m, 2H), 1.50 (t, 3H). |
| D50 | F$_2$HC—H$_2$C— | 2,3-di-Cl-phenyl- | 8.56 (d, 1H), 8.44 (d, 1H), 7.53-7.61 (m, 2H), 7.33 (t, 1H), 6.07-6.37 (tt, 1H), 4.69-4.80 (m, 1H), 4.53-4.65 (m, 1H). |
| D51 | F$_3$C—H$_2$C— | 2,4-di-Cl-phenyl- | 8.61 (d, 1H), 8.50 (d, 1H), 8.18 (bs, 1H), 7.54-7.60 (m, 2H), 7.38-7.41 (m, 1H), 4.87-5.4 (m, 2H). |
| D52 | Et | 5-Cl-2-F$_3$C-phenyl- | 8.59 (d, 1H), 8.38 (d, 1H), 8.11 (bs, 1H), 7.77 (d, 1H), 7.73 (s, 1H), 7.59-7.62 (d, 1H), 4.29-4.47 (m, 2H), 1.46 (t, 3H). |
| D53 | F$_2$HC—H$_2$C— | 5-Cl-2-F$_3$C-phenyl- | 8.61 (d, 1H), 8.47 (d, 1H), 8.14 (bs, 1H), 7.77-7.79 (d, 1H), 7.72 (s, 1H), 7.61-7.63 (d, 1H), 6.02-6.35 (m, 1H), 4.82-4.92 (m, 1H), 4.43-4.55 (m, 1H). |

TABLE D-continued

Compound of formula (D'), i.e. a compound of formula (I) wherein $R^1$ and $R^2$ are hydrogen, $R^5$ is hydroxy, and $R^3$ and $R^4$ have the values as described in the table below.

(D')

| Compound No. | $R^3$ | $R^4$ | 1H-NMR (400 MHz, CDCl$_3$ except where indicated; chemical shifts in ppm) |
|---|---|---|---|
| D54 | H$_2$C=HC—H$_2$C— | 5-Cl-2-F$_3$C-phenyl- | 8.55 (d, 1H), 8.36 (d, 1H), 7.74 (d, 1H), 7.71 (s, 1H), 7.58 (d, 1H), 5.96-6.06 (m, 1H), 5.23-5.40 (m, 2H), 4.81-4.97 (m, 2H). |
| D55 | F$_2$HC—H$_2$C— | 2,4-bis-F$_3$C-phenyl- | d$_6$-DMSO: 8.57 (d, 1H), 8.53 (d, 1H), 8.07-8.10 (m, 2H), 7.74 (d, 1H), 6.12-6.42 (tt, 1H), 4.36-4.60 (m, 2H). |
| D56 | F$_2$HC—H$_2$C— | 4-Br-2-F$_3$C-phenyl- | d$_6$-DMSO: 8.68 (d, 1H), 8.65 (d, 1H), 8.03 (d, 1H), 7.99 (dd, 1H), 7.47 (d, 1H), 6.14-6.43 (tt, 1H), 4.41-4.61 (m, 2H). |
| D57 | F$_2$HC—H$_2$C— | 2,3-di-Cl-6-F$_3$C-phenyl- | 8.75 (d, 1H), 8.71 (d, 1H), 8.01 (d, 1H), 7.88 (d, 1H), 6.18-6.48 (m, 1H), 4.46-4.54 (m, 2H). |
| D58 | F$_2$HC—H$_2$C— | 3-EtO(CO)-6-F$_3$C-pyrid-2-yl- | 3:1 Mixture of ethyl ester and methyl ester. Ethyl ester: 8.67 (d, 1H), 8.57 (d, 1H), 7.77 (d, 1H), 7.30 (m, 1H), 5.67-5.91 (m, 1H), 4.65-4.71 (m, 1H), 4.52-4.57 (m, 2H), 4.31-4.39 (m, 1H), 1.49 (t, 3H). Methyl ester: 8.67 (d, 1H), 8.57 (d, 1H), 7.77 (d, 1H), 7.30 (m, 1H), 5.67-5.91 (m, 1H), 4.65-4.71 (m, 1H), 4.31-4.39 (m, 1H), 4.08 (s, 3H). |
| D59 | F$_2$HC—H$_2$C— | 2-Cl-4-I-phenyl- | 8.55 (d, 1H), 8.41 (d, 1H), 7.91 (s, 1H), 7.72 (d, 1H), 7.33 (d, 1H), 6.07-6.38 (m, 1H), 4.53-4.78 (m, 2H). |
| D60 | F$_2$HC—H$_2$C— | 2-Cl-6-F-5-MeO-phenyl- | 8.57 (d, IH), 8.44 (d, 1H), 7.27 (d, 1H), 7.04 (t, 1H), 6.06-6.36 (m, 1H), 4.59-4.77 (m, 2H), 3.90 (s, 3H). |
| D61 | F$_2$HC—H$_2$C— | 2-Cl-6-F$_3$C-phenyl- | Atropisomer A |
| D62 | F$_2$HC—H$_2$C— | 2-Cl-6-F$_3$C-phenyl- | Atropisomer B |

Key:

s = singlet; bs = broad singlet; d = doublet; t = triplet; q = quartet; dd = double doublet; dt = double triplet; tt = triple triplet; m = multiplet; Me = methyl; Et = ethyl.

TABLE E

Compound of formula (E'), i.e. a compound of formula (I) wherein $R^1$ and $R^2$ are hydrogen, $R^5$ is hydroxy, and $R^3$, $R^4$ and have the values as described in the table below.

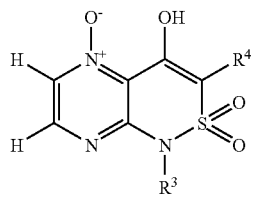
(E')

| Compound No. | $R^3$ | $R^4$ | 1H-NMR (400 MHz, CDCl$_3$ except where indicated; chemical shifts in ppm) |
|---|---|---|---|
| E1 | F$_2$HC—CH$_2$— | 2-Cl-5-F$_3$C-phenyl- | 8.48 (d, 1H), 8.03 (d, 1H), 7.80 (s, 1H), 7.68 (d, 2H), 6.03-6.33 (m, 1H), 4.72-4.83 (m, 1H), 4.55-4.67 (m, 1H). |
| E2 | F$_2$HC—CH$_2$— | 2-Cl-6-F$_3$C-phenyl- | 8.48 (d, 1H), 8.07 (d, 1H), 7.75-7.79 (m, 2H), 7.55-7.59 (m, 1H), 6.01-6.32 (m, 1H), 4.57-4.75 (m, 2H). |

Key:
s = singlet; d = doublet; m = multiplet.

Biological Examples

Compound Nos. A5 and A6 of Table A, Compound Nos. B5 and B6 of Table B and Compound No. D46 of Table D were not tested. The test results of all other compounds are reported below.

Example B1

Herbicidal Action

Seeds of a variety of test species were sown in sterilized standard soil in seed trays each having 96 cells. After cultivation for 8 to 9 days cultivation (post-emergence) under controlled conditions in a climatic chamber (cultivation at 23/17° C., day/night; 13 hours light; 50-60% humidity), the plants were treated with an aqueous spray solution of 1000 mg/l of the active ingredient dissolved in 10% DMSO (dimethyl sulfoxide, CAS RN 67-68-5) as a solvent, equivalent to 1000 g/ha. The plants were grown in the climatic chamber after application at (24/19° C., day/night; 13 hours light; 50-60% humidity) and watered twice daily. After 9 days until the test was evaluated (10=total damage to plant, 0=no damage to plant)

TABLE B1

Application post-emergence

| Comp No. | Rate (g/ha) | STEME | NAAOF | AMARE | SOLNI |
|---|---|---|---|---|---|
| B1 | 1000 | 0 | 0 | 0 | 2 |
| B3 | 1000 | 0 | 0 | 0 | 2 |
| C1 | 1000 | 6 | 4 | 0 | 3 |
| C2 | 1000 | 6 | 4 | 3 | 0 |
| C3 | 1000 | 2 | 2 | 1 | 3 |
| C4 | 1000 | 8 | 6 | 7 | 5 |
| C5 | 1000 | 7 | 8 | 5 | 1 |
| C6 | 1000 | 8 | 8 | 0 | 7 |
| C7 | 1000 | 8 | 8 | 3 | 7 |
| C8 | 1000 | 0 | 0 | 2 | 7 |
| C9 | 1000 | 6 | 6 | 7 | 4 |
| C40 | 1000 | 1 | 0 | 0 | 0 |
| C41 | 1000 | 4 | 8 | 0 | 0 |
| D1 | 1000 | 8 | 7 | 0 | 0 |
| D2 | 1000 | 7 | 7 | 7 | 7 |

STEME = *Stellaria media*;
NAAOF = *Nasturtium officinale*;
AMARE = *Amaranthus retroflexus*;
SOLNI = *Solanum nigrum*.

Compound Nos. A1 to A4 of Table A, Compound Nos. B2 and B4 of Table B were tested using the same protocols and showed little or no damage to the test plants under the test conditions.

Example B2

Herbicidal Action

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days, the test was evaluated (10=total damage to plant; 0=no damage to plant).

TABLE B2

Application post-emergence

| Comp No. | Rate (g/ha) | SOLNI | AMARE | SETFA | ECHCG | IPOHE |
|---|---|---|---|---|---|---|
| C11 | 1000 | 6 | 1 | 4 | 3 | 2 |
| C13 | 1000 | 9 | 10 | 3 | 10 | 10 |
| C15 | 1000 | 9 | 9 | 2 | 7 | 8 |
| C16 | 1000 | 10 | 7 | 0 | 3 | 7 |
| C17 | 1000 | 9 | 8 | 4 | 5 | 7 |
| C18 | 1000 | 3 | 9 | 0 | 1 | 6 |
| C19 | 1000 | 6 | 9 | 0 | 4 | 8 |
| C20 | 1000 | 10 | 10 | 0 | 8 | 10 |
| C21 | 1000 | 10 | 7 | 4 | 6 | 9 |
| C22 | 1000 | 10 | 10 | 4 | 7 | 9 |
| C23 | 1000 | 6 | 5 | 3 | 4 | 4 |
| C24 | 1000 | 9 | 2 | 0 | 4 | 9 |
| C25 | 1000 | 10 | 9 | 0 | 6 | 9 |
| C26 | 1000 | 0 | 9 | 0 | 0 | 0 |
| C27 | 1000 | 9 | 7 | 6 | 3 | 6 |
| C28 | 1000 | 6 | 7 | 2 | 2 | 6 |
| C29 | 1000 | 5 | 2 | 0 | 4 | 5 |
| C30 | 1000 | 10 | 8 | 5 | 6 | 9 |
| C31 | 1000 | 9 | 8 | 7 | 8 | 8 |
| C32 | 1000 | 8 | 8 | 1 | 7 | 9 |
| C33 | 1000 | 6 | 1 | 0 | 0 | 5 |
| C34 | 1000 | 9 | 7 | 2 | 7 | 10 |
| C35 | 1000 | 10 | 10 | 7 | 7 | 10 |
| C36 | 1000 | 9 | 9 | 3 | 7 | 10 |
| C37 | 1000 | 9 | 8 | 6 | 8 | 9 |
| C38 | 1000 | 10 | 9 | 9 | 9 | 10 |
| C39 | 1000 | 10 | 9 | 4 | 4 | 9 |
| C42 | 1000 | 3 | 2 | 2 | 2 | 4 |
| C43 | 1000 | 6 | 5 | 3 | 5 | 5 |
| C44 | 1000 | 10 | 10 | 6 | 9 | 10 |

TABLE B2-continued

Application post-emergence

| Comp No. | Rate (g/ha) | SOLNI | AMARE | SETFA | ECHCG | IPOHE |
|---|---|---|---|---|---|---|
| C45 | 1000 | 7 | 0 | 1 | 4 | 9 |
| C46 | 1000 | 6 | 4 | 0 | 4 | 5 |
| C47 | 1000 | 10 | 10 | 7 | 4 | 7 |
| C48 | 1000 | 5 | 3 | 0 | 0 | 6 |
| C49 | 1000 | 9 | 9 | 6 | 8 | 9 |
| C50 | 1000 | 6 | 5 | 4 | 5 | 7 |
| C51 | 1000 | 7 | 5 | 0 | 1 | 6 |
| C52 | 1000 | 8 | 9 | 8 | 7 | 10 |
| C53 | 1000 | 5 | 8 | 5 | 8 | 4 |
| C54 | 1000 | 8 | 6 | 2 | 3 | 8 |
| C55 | 1000 | 7 | 7 | 2 | 2 | 8 |
| C56 | 1000 | 2 | 10 | 0 | 0 | 0 |
| C57 | 1000 | 10 | 10 | 3 | 4 | 10 |
| C58 | 1000 | 9 | 10 | 4 | 6 | 9 |
| C59 | 1000 | 10 | 10 | 3 | 7 | 10 |
| C60 | 1000 | 10 | 10 | 1 | 7 | 10 |
| C61 | 1000 | 10 | 10 | 10 | 9 | 10 |
| C62 | 1000 | 6 | 7 | 6 | 4 | 8 |
| C63 | 1000 | 9 | 9 | 7 | 7 | 10 |
| C64 | 1000 | 5 | 4 | 3 | 5 | 6 |
| C65 | 1000 | 2 | 2 | 2 | 0 | 1 |
| C67 | 1000 | 1 | 0 | 0 | 0 | 2 |
| C68 | 1000 | 2 | 0 | 0 | 0 | 1 |
| C69 | 1000 | 6 | 4 | 0 | 2 | 7 |
| C70 | 1000 | 8 | 7 | 1 | 7 | 10 |
| C71 | 1000 | 9 | 8 | 1 | 6 | 10 |
| C72 | 1000 | 10 | 9 | 1 | 6 | 10 |
| C73 | 1000 | 7 | 7 | 2 | 2 | 7 |
| C74 | 1000 | 6 | 7 | 3 | 4 | 7 |
| C75 | 1000 | 6 | 5 | 0 | 1 | 2 |
| C76 | 1000 | 3 | 0 | 0 | 0 | 0 |
| C77 | 1000 | 10 | 10 | 9 | 9 | 10 |
| C78 | 1000 | 6 | 4 | 3 | 4 | 3 |
| C79 | 1000 | 9 | 9 | 6 | 7 | 9 |
| C80 | 1000 | 10 | 10 | 0 | 6 | 10 |
| C81 | 1000 | 10 | 10 | 7 | 8 | 10 |
| C82 | 1000 | 10 | 10 | 8 | 9 | 10 |
| C83 | 1000 | 10 | 9 | 1 | 7 | 10 |
| C84 | 1000 | 10 | 9 | 7 | 7 | 8 |
| C85 | 1000 | 10 | 7 | 6 | 7 | 9 |
| C86 | 1000 | 6 | 5 | 2 | 5 | 4 |
| C87 | 1000 | 10 | 7 | 0 | 5 | 9 |
| C88 | 1000 | 9 | 9 | 4 | 6 | 9 |
| C89 | 1000 | 10 | 7 | 1 | 6 | 9 |
| C90 | 1000 | 10 | 8 | 1 | 2 | 9 |
| C91 | 1000 | 9 | 9 | 3 | 6 | 10 |
| C92 | 1000 | 9 | 6 | 3 | 4 | 9 |
| C93 | 1000 | 6 | 0 | 0 | 3 | 6 |
| C94 | 1000 | 9 | 6 | 2 | 6 | 9 |
| C95 | 1000 | 9 | 7 | 3 | 6 | 10 |
| C96 | 1000 | 7 | 0 | 0 | 1 | 4 |
| C97 | 1000 | 6 | 0 | 0 | 1 | 4 |
| C98 | 1000 | 3 | 0 | 0 | 0 | 0 |
| C99 | 1000 | 8 | 3 | 1 | 2 | 3 |
| C100 | 1000 | 9 | 4 | 2 | 2 | 6 |
| C101 | 1000 | 10 | 4 | 2 | 5 | 8 |
| C102 | 1000 | 7 | 1 | 0 | 0 | 6 |
| C103 | 1000 | 9 | 8 | 6 | 7 | 6 |
| C104 | 1000 | 10 | 10 | 3 | 6 | 9 |
| C105 | 1000 | 9 | 10 | 9 | 9 | 8 |
| C106 | 1000 | 7 | 6 | 0 | 1 | 3 |
| C107 | 1000 | 7 | 5 | 3 | 5 | 6 |
| C108 | 1000 | 7 | 4 | 2 | 3 | 3 |
| C109 | 1000 | 8 | 5 | 2 | 5 | 9 |
| C110 | 1000 | 8 | 9 | 4 | 5 | 8 |
| C111 | 1000 | 9 | 8 | 6 | 6 | 9 |
| C112 | 1000 | 10 | 10 | 6 | 6 | 9 |
| C113 | 1000 | 10 | 8 | 6 | 7 | 9 |
| C114 | 1000 | 10 | 4 | 2 | 0 | 6 |
| C115 | 1000 | 9 | 8 | 5 | 1 | 6 |
| C116 | 1000 | 10 | 10 | 3 | 2 | 6 |
| C117 | 1000 | 10 | 10 | 7 | 8 | 9 |
| C118 | 1000 | 8 | 6 | 4 | 5 | 4 |
| C119 | 1000 | 6 | 3 | 3 | 5 | 3 |
| C120 | 1000 | 9 | 9 | 9 | 8 | 10 |
| C121 | 1000 | 5 | 0 | 2 | 0 | 1 |
| C122 | 1000 | 9 | 5 | 3 | 2 | 6 |
| C123 | 1000 | 10 | 4 | 1 | 2 | 4 |
| C124 | 1000 | 2 | 10 | 0 | 0 | 2 |
| C125 | 1000 | 9 | 9 | 8 | 8 | 8 |
| C126 | 1000 | 9 | 9 | 4 | 7 | 7 |
| C127 | 1000 | 10 | 8 | 2 | 4 | 8 |
| C128 | 1000 | 9 | 7 | 0 | 0 | 8 |
| C129 | 1000 | 10 | 10 | 9 | 9 | 9 |
| C130 | 1000 | 10 | 10 | 7 | 8 | 10 |
| C131 | 1000 | 10 | 9 | 2 | 4 | 9 |
| C132 | 1000 | 10 | 10 | 7 | 6 | 10 |
| C133 | 1000 | 10 | 10 | 7 | 8 | 8 |
| C134 | 1000 | 8 | 8 | 4 | 5 | 3 |
| C135 | 1000 | 10 | 8 | 10 | 7 | 8 |
| C136 | 1000 | 8 | 3 | 2 | 0 | 7 |
| C137 | 1000 | 9 | 7 | 8 | 3 | 8 |
| C138 | 1000 | 7 | 0 | 0 | 1 | 2 |
| C139 | 1000 | 0 | 0 | 3 | 0 | 1 |
| C140 | 1000 | 2 | 0 | 0 | 0 | 2 |
| C141 | 1000 | 8 | 7 | 0 | 2 | 7 |
| C142 | 1000 | 6 | 4 | 0 | 1 | 3 |
| C143 | 1000 | 10 | 1 | 0 | 4 | 8 |
| C144 | 1000 | 4 | 0 | 0 | 0 | 7 |
| C145 | 1000 | 8 | 0 | 2 | 5 | 8 |
| C146 | 1000 | 7 | 8 | 2 | 4 | 9 |
| C147 | 1000 | 9 | 1 | 3 | 2 | 9 |
| C148 | 1000 | 9 | 7 | 2 | 3 | 8 |
| C149 | 1000 | 8 | 10 | 0 | 0 | 0 |
| D3 | 1000 | 1 | 10 | 0 | 1 | 1 |
| D4 | 1000 | 10 | 8 | 2 | 4 | 10 |
| D5 | 1000 | 10 | 10 | 6 | 4 | 9 |
| D6 | 1000 | 10 | 10 | 5 | 7 | 9 |
| D7 | 1000 | 5 | 9 | 0 | 0 | 3 |
| D8 | 1000 | 2 | 9 | 0 | 0 | 0 |
| D9 | 1000 | 10 | 9 | 2 | 4 | 10 |
| D10 | 1000 | 10 | 9 | 2 | 4 | 9 |
| D11 | 1000 | 10 | 10 | 8 | 8 | 9 |
| D12 | 1000 | 9 | 6 | 2 | 0 | 5 |
| D13 | 1000 | 9 | 8 | 2 | 5 | 9 |
| D14 | 1000 | 9 | 9 | 5 | 7 | 9 |
| D15 | 1000 | 9 | 9 | 4 | 2 | 9 |
| D16 | 1000 | 10 | 10 | 2 | 5 | 9 |
| D17 | 1000 | 10 | 10 | 9 | 9 | 10 |
| D18 | 1000 | 10 | 10 | 5 | 4 | 10 |
| D19 | 1000 | 2 | 0 | 0 | 0 | 0 |
| D20 | 1000 | 5 | 3 | 1 | 1 | 6 |
| D21 | 1000 | 9 | 8 | 6 | 6 | 9 |
| D22 | 1000 | 10 | 10 | 6 | 7 | 10 |
| D23 | 1000 | 8 | 8 | 2 | 2 | 9 |
| D24 | 1000 | 10 | 6 | 1 | 3 | 10 |
| D25 | 1000 | 10 | 10 | 4 | 3 | 9 |
| D26 | 1000 | 8 | 8 | 4 | 7 | 8 |
| D27 | 1000 | 8 | 9 | 8 | 7 | 7 |
| D28 | 1000 | 9 | 10 | 8 | 8 | 8 |
| D29 | 1000 | 7 | 5 | 3 | 2 | 7 |
| D30 | 1000 | 10 | 10 | 3 | 6 | 10 |
| D31 | 1000 | 10 | 10 | 9 | 9 | 10 |
| D32 | 1000 | 6 | 5 | 1 | 0 | 5 |
| D33 | 1000 | 10 | 9 | 8 | 8 | 10 |
| D34 | 1000 | 1 | 0 | 1 | 0 | 2 |
| D35 | 1000 | 9 | 8 | 4 | 1 | 10 |
| D36 | 1000 | 10 | 10 | 2 | 6 | 10 |
| D37 | 1000 | 9 | 10 | 5 | 3 | 10 |
| D38 | 1000 | 8 | 9 | 0 | 1 | 5 |
| D39 | 1000 | 9 | 10 | 9 | 9 | 10 |
| D41 | 1000 | 10 | 9 | 2 | 1 | 9 |
| D42 | 1000 | 8 | 7 | 7 | 4 | 9 |
| D43 | 1000 | 8 | 7 | 4 | 3 | 8 |
| D44 | 1000 | 10 | 10 | 6 | 9 | 10 |
| D45 | 1000 | 9 | 8 | 6 | 6 | 8 |
| D47 | 1000 | 10 | 8 | 1 | 4 | 8 |
| D48 | 1000 | 8 | 3 | 0 | 0 | 7 |
| D49 | 1000 | 8 | 4 | 1 | 1 | 6 |
| D50 | 1000 | 10 | 5 | 2 | 1 | 8 |

TABLE B2-continued

Application post-emergence

| Comp No. | Rate (g/ha) | SOLNI | AMARE | SETFA | ECHCG | IPOHE |
|---|---|---|---|---|---|---|
| D51 | 1000 | 8 | 7 | 1 | 2 | 7 |
| D52 | 1000 | 7 | 5 | 4 | 4 | 5 |
| D53 | 1000 | 10 | 8 | 6 | 6 | 7 |
| D54 | 1000 | 7 | 2 | 3 | 3 | 4 |
| D55 | 1000 | 10 | 10 | 4 | 5 | 10 |
| D56 | 1000 | 9 | 10 | 6 | 7 | 10 |
| D57 | 1000 | 10 | 10 | 10 | 9 | 7 |
| D59 | 1000 | 8 | 4 | 1 | 3 | 4 |
| D60 | 1000 | 7 | 1 | 2 | 4 | 8 |
| E1 | 1000 | 9 | 4 | 1 | 3 | 7 |
| E2 | 1000 | 9 | 8 | 8 | 6 | 8 |

SOLNI = *Solanum nigrum*;
AMARE = *Amaranthus retroflexus*;
SETFA = *Setaria faberi*;
ECHCG = *Echinochloa crus-galli*;
IPOHE = *Ipomea hederaceae*.

Compound Nos. C10, C14 and C66 of Table C and Compound Nos. D40 and D58 of Table D were tested using the same protocols and showed little or no damage to the test plants under the test conditions.

Example B3

Herbicidal Action

Seeds of a variety of test species were sown in sterilized compost in small pots. After cultivation for seven days (post-emergence) in controlled conditions in the glasshouse (at 24/16° C., day/night; 14 hours light; 65% humidity) the plants were sprayed with 1 mg of the active ingredient, formulated in 2.5 ml acetone/water (50:50) solution, which is equivalent to 1000 g/ha. Once the foliage was dry, the pots were kept in the glasshouse (at 24/16° C., day/night; 14 hours light; 65% humidity), and were watered twice daily. After 13 days the test was evaluated (10=total damage to plant, 0=no damage to plant).

TABLE B3

Application post-emergence

| Comp No. | Rate (g/ha) | AMARE | ALOMY | DIGSA | CHEAL |
|---|---|---|---|---|---|
| C12 | 1000 | — | 6 | — | 9 |

AMARE = *Amaranthus retroflexus*;
ALOMY = *Alopecurus myosuroides*;
DIGSA = *Digitaria sanguinalis*;
CHEAL = *Chenopodium album*.

The invention claimed is:
1. A compound of formula (I)

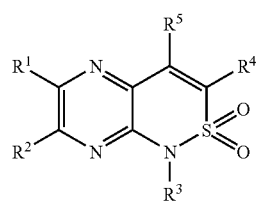

(I)

wherein
$R^1$ and $R^2$ are independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$ which may be the same or different, or heteroaryl or heteroaryl substituted by one to five $R^6$, which may be the same or different;
$R^3$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N-$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different;
$R^4$ is aryl or aryl substituted by one to five $R^8$, which may be the same or different, or heteroaryl or heteroaryl substituted by one to four $R^8$, which may be the same or different;
$R^5$ is hydroxy $R^9$-oxy-, $R^{10}$-carbonyloxy-, tri-$R^{11}$-silyloxy- or $R^{12}$-sulfonyloxy-;
each $R^6$, $R^7$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-$C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or alkyl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy- substituted by one to three $R^{13}$, which may be the same or different, heteroaryloxy- or heteroaryloxy- substituted by one to three $R^{13}$, which may be the same or different, arylthio- or arylthio- substituted by one to three $R^{13}$, which may be the same or different, or heteroarylthio- or heteroarylthio- substituted by one to three $R^{13}$, which may be the same or different;
$R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;
$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_2$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-

$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy- substituted by one to three $R^{14}$, which may be the same or different, heteroaryloxy- or heteroaryloxy-substituted by one to three $R^{14}$, which may be the same or different, arylthio- or arylthio- substituted by one to three $R^{14}$, which may be the same or different, or heteroarylthio- or heteroarylthio-substituted by one to three $R^{14}$, which may be the same or different;

each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;

$R^{12}$ is $C_1$-$C_{10}$alkyl, $C_1$-$C_{10}$haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy;

each $R^{13}$ is independently halo, cyano, nitro, $C_1$-$C_6$alkyl, $C_1$-$C_6$haloalkyl or $C_1$-$C_6$alkoxy;

and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy; or a salt or N-oxide thereof.

2. A compound according to claim 1 wherein $R^1$ is hydrogen, $C_1$-$C_4$alkyl, $C_1$-$C_4$haloalkyl, halo, cyano, hydroxy or $C_1$-$C_4$alkoxy.

3. A compound according to claim 1 or claim 2 wherein $R^2$ is hydrogen, $C_1$-$C_4$alkyl, $C_1$-$C_4$haloalkyl, halo, cyano, hydroxy or $C_1$-$C_4$alkoxy.

4. A compound according to claim 1 wherein $R^3$ is hydrogen, $C_1$-$C_4$alkyl, $C_1$-$C_4$haloalkyl, $C_2$-$C_4$alkenyl, $C_2$-$C_4$haloalkenyl, $C_2$-$C_4$alkynyl or $C_2$-$C_4$haloalkynyl.

5. A compound according to claim 1 wherein $R^4$ is aryl or aryl substituted by one to five $R^8$, which may be the same or different.

6. A compound according to claim 1, wherein $R^3$ is hydrogen, methyl, ethyl, 2,2-difluoro-ethyl, 2,2,2-trifluoro-ethyl, allyl or propargyl.

7. A compound according to claim 5, wherein $R^4$ is phenyl substituted by two to three $R^8$, which may be the same or different.

8. A compound according to claim 5, wherein $R^4$ is 2,5-bis-(trifluoromethyl)-phenyl, 3-bromo-2-chloro-6-fluoro-phenyl, 4-bromo-2-trifluoromethyl-phenyl, 2-chloro-3,6-difluoro-phenyl, 2-chloro-5-fluoro-phenyl, 2-chloro-5-trifluoromethyl-phenyl, 2-chloro-6-trifluoromethyl-phenyl, 4-chloro-2-trifluoromethyl-phenyl, 5-chloro-2-trifluoromethyl-phenyl, 2,3-dichloro-6-fluoro-phenyl, 2,6-dichloro-phenyl, 2,6-dichloro-4-trifluoromethoxy-phenyl, 2-iodo-phenyl, or 2,3,6-trichloro-phenyl.

9. A compound according to claim 1 wherein $R^5$ is hydroxyl, $C_1$-$C_4$alkylcarbonyloxy-, $C_3$-$C_6$cyclocarbonyloxy-, $C_2$-$C_4$alkenylcarbonyloxy-, $C_2$-$C_4$alkynylcarbonyloxy-, $C_4$alkoxycarbonyloxy-, $C_2$-$C_4$alkenyloxycarbonyloxy-, $C_2$-$C_4$alkynylcarbonyloxy- or $C_1$-$C_4$alkylthiocarbonyloxy-.

10. A method of controlling plants which comprises applying to the plants or to the locus thereof a herbicidally effective amount of a compound of formula (I) as defined in claim 1.

11. A herbicidal composition which comprises a herbicidally effective amount of a compound of formula (I) as defined in claim 1 in addition to formulation adjuvants.

12. A herbicidal composition which comprises a herbicidally effective amount of a compound of formula (I) as defined in claim 1, optionally one or more further herbicides, and optionally one or more safeners.

* * * * *